United States Patent
Wallach et al.

(10) Patent No.: US 8,273,545 B2
(45) Date of Patent: Sep. 25, 2012

(54) SIVA UBIQUITINATION AND/OR DEGRADATION-RELATED ACTIVITY AND MODULATORS THEREOF

(75) Inventors: David Wallach, Rehovot (IL); Parameswaran Ramakrishnan, Kerala (IN); Wang Wangxia, Fu Jian (CN); Andrei Kovalenko, Rehovot (IL)

(73) Assignees: Yeda Research and Development Co. Ltd, Rehovot (IL); Weizmann Institute of Science, Rehovot (IL)

( * ) Notice: Subject to any disclaimer, the term of this patent is extended or adjusted under 35 U.S.C. 154(b) by 866 days.

(21) Appl. No.: 12/160,627

(22) PCT Filed: Jan. 11, 2007

(86) PCT No.: PCT/IL2007/000050
§ 371 (c)(1),
(2), (4) Date: Jul. 11, 2008

(87) PCT Pub. No.: WO2007/080593
PCT Pub. Date: Jul. 19, 2007

(65) Prior Publication Data
US 2010/0204091 A1   Aug. 12, 2010

(30) Foreign Application Priority Data
Jan. 12, 2006   (IL) .......................................... 173104

(51) Int. Cl.
*G01N 33/53* (2006.01)
*G01N 33/68* (2006.01)

(52) U.S. Cl. .......................................... 435/7.7; 436/86
(58) Field of Classification Search .......................... None
See application file for complete search history.

(56) References Cited

U.S. PATENT DOCUMENTS 6,010,853 A * 1/2000 Kanteti et al. ..................... 435/6
7,132,234 B2 * 11/2006 Lu et al. ............................. 435/5

FOREIGN PATENT DOCUMENTS

WO         9854323 A    12/1998
WO      2005051423 A2    6/2005

OTHER PUBLICATIONS

Van Baren, M. J., et al., 2002, "A double RING-H2 domain in RNF32, a gene expressed during sperm formation", Biochemical and Biophysical Research Communications, vol. 292, No. 1, pp. 58-65.*
Vardhini, D., et al., 2004, "RING finger-dependent ubiquitination by PRAJA potentially defines the functional status of the tumour suppressor Smad4", Gastroenterology, vol. 126, No. 4/Supplement 2, p. A-80, Abstract No. 630.*
Yu, X., et al., 2005, "The KSHV immediate-early transcription factor RTA encodes ubiquitin E3 ligase activity that targets IRF7 for proteosome-mediated degradation", Immunity, vol. 22, No. 1, pp. 59-70.*

(Continued)

*Primary Examiner* — Manjunath Rao
*Assistant Examiner* — William W Moore
(74) *Attorney, Agent, or Firm* — Nixon Peabody LLP; David S. Resnick; Leena H. Karttunen Contarino

(57) ABSTRACT

The present invention relates to the ubiquitination and/or degradation-related activity of a SIVA polypeptide and to agents capable of modulating said activity.

7 Claims, 17 Drawing Sheets

OTHER PUBLICATIONS

Bishop, G. A. (2004). The multifaceted roles of TRAFs in the regulation of B-cell function. Nat Rev Immunol 4, 775-786.

Bradley, J. R., and Pober, J. S. (2001). Tumor necrosis factor receptor-associated factors (TRAFs). Oncogene 20, 6482-6491.

Brummelkamp, T. R., et al., A system for stable expression of short interfering RNAs in mammalian cells. Science 296, 550-553. 2002.

Canicio, J., et al., (2001). Nuclear factor kappa B-inducing kinase and Ikappa B kinase-alpha signal skeletal muscle cell differentiation. J Biol Chem 276, 20228-20233.

Cao, C., et al., The ARG tyrosine kinase interacts with Siva-1 in the apoptotic response to oxidative stress. J Biol Chem 276, 11465-11468. 2001.

Choudhary, S., et al., (2005). Respiratory syncytial virus influences NF-kappaB-dependent gene expression through a novel pathway involving MAP3K14/NIK expression and nuclear complex formation with NF-kappaB2. J Virol 79, 8948-8959.

Chu F, et al., The Siva-1 putative amphipathic helical region (SAH) is sufficient to bind to BCL-XL and sensitize cells to UV radiation induced apoptosis. Apoptosis. Jan. 2004;9(1):83-95.

Chu, F., et al., Expression of Siva-1 protein or its putative amphipathic helical region enhances cisplatin-induced apoptosis in breast cancer cells: effect of elevated levels of BCL-2. Cancer Res 65, 5301-5309. 2005.

Chung, J. et al., All TRAFs are not created equal: common and distinct molecular mechanisms of TRAF-mediated signal transduction. J Cell Sci 115, 679-688. 2002.

Deng, L., et al., Activation of the IkappaB kinase complex by TRAF6 requires a dimeric ubiquitin-conjugating enzyme complex and a unique polyubiquitin chain. Cell 103, 351-361, 2000.

Fanslow, W. C., et al., Recombinant CD40 ligand exerts potent biologic effects on T cells. J Immunol 152, 4262-4269. 1994.

Foehr, E. D., et al., The NF-kappa B-inducing kinase induces PC12 cell differentiation and prevents apoptosis. J Biol Chem 275, 34021-34024. 2000.

Fontanari Krause et al, Abstract 3152, Blood, vol. 102, 11, Nov. 16, 2003.

Fortin, A., et al., The proapoptotic gene SIVA is a direct transcriptional target for the tumor suppressors p53 and E2F1. J Biol Chem 279, 28706-28714. 2004.

Glickman, M. H., and Ciechanover, A. The ubiquitin-proteasome proteolytic pathway: destruction for the sake of construction. Physiol Rev 82, 373-428. 2002.

Grech, A. P., et al., TRAF2 differentially regulates the canonical and noncanonical pathways of NF-kappaB activation in mature B cells. Immunity 21, 629-642. 2004.

Henke, A., et al., Apoptosis in coxsackievirus B3-caused diseases: interaction between the capsid protein VP2 and the proapoptotic protein siva. J Virol 74, 4284-4290. 2000.

Hofmann, K., and Falquet, L. A ubiquitin-interacting motif conserved in components of the proteasomal and lysosomal protein degradation systems. Trends Biochem Sci 26, 347-350. 2001.

Hofmann, R. M., and Pickart, C. M. In vitro assembly and recognition of Lys-63 polyubiquitin chains. J Biol Chem 276, 27936-27943. 2001.

Kajiura, F., et al., (2004). NF-kappa B-inducing kinase establishes self-tolerance in a thymic stroma-dependent manner. J Immunol 172, 2067-2075.

Karin, M., and Ben-Neriah, Y. Phosphorylation meets ubiquitination: the control of NF-[kappa]B activity. Annu Rev Immunol 18, 621-663. 2000.

Kovalenko, A., et al., The tumour suppressor CYLD negatively regulates NF-kappaB signalling by deubiquitination. Nature 424, 801-805. 2003.

Lee, Z. H., et al., Caspase-mediated cleavage of TRAF3 in FasL-stimulated Jurkat-T cells. J Leukoc Biol 69, 490-496. 2001.

Liao, G., et al., Regulation of the NF-kappaB-inducing kinase by tumor necrosis factor receptor-associated factor 3-induced degradation. J Biol Chem 279, 26243-26250. 2004.

Lois, C., et al., Germline transmission and tissue-specific expression of transgenes delivered by lentiviral vectors. Science 295, 868-872. 2002.

Malinin, N. L., et al., MAP3K-related kinase involved in NF-kappaB induction by TNF, CD95 and IL-1. Nature 385, 540-544. 1997.

Miyawaki, S., et al., (1994). A new mutation, aly, that induces a generalized lack of lymph nodes accompanied by immunodeficiency in mice. Eur J Immunol 24, 429-434.

Nocentini, G., and Riccardi, C. GITR: a multifaceted regulator of immunity belonging to the tumor necrosis factor receptor superfamily. Eur J Immunol 35, 1016-1022. 2005.

Padanilam, B. J., et al., Expression of CD27 and ischemia/reperfusion-induced expression of its ligand Siva in rat kidneys. Kidney Int 54, 1967-1975. 1998.

Petit PX, et al., SIVA: A new intracellular ligand of the CD4 receptor modulating T lymphocyte apoptosis via a caspase-dependent mitochondrial pathway, Paper presented at: ISAC congress XXII (France: Wiley-Liss, Div John Wiley & Sons Inc, 111 River ST, Hoboken, NJ 07030 USA). 2004.

Pomerantz, J. L., and Baltimore, D. (2002). Two pathways to NF-kappaB. Mol Cell 10, 693-695.

Qin, L. F., et al., Gene expression profiling by cDNA array in human hepatoma cell line in response to cisplatin treatment. Life Sci 70, 1677-1690. 2002.

Ramakrishnan, P., et al., Receptor-specific signaling for both the alternative and the canonical NF-kappaB activation pathways by NF-kappaB-inducing kinase. Immunity 21, 477-489. 2004.

Rigaut, G., et al., A generic protein purification method for protein complex characterization and proteome exploration. Nat Biotechnol 17, 1030-1032. 1999.

Schreiber, E., et al., Rapid detection of octamer binding proteins with 'mini-extracts', prepared from a small number of cells. Nucleic Acids Res 17, 6419. 1989.

Senftleben, U., et al., Activation by IKKalpha of a second, evolutionary conserved, NF-kappa B signaling pathway. Science 293, 1495-1499. 2001.

Shinkura, R., et al., Alymphoplasia is caused by a point mutation in the mouse gene encoding Nf-kappa binducing kinase. Nat Genet 22, 74-77, 1999.

Spinicelli, S., et al., GITR interacts with the pro-apoptotic protein Siva and induces apoptosis. Cell Death Differ 9, 1382-1384. 2002.

Wajant, H., and Scheurich, P. (2004). Progress in Molecular and Subcellular Biology. pp. 47-72. A. Beschin (Ed.) Invertebrate Cytokines Springer-Verlag. Berlin. Heidelberg. 2003.

Xiao, G., and Sun, S. C. Negative regulation of the nuclear factor kappa B-inducing kinase by a cis-acting domain. J Biol Chem 275, 21081-21085. 2000.

Xiao, G., et al., Induction of p100 processing by NF-kappaB-inducing kinase involves docking IkappaB kinase alpha (IKKalpha) to p100 and IKKalpha-mediated phosphorylation. J Biol Chem 279, 30099-30105. 2004.

Xu, L. G., et al., (2004). TRAF7 potentiates MEKK3-induced AP1 and CHOP activation and induces apoptosis. J Biol Chem 279, 17278-17282.

Xue, L., et al., Siva-1 binds to and inhibits BCL-X(L)-mediated protection against UV. Proc Natl Acad Sci U.S.A. 99 (10): 6925-6930, 2002.

Yoon, Y., et al., Murine Siva-1 and Siva-2, alternate splice forms of the mouse Siva gene, both bind to CD27 but differentially transduce apoptosis. Oncogene 18, 7174-7179. 1999.

Prasad, K.V.S. et al., "CD27, a member of the tumor necrosis factor receptor family, induces apoptosis and binds to Siva, a proapoptotic protein." Proc. Natl. Acad. Sci. USA 94:6346-6351, 1997.

Pickart, C.M., "Mechanisms underlying ubiquitination." U.S. National Library of Medicine: Annual Review of Biochemistry 70:503-533, 2001.

Joazeiro, C.A.P. and Weissman A.M., "RING finger proteins: mediators of ubiquitin ligase activity." Cell:102 (5):549-52, 2000.

Kudryashova, E., et al., "Trim32 is a ubiquitin ligase mutated in limb girdle muscular dystrophy type 2H that binds to skeletal muscle myosin and ubiquitinates actin." J Mol Biol 354(2):413-424, 2005.

Kallijärvi, J., et al., "TRIM37 defective in mulibrey nanism is a novel RING finger ubiquitin E3 ligase." Exp Cell Res. 308(1):146-155, 2005.

PY, B., et al., "Siva-1 and an alternative splice form lacking the death domain, Siva-2, similarly induce apoptosis in T lymphocytes via a caspase-dependent mitochondrial pathway." J Immunol. 172(7):4008-4017, 2004.

Database EMBL [Online] Mar. 15, 1999, XP002434280 retrieved from EBI.AC.UK accession No. aaw88226 Database accession No. aaw88226 abstract.

Database EMBL [Online] Mar. 15, 1999, XP002434281 retrieved from EBI.AC.UK accession No. AAW88223 Database accession No. AAW88223 abstract.

* cited by examiner

SIVA UBIQUITINATION AND/OR DEGRADATION-RELATED ACTIVITY AND MODULATORS THEREOF

CROSS REFERENCE TO RELATED APPLICATIONS

This application is a National Phase Entry Application under 35 U.S.C. §371 of co-pending International Application PCT/IL2007/00050 filed 11 Jan. 2007, which claims benefit of Israeli application No. 173104, filed on 12 Jan. 2006.

FIELD OF THE INVENTION

The present invention relates to the ubiquitination and/or degradation-related activity of a SIVA polypeptide and to agents capable of modulating said activity.

BACKGROUND OF THE INVENTION

SIVA is an adaptor protein that binds to the cytoplasmic tail of CD27 and GITR receptors of the TNF receptor (TNFR) family. It exists as two alternative splice isoforms, SIVA1 and SIVA2. SIVA1 is longer and contains a death domain homology region (DDHR) with a putative amphipathical helix in its central part. SIVA2 is shorter and lacks the DDHR. Both isoforms contain a B-box-like ring finger and a Zinc finger like domain in their C-termini. Enforced expression of both SIVA1 and SIVA2 has been shown to induce apoptosis (Prasad et al., 1997, Yoon et al., 1998, Spinicelli et al., 2003, (Py et al., 2004). SIVA1 induced apoptosis is suggested to be effected by its binding to and inhibition of the anti apoptotic Bcl-2 family members through its amphipathic helical region (Chu et al., 2005; Chu et al., 2004; Xue et al., 2002). Consistent with the pro-apoptotic role, SIVA is a direct transcriptional target for the tumor suppressors p53 and E2F1 (Fortin et al., 2004). Various point of evidence indicate that SIVA is a stress-induced protein and is up-regulated in acute ischemic injury (Padanilam et al., 1998), coxavirus infection (Henke et al., 2000), and also by cisplatin treatment (Qin et al., 2002), as well as TIP30 expression which induces apoptosis (Xiao et al., 2000). Recently, the common N- and C-termini of SIVA1 and SIVA2, yet not the death domain, have been shown to be sufficient and capable to mediate apoptosis in lymphoid cells through activation of a caspase dependent mitochondrial pathway (Py et al., 2004).

NF-κB-inducing kinase, NIK, (MAP3K14) was discovered (Malinin et al., 1997) in a screening for proteins that bind to the TNF-receptor associated adaptor protein TRAF2. The marked activation of NF-κB upon overexpression of this protein kinase, and effective inhibition of NF-κB activation in response to a variety protein kinase, and effective inhibition of NF-κB activation in response to a variety of inducing agents, upon expression of catalytically inactive NIK mutants suggested that NIK participates in signaling for NF-κB activation (Malinin et al., 1997).

NIK has an in lymphoid organ development (Shinkura et al., 1999). Apart from the contribution to the regulation of the development and function of the immune system, NIK seems also to be involved in the regulation of various non-immune functions such as mammary gland development (Miyawaki et al., 1994). In vitro studies implicated NIK in signaling that leads to skeletal muscle cell differentiation (Canicio et al., 2001), and in the survival and differentiation of neurons (Foehr et al., 2000).

Assessment of the pattern of the NF-κB species in lymphoid organs indicated that, apart from its role in the regulation of NF-κB complex(es) comprised of Rel proteins and IκB, NIK also participates in controlling the expression/activation of other NF-κB species. Indeed, NIK has been shown to participate in site-specific phosphorylation of p100, which serves as a molecular trigger for ubiquitination and active processing of p100 to form p52. This p100 processing activity was found to be ablated by the aly mutation of NIK (Xiao et al., 2001b). NIK in thymic stroma is important for the normal production of Treg cells, which are essential for maintaining immunological tolerance. NIK mutation resulted in disorganized thymic structure and impaired production of Treg cells in aly mice (Kajiura et al., 2004). Consistently, studies of NIK-deficient mice also suggested a role for NIK in controlling the development and expansion of Treg cells (Lu et al., 2005). These findings suggest an essential role of NIK in establishing self-tolerance in a stromal dependent manner. NIK also partakes in NF-κB activation as a consequence of viral infection. Respiratory syncytial virus infection results in increased kinase activity of NIK and the formation of a complex comprised of activated NIK, IKK1, p100 and the processed p52 in alveolus like a549 cells. In this case NIK itself gets translocated into the nucleus bound to p52 and surprisingly, these events precede the activation of canonical NF-κB pathway activation (Choudhary et al., 2005). These findings indicate that NIK indeed serves as a mediator of NF-κB activation, but may also serve other functions, and that it exerts these functions in a cell- and receptor-specific manner.

NIK can be activated as a consequence of phosphorylation of the 'activation loop' within the NIK molecule. Indeed, mutation of a phosphorylation-site within this loop (Thr-559) prevents activation of NF-κB upon NIK overexpression (Lin et al., 1999). In addition, the activity of NIK seems to be regulated through the ability of the regions upstream and downstream of its kinase motif to bind to each other. The C terminal region of NIK downstream of its kinase moiety has been shown to be capable of binding directly to IKK1 (Regnier et al., 1997) as well as to p100 (Xiao et al., 2001b) and these interactions are apparently required for NIK function in NF-κB signaling. The N terminal region of NIK contains a negative-regulatory domain (NRD), which is composed of a basic motif (BR) and a proline-rich repeat motif (PRR) (Xiao and Sun, 2000). The N-terminal NRD interacts with the C-terminal region of NIK in cis, thereby inhibiting the binding of NIK to its substrate (IKK1 and p100). Ectopically expressed NIK spontaneously forms oligomers in which these bindings of the N-terminal to the C terminal regions in each NIK molecule are apparently disrupted, and display a high level of constitutive activity (Lin et al., 1999). The binding of the NIK C-terminal region to TRAF2 (as well as to other TRAF's) most likely participates in the activation process. However, its exact mode of participation is unknown.

Recently, a novel mechanism of NIK regulation has gained much attention. This concerns the dynamic interaction of NIK and TRAF3 leading to proteasome mediated degradation of NIK. Interestingly, inducers of the alternative pathway of NF-κB like CD40 and BLyS have been shown to induce TRAF3 degradation and concomitant enhancement of NIK expression (Liao et al., 2004).

There is rather limited information yet of the downstream mechanisms in NIK action. Evidence has been presented that NIK, through the binding of its C-terminal region to IKK1 can activate the NB kinase (IKK) complex. It has indeed been shown to be capable of phosphorylating serine-176 in the activation loop of IKK1 and thereby its activation (Ling et al., 1998).

It was suggested that NIK does not participate at all in the canonical NF-κB pathway, but rather serves exclusively to activate the alternative one (see (Pomerantz and Baltimore, 2002, for review).

Lately, it was shown that although the induction of IkappaB degradation in lymphocytes by TNF is independent of NIK, its induction by CD70, CD40 ligand, and BLyS/BAFF, which all also induce NF-kappaB2/p100 processing, does depend on NIK function (Ramakrishnan et al. 2004). Both CD70 and TNF induce recruitment of the IKK kinase complex to their receptors. In the case of CD70, but not TNF, this process is associated with NIK recruitment and is followed by prolonged receptor association of just IKK1 and NIK. Recruitment of the IKK complex to CD27, but not that of NIK, depends on NIK kinase function. These findings indicate that NIK participates in a unique set of proximal signaling events initiated by specific inducers, which activate both canonical and noncanonical NF-kappaB dimers.

TRAF family in mammals is comprised of seven members TRAF1-TRAF7(Bradley and Pober 2001, Xu et al., 2004). TRAFs play important functions in both adaptive and innate immunity, mainly by the activation of transcription factors NF-kB and AP1 (Wajant and Scheurich, 2004). All TRAF proteins share a C-terminal homology region termed TRAF domain that is capable of binding to the cytoplasmic domains of receptors and to other TRAF proteins. In addition TRAF2-TRAF7 proteins have Ring and Zinc finger motifs in their N terminus that are important for signaling downstream events.

Knock out mice on TRAFs genes were established (Reviewed by Bishop 2004, Bradley 2001, and Chung 2002). TRAF2 knock out die prematurely, show no TNF-mediated INK activation in fibroblasts. They show elevated serum TNF levels and increased sensitivity to TNF induced death in thymocytes and fibroblasts. In addition, they have B cells impaired in the TNF and CD40 induced canonical NF-κB activation. Also, they show deficient CD40 induced TRAF3 degradation and constitutive alternative NF-κB activation in B cells. TRAF3 knock out show deficient in all lineages of peripheral leukocytes. They show defective isotype switching in response to T-dependent antigens and LMP1 signaling defective in B cells.

SUMMARY OF THE INVENTION

In one aspect, the invention relates to a method for identifying a polypeptide harboring a B-box-like ring of SEQ ID NO:6 or a homolog thereof having ubiquitination-related activity comprising: (i) contacting polypeptides comprising an ubiquitin, an E1, an E2, and a polypeptide harboring a B-box-like ring of SEQ ID NO:6 or a homolog thereof; (ii) measuring linkage of ubiquitin to said polypeptide harbouring a B-box-like ring, wherein detection of ubiquitin linked to said polypeptide harboring a B-box-like ring is indicative that said polypeptide harboring a B-box-like ring has ubiquitination-related activity.

In another aspect, the invention relates to a method for identifying a polypeptide harboring a B-box-like ring of SEQ ID NO:6 or a homolog thereof having ubiquitination-related activity comprising: (i) contacting polypeptides comprising an ubiquitin, an E1, an E2, a TRAF2 polypeptide in the presence or the absence of a polypeptide harboring a B-box-like ring of SEQ ID NO:6 or a homolog thereof; (ii) measuring ubiquitin linked to the TRAF2 polypeptide in the presence and in the absence of the polypeptide harboring the B-box-like ring of SEQ ID NO: 6 or a homolog thereof; and (iii) comparing the level of ubiquitin linked to the TRAF2 in the presence and in the absence of the polypeptide, wherein an increase in the level of ubiquitin linked to TRAF2 in the presence of the polypeptide harboring the B-box ring is indicative that the polypeptide harboring the B-box-like ring of SEQ ID NO: 6 or a homolog thereof has ubiquitination-related activity.

In a further aspect, the invention relates to a method for identifying a SIVA polypeptide having ubiquitination-related activity comprising: (i) contacting polypeptides comprising an ubiquitin, an E1, an E2, and a SIVA polypeptide; (ii) and detecting whether said ubiquitin links to said SIVA polypeptide, wherein detection of ubiquitin linked to said SIVA polypeptide is indicative that said SIVA polypeptide has ubiquitination-related activity.

In one embodiment of the invention, the method is for identification of a SIVA polypeptide capable of having K63 ubiquitination-related activity.

In a further embodiment of the invention, the ubiquitin polypeptide is ubiquitin mutated at K48.

In another further aspect, the invention relates to a method for identifying a SIVA polypeptide having direct or indirect ubiquitination-related activity comprising: (i) contacting polypeptides comprising an ubiquitin, an E1, an E2, a NIK polypeptide, a TRAF3 polypeptide and optionally an E3 in the presence or the absence of a SIVA polypeptide; (ii) measuring the level of ubiquitination of the NIK and TRAF3 polypeptide in the presence and in the absence of the SIVA polypeptide; and (iii) comparing the level of ubiquitination of NIK and TRAF3 in the presence and in the absence of the SIVA polypeptide, wherein increase in the level of ubiquitination of NIK and TRAF3 in the presence of the SIVA polypeptide is indicative that the SIVA polypeptide has direct or indirect ubiquitination-related activity.

In another further aspect, the invention relates to a method for identifying a SIVA polypeptide having direct or indirect ubiquitination-related activity comprising: (i) contacting polypeptides comprising an ubiquitin, an E1, an E2, a NIK polypeptide, and optionally an E3 in the presence or the absence of a SIVA polypeptide; (ii) measuring the level of ubiquitination of the NIK polypeptide in the presence and in the absence of the SIVA polypeptide; and (iii) comparing the level of ubiquitination of NIK in the presence and in the absence of the SIVA polypeptide, wherein increase in the level of ubiquitination of NIK in the presence of the SIVA polypeptide is indicative that the SIVA polypeptide has direct or indirect ubiquitination-related activity.

In one embodiment of the invention a direct or indirect K48 or K63 ubiquitination-related activity of a SIVA polypeptide on a NIK polypeptide is tested.

In another further aspect, the invention relates to a method for identifying a SIVA polypeptide having direct or indirect ubiquitination-related activity comprising: (i) contacting polypeptides comprising an ubiquitin, an E1, an E2, a TRAF3 polypeptide, and optionally an E3 in the presence or the absence of a SIVA polypeptide; (ii) measuring the level of ubiquitination of the TRAF3 polypeptide in the presence and in the absence of the SIVA polypeptide; and (iii) comparing the level of ubiquitination of TRAF3 in the presence and in the absence of the SIVA polypeptide, wherein increase in the level of ubiquitination of TRAF3 in the presence of the SIVA polypeptide is indicative that the SIVA polypeptide has direct or indirect ubiquitination-related activity.

In one embodiment of the invention, the direct or indirect K63 ubiquitination-related activity of a SIVA polypeptide on a TRAF3 polypeptide is tested.

In a further embodiment of the invention, the SIVA polypeptide lacks the death domain.

In another further aspect, the invention relates to a method for identifying a SIVA polypeptide having direct or indirect ubiquitination-related activity comprising: (i) contacting polypeptides comprising an ubiquitin, an E1, an E2, a TRAF2, TRAF5 or TRAF6 polypeptide, and optionally an E3 in the presence or the absence of a SIVA polypeptide; and (ii) measuring the level of ubiquitination of the TRAF2, TRAF5 or TRAF6 polypeptide in the presence and in the absence of the SIVA polypeptide; and (iii) comparing the level of ubiquitination of TRAF2, TRAF5 or TRAF6 in the presence and in the absence of the SIVA polypeptide, wherein increase in the level of ubiquitination of TRAF2, TRAF5 or TRAF6 in the presence of the SIVA polypeptide is indicative that the SIVA polypeptide has direct or indirect ubiquitination-related activity.

In another further aspect, the invention relates to a method for identifying a SIVA polypeptide having direct or indirect ubiquitination-related activity comprising: (i) contacting polypeptides comprising an ubiquitin, an E1, an E2, a TRAF2 polypeptide, and optionally an E3 in the presence or the absence of a SIVA polypeptide; (ii) measuring the level of ubiquitination of the TRAF2 polypeptide in the presence and in the absence of the SIVA polypeptide; and (iii) comparing the level of ubiquitination of TRAF2 in the presence and in the absence of the SIVA polypeptide, wherein increase in the level of ubiquitination of TRAF2 in the presence of the SIVA polypeptide is indicative that the SIVA polypeptide has direct or indirect ubiquitination-related activity.

In one embodiment of the invention K48 ubiquitination-related activity of a SIVA polypeptide is tested.

In a further embodiment of the invention the SIVA polypeptide consists of SIVA2.

In another further aspect, the invention relates to a method for identifying an agent capable of modulating ubiquitination-related activity of polypeptide harboring a B-box-like ring of SEQ ID NO: 6 or a homolog thereof, comprising: (i) contacting polypeptides comprising an ubiquitin, an E1, an E2, the polypeptide harboring a B-box-like ring of SEQ ID NO: 6 or a homolog thereof in the presence or in the absence of a candidate agent, under conditions which allow ubiquitination of said polypeptide harboring a B-box-like ring polypeptide mediated by said polypeptide harboring a B-box-like ring; (ii) measuring the level of ubiquitination of said polypeptide harboring a B-box-like ring in the presence or in the absence of said candidate agent; and (iii) comparing the level of ubiquitination in the presence and in the absence of said candidate agent, wherein a change in the level of ubiquitination of a polypeptide harboring a B-box-like ring polypeptide in the presence of said candidate agent is indicative that the candidate agent is capable of modulating the ubiquitination-related activity of said polypeptide harboring a B-box-like ring.

In another further aspect, the invention relates to a method for identifying an agent capable of modulating ubiquitination-related activity of polypeptide harboring a B-box-like ring of SEQ ID NO: 6 or a homolog thereof, comprising: (i) contacting polypeptides comprising an ubiquitin, an E1, an E2, the polypeptide harboring a B-box-like ring of SEQ ID NO: 6 or a homolog thereof and TRAF2 in the presence or in the absence of a candidate agent, under conditions which allow ubiquitination of said polypeptide harboring a B-box-like ring and/or TRAF2 polypeptide mediated by said polypeptide harboring a B-box-like ring; (ii) measuring the level of ubiquitination of said polypeptide harboring a B-box-like ring and/or TRAF2 polypeptide in the presence or in the absence of said candidate agent; and (iii) comparing the level of ubiquitination in the presence and in the absence of said candidate agent, wherein a change in the level of ubiquitination of a polypeptide harboring a B-box-like ring and/or of a TRAF2 polypeptide in the presence of said candidate agent is indicative that the candidate agent is capable of modulating the ubiquitination-related activity of said polypeptide harboring a B-box-like ring.

In another further aspect, the invention relates to a method for identifying an agent capable of modulating a ubiquitination-related activity of a SIVA polypeptide, comprising: (i) contacting polypeptides comprising an ubiquitin, an E1, an E2, and the SIVA polypeptide in the presence or in the absence of a candidate agent, under conditions which allow self-ubiquitination of the SIVA polypeptide; (ii) measuring the level of self-ubiquitination of the SIVA polypeptide in the presence and in the absence of the candidate agent; and (iii) comparing the level of self-ubiquitination of said SIVA polypeptide in the presence and in the absence of said test agent, wherein a change in the level of self-ubiquitination of said SIVA polypeptide in the presence of said candidate agent is indicative that the candidate agent is capable of modulating the ubiquitination-related activity of SIVA.

In one embodiment of the invention the ubiquitin is ubiquitin mutated at K48.

In another further aspect, the invention relates to a method for identifying an agent capable of modulating a direct or indirect ubiquitination-related activity of a SIVA polypeptide comprising: (i) contacting polypeptides comprising a ubiquitin, an E1, an E2, a SIVA polypeptide, a NIK and/or TRAF3 polypeptide and optionally an E3, in the presence or in the absence of a candidate agent, under conditions which allow ubiquitination of said NIK and/or TRAF3 polypeptide mediated by said SIVA polypeptide; (ii) measuring the level of ubiquitination of said NIK and/or TRAF3 polypeptide in the presence or in the absence of said candidate agent; and (iii) comparing the level of ubiquitination in the presence or in the absence of said candidate agent, wherein a change in the level of NIK and/or TRAF3 polypeptide ubiquitination in the presence of said test agent is indicative that the candidate agent is capable of modulating the direct or indirect ubiquitination-related activity of SIVA.

In one embodiment of the invention the SIVA polypeptide is SIVA2.

In another further aspect, the invention relates to a method for identifying an agent capable of modulating a direct or indirect ubiquitination-related activity of a SIVA polypeptide comprising: (i) contacting polypeptides comprising a ubiquitin, an E1, an E2, a SIVA polypeptide, a NIK polypeptide and optionally an E3, in the presence or in the absence of a candidate agent, under conditions which allow ubiquitination of said NIK polypeptide mediated by said SIVA polypeptide; (ii) measuring the level of ubiquitination of said NIK polypeptide in the presence or in the absence of said candidate agent; and (iii) comparing the level of ubiquitination in the presence and in the absence of said candidate agent, wherein a change in the level of ubiquitination of the NIK polypeptide in the presence of said candidate agent is indicative that the candidate agent is capable of modulating the direct or indirect ubiquitination-related activity of SIVA.

In one embodiment of the invention the agent modulates direct or indirect K48 or K63 ubiquitination-related activity of a SIVA polypeptide on a NIK polypeptide.

In another further aspect, the invention relates to a method for identifying an agent capable of modulating a direct or indirect ubiquitination-related activity of a SIVA polypeptide comprising: (i) contacting polypeptides comprising a ubiquitin, an E1, an E2, a SIVA polypeptide, a TRAF3 polypeptide and optionally an E3, in the presence or in the absence of a candidate agent, under conditions which allow ubiquitination of said TRAF3 polypeptide mediated by said SIVA polypeptide; (ii) measuring the level of ubiquitination of said TRAF3 polypeptide in the presence or in the absence of said candidate agent; and (iii) comparing the level of ubiquitination in the presence or in the absence of said candidate agent, wherein a change in the level of TRAF3 polypeptide ubiquitination in the presence of said test agent is indicative that the candidate agent is capable of modulating the direct or indirect ubiquitination-related activity of SIVA polypeptide.

In one embodiment of the invention, the agent modulates direct or indirect K63 ubiquitination-related activity of a SIVA polypeptide.

In another further aspect, the invention relates to a method for identifying an agent capable of modulating a ubiquitination-related activity of a SIVA polypeptide, comprising: (i) contacting polypeptides comprising a ubiquitin, an E1, an E2, and the SIVA polypeptide with a TRAF2, TRAF5 or TRAF6 polypeptide in the presence or in the absence of a candidate agent, under conditions which allow ubiquitination of said TRAF2, TRAF5 or TRAF6 polypeptide mediated by the SIVA polypeptide; (ii) measuring the level of ubiquitination of said TRAF2, TRAF5 or TRAF6 polypeptide in the presence or in the absence of said candidate agent; and (iii) comparing the level of ubiquitination in the presence and in the absence of said candidate agent, wherein a change in the level of TRAF2, TRAF5 or TRAF6 polypeptide ubiquitination in the presence of said candidate agent is indicative that the candidate agent is capable of modulating the ubiquitination-related activity of SIVA.

In another further aspect, the invention relates to a method for identifying an agent capable of modulating a ubiquitination-related activity of a SIVA polypeptide, comprising: (i) contacting polypeptides comprising a ubiquitin, an E1, an E2, a SIVA polypeptide and a TRAF2, polypeptide in the presence or in the absence of a candidate agent, under conditions which allow ubiquitination of the TRAF2 polypeptide mediated by the SIVA polypeptide; (ii) measuring the level of ubiquitination of said TRAF2 polypeptide in the presence or in the absence of said candidate agent; and (iii) comparing the level of ubiquitination in the presence or in the absence of said candidate agent, wherein a change in the level of ubiquitination of the TRAF2 polypeptide in the presence of said candidate agent is indicative that the candidate agent is capable of modulating the ubiquitination-related activity of SIVA.

In one embodiment of the invention the agent modulates direct or indirect K63 ubiquitination-related activity of a SIVA polypeptide.

In a further embodiment of the invention contacting of polypeptides is carried out inside cells.

In a further embodiment of the invention contacting of the polypeptides is carried out in vitro or in cell free system or assay.

In a further embodiment of the invention ubiquitination is detected by Western blot analysis.

In another further aspect, the invention relates to a method for identifying a SIVA polypeptide capable of inducing protein degradation comprising (i) contacting peptides comprising a NIK and/or TRAF3 polypeptide in the presence or the absence of a SIVA polypeptide (ii) measuring NIK and/or TRAF3 polypeptide degradation in the presence or in the absence of the SIVA polypeptide; and (iii) comparing the level of degradation of NIK and/or TRAF3 polypeptide in the presence or the absence of the SIVA polypeptide, wherein detection of NIK and/or TRAF3 full or partial degradation in the presence of the SIVA polypeptide is indicative of the capability of the SIVA polypeptide to induce protein degradation.

In another further aspect, the invention relates to a method for identifying a SIVA polypeptide capable of inducing protein degradation comprising (i) contacting peptides comprising a NIK polypeptide in the presence or the absence of a SIVA polypeptide (ii) measuring NIK polypeptide degradation in the presence and in the absence of the SIVA polypeptide; and (iii) comparing the level of degradation of NIK polypeptide in the presence or the absence of the SIVA polypeptide, wherein detection of degradation of the NIK polypeptide in the presence of SIVA is indicative of the capability of the SIVA polypeptide to induce protein degradation.

In another further aspect, the invention relates to a method for identifying a SIVA polypeptide capable of inducing protein degradation comprising (i) contacting peptides comprising a TRAF3 polypeptide in the presence or the absence of a SIVA polypeptide (ii) measuring TRAF3 polypeptide degradation in the presence and in the absence of the SIVA polypeptide; and (iii) comparing the level of degradation of TRAF3 polypeptide in the presence or the absence of the SIVA polypeptide, wherein detection of TRAF3 partial or full degradation in the presence of SIVA is indicative of the capability of the SIVA polypeptide to induce protein degradation.

In one embodiment of the invention detection of a smaller fragment of TRAF3 (dTRAF3) is indicative of the capability of said SIVA polypeptide to induce protein degradation.

In another further aspect, the invention relates to a method for identifying an agent capable of modulating protein degradation mediated by the activity of a SIVA polypeptide, comprising: (i) contacting the SIVA polypeptide with NIK and/or TRAF3 in the presence or in the absence of a candidate agent under conditions which allow degradation of NIK and/or TRAF3 mediated by the SIVA polypeptide; (ii) measuring degradation of NIK and/or TRAF3 in the presence or in the absence of a candidate agent; and (iii) comparing the level of degradation of NIK and/or TRAF3 in the presence or in the absence of the candidate agent, wherein a change in the level of NIK and/or TRAF3 full or partial degradation in the presence of the candidate agent is indicative that the candidate agent is capable of modulating protein degradation mediated by the activity of a SIVA polypeptide.

In another further aspect, the invention relates to a method for identifying an agent capable of modulating protein degradation mediated by the activity of a SIVA polypeptide, comprising: (i) contacting the SIVA polypeptide with NIK in the presence or in the absence of a candidate agent under conditions which allow degradation of NIK mediated by SIVA; (ii) measuring degradation of NIK in the presence or in the absence of a candidate agent; and (iii) comparing the level of degradation of NIK in the presence or in the absence of the candidate agent, wherein a change in the level of NIK degradation in the presence of the candidate agent is indicative that the candidate agent is capable of modulating protein degradation mediated by the activity of a SIVA polypeptide.

In another further aspect, the invention relates to a method for identifying an agent capable of modulating protein degradation mediated by the activity of a SIVA polypeptide, comprising: (i) contacting the SIVA polypeptide with TRAF3 in the presence or in the absence of a candidate agent under conditions which allow degradation of TRAF3 mediated by SIVA; (ii) measuring degradation of TRAF3 in the presence or in the absence of a candidate agent; and (iii) comparing the level of degradation of TRAF3 in the presence and in the absence of the candidate agent, wherein a change in the level of TRAF3 full or partial degradation in the presence of the candidate agent is indicative that the candidate agent is capable of modulating protein degradation mediated by the activity of a SIVA polypeptide.

In one embodiment of the invention a change in the level of partial degradation and appearance of a smaller fragment of TRAF3 (dTRAF3) in the presence of the candidate agent is indicative that the candidate agent is capable of modulating protein degradation mediated by the activity of a SIVA polypeptide.

In another further aspect, the invention relates to a method for identifying an agent capable of modulating the association of a protein complex comprising NIK, TRAF3 and a SIVA polypeptide, the method comprising (i) contacting polypeptides comprising said NIK, TRAF3 and a SIVA polypeptide in the presence or in the absence of a candidate agent; (ii) measuring the level of NIK-TRAF3-SIVA complex in the presence or absence of the candidate agent; and (iii) comparing the level of the NIK-TRAF3-SIVA complex formed in the presence and in the absence of the candidate agent, wherein a change in the level of the NIK-TRAF3-SIVA complex formed in the presence of the candidate agent is indicative that the candidate agent is capable of modulating the association of the NIK, TRAF3 and a SIVA polypeptide complex.

In one embodiment of the invention said candidate agent decreases the level of the NIK, TRAF3 and SIVA polypeptide complex.

In a further embodiment of the invention said candidate agent increases the level of the NIK, TRAF3 and SIVA polypeptide complex.

In another further embodiment of the invention the SIVA polypeptide is SIVA2.

In another further embodiment of the invention said candidate agent is selected from small organic molecules, peptides, nucleic acids, molecules from natural extracts, and synthetic organic compounds.

In another further aspect, the invention provides the use of an agent capable of modulating the direct or indirect ubiquitination related activity of a polypeptide harboring a B box like ring of the sequence in SEQ ID NO: 6 or a homolog sequence thereof, in the manufacture of a medicament for treatment or prevention of a disease, disorder or condition whose pathology or course is associated with the activity and/or levels of TRAF2, NIK, TRAF3 and/or SIVA.

In one embodiment of the invention the disease is viral infection.

In another embodiment of the invention the agent is capable of modulating direct or indirect ubiquitination related activity of the polypeptide harboring the B box like ring consisting of SIVA.

In a further embodiment of the invention the SIVA polypeptide consists of SIVA2.

In another further embodiment of the invention the disease disorder or condition is a disease, disorder or condition whose pathology or course is associated with the activity and/or levels of TRAF2.

In another further embodiment of the invention the pathology is associated with TRAF2 upregulation/activation.

In another further embodiment of the invention the disease is inflammation.

In another further embodiment of the invention the disease disorder or condition is a disease, disorder or condition whose pathology or course is associated with the activity and/or levels of NIK.

In another further embodiment of the invention the pathology is associated with NIK upregulation/activation.

In another further embodiment of the invention the disease is cancer.

In another further embodiment of the invention the disease is an autoimmune disease.

In another further embodiment of the invention the disease disorder or condition is a disease, disorder or condition whose pathology or course is associated with the activity and/or levels of TRAF3.

In another further embodiment of the invention the pathology is associated with TRAF3 upregulation/activation.

In another further embodiment of the invention the condition is immune, deficiency.

In another further embodiment of the invention disease disorder or condition is a disease, disorder or condition whose pathology or course is associated with the activity and/or levels of SIVA.

In another further embodiment of the invention the pathology is associated with SIVA upregulation/activation.

In another further embodiment of the invention the disease disorder or condition is associated with chemo- and radiotherapy side effects and with ischemia and ischemic reperfusion.

In another further aspect, the invention provides the use of SIVA2 in the manufacture of a medicament for treatment or prevention of a disease, disorder or condition whose pathology or course is associated with excessive or increased levels of TRAF3.

In another further aspect, the invention provides the use of a SIVA mutated at the ring finger in the manufacture of a medicament for treatment or prevention of a disease, disorder or condition whose pathology or course is associated with decreased levels of TRAF3.

In one embodiment of the invention the mutated SIVA is SIVA2 C73A.

In another further aspect, the invention provides the use of NIK in the manufacture of a medicament for treatment or prevention of a disease, disorder or condition whose pathology or course is associated with levels of TRAF3, ubiquitination of TRAF 3 and/or degradation of TRAF3 in cells.

In another further aspect, the invention provides the use of an agent capable of modulating the ubiquitination ligase activity of a SIVA polypeptide and/or of modulating the protein degradation of a SIVA polypeptide, in the manufacture of a medicament for treating or preventing a disease, disorder or condition whose pathology or course is associated with the activity of TRAF2, NIK, TRAF3 and/or SIVA.

In another further aspect, the invention provides the use of an agent capable of modulating the ubiquitination ligase activity of a SIVA polypeptide and/or of modulating the protein degradation of a SIVA polypeptide, in the manufacture of a medicament for treating a disease, disorder or condition by modulating the immune system.

In another further aspect, the invention provides the use of a SIVA polypeptide in the manufacture of a medicament for treating a disease, disorder or condition by modulating the immune system.

In one embodiment, the invention relates to enhancement of the immune system.

In another embodiment, the invention relates to inhibiting the immune system.

In a further embodiment of the invention the agent consists of the SIVA-C terminus (SEQ ID NO: 3).

In a further embodiment of the invention the agent consists of SIVA2C73A. In a further embodiment of the invention the agent consists of SIVA 1-58 (SEQ ID NO: 4).

In a further embodiment of the invention the agent consists of SIVA 1-81 (SEQ ID NO: 5).

In another further aspect, the invention provides the use of a NIK mutant on the lysine residue 670 in the manufacture of a medicament for treating a disease, disorder or condition responsive to modulation of the immune system.

In another further aspect, the invention provides the use of an agent capable of modulating the ubiquitin related activity of a SIVA polypeptide identified by a method according to any one of the methods according to the invention in the manufacture of a medicament for treating a disease, disorder or condition responsive to modulation of the immune system.

In one embodiment of the invention the agent is a siRNA specific to SIVA.

In another further aspect, the invention provides the use of a SIVA polypeptide in the manufacture of a medicament for treating a disease, disorder or condition responsive to modulation of the immune system.

In another further aspect, the invention provides the use of an agent capable of modulating the formation of the NIK-SIVA-TRAF3 complex, in the manufacture of a medicament for the treatment of an immune disease disorder or condition.

In one embodiment of the invention the SIVA polypeptide is SIVA2.

In another further aspect, the invention provides the use of an agent capable of modulating the formation of NIK-SIVA-TRAF3 complex in the manufacture of a medicament for treating or preventing a disease disorder or condition whose pathology or course is associated with excessive NF-κB expression or activity.

In another further aspect, the invention provides the use of an agent capable of modulating the formation of the NIK-SIVA-TRAF3 complex, in the manufacture of a medicament for the treatment of a disease disorder or condition whose pathology or course is associated with excessive activity of NIK.

In one embodiment of the invention the disease, disorder or condition is inflammation.

In one embodiment of the invention the disease is cancer.

In another further aspect, the invention provides a polypeptide complex comprising NIK, TRAF3 and a SIVA polypeptide.

In one embodiment of the invention the SIVA polypeptide in the complex is SIVA2.

In another further aspect, the invention provides an isolated polypeptide consisting of a B box of the sequence set forth in SEQ ID NO: 6.

In another further aspect, the invention provides an isolated polypeptide comprising a C-terminal fragment of a SIVA polypeptide including the B-box-like ring finger and/or the Zinc finger motifs except for SIVA1 and SIVA2.

In another further aspect, the invention provides an isolated polypeptide consisting of amino acid residues 58 to 110 of SIVA2 set forth in SEQ ID NO: 3.

In another further aspect, the invention provides an isolated polypeptide comprising an N-terminal fragment of a SIVA polypeptide lacking the Zn finger motif 1-81 (SEQ ID NO: 5), or a fragment thereof.

In another further aspect, the invention provides an isolated polypeptide comprising an N-terminal fragment of a SIVA polypeptide lacking the Zn finger motif and the B-box-like ring finger motif of SIVA2 1-58 (SEQ ID NO: 4).

In another further aspect, the invention provides an isolated polypeptide consisting of SEQ ID NO: 4, SEQ ID NO: 5, SEQ ID NO: 3, SIVA2C73A or a fragment thereof.

In another further aspect, the invention provides an isolated polypeptide comprising a SIVA polypeptide mutated at a cysteine residue located at the ring finger motif.

In one embodiment of the invention the SIVA is SIVA2.

In one embodiment of the invention the SIVA2 polypeptide is mutated at cysteine residue at position 73.

In another further aspect, the invention provides a polypeptide NIK mutant on the lysine residue 670.

In one embodiment of the invention the mutant is NIK K670A.

In another further aspect, the invention provides a fusion polypeptide of a polypeptide according to the invention.

In another further aspect, the invention provides a salt of a polypeptide according to the invention.

In another further aspect, the invention provides an isolated polynucleotide encoding a polypeptide according to the invention.

In another further aspect, the invention provides an isolated polynucleotide comprising the sequence such as SEQ ID NO: 7 SEQ ID NO: 8 and SEQ ID NO: 9.

In another further aspect, the invention provides a vector comprising a polynucleotide according to the invention.

In another further aspect, the invention provides a host cell harboring a vector according to the invention.

In another further aspect, the invention provides a method for preparing of a polypeptide according to the invention, comprising culturing a host cell according to the invention and isolating the polypeptide produced.

In another further aspect, the invention provides a kit useful for the ubiquitination of a protein substrate comprising E1, E2, ubiquitin, a SIVA polypeptide, and instructions.

In one embodiment of the invention the protein substrate is selected from TRAF2, TRAF3, NIK and SIVA.

In another further aspect, the invention provides a pharmaceutical composition comprising a vector according to the invention and a pharmaceutically acceptable carrier.

In another further aspect, the invention provides a pharmaceutical composition comprising a polypeptide according to the invention or a salt thereof and a pharmaceutically acceptable carrier.

In another further aspect, the invention provides a pharmaceutical composition comprising a polynucleotide according to the invention and a pharmaceutically acceptable carrier.

In another further aspect, the invention provides a pharmaceutical composition comprising an agent capable of modulating the ubiquitin related activity of a polypeptide harboring a B-box-like ring of sequence of SEQ ID NO: 6 or a homolog sequence thereof, and a pharmaceutically acceptable carrier.

In one embodiment of the invention the polypeptide harboring the B-box-like ring is a SIVA polypeptide.

In another further aspect, the invention provides a pharmaceutical composition comprising an agent capable of modulating protein degradation mediated by the activity of a polypeptide harboring a B-box-like ring of sequence of SEQ ID NO: 6 or a homolog sequence thereof and a pharmaceutically acceptable carrier.

In one embodiment of the invention the polypeptide harboring the B-box-like ring is a SIVA polypeptide.

In another further aspect, the invention provides a pharmaceutical composition comprising an agent capable of modulating the ubiquitin ligase activity of a SIVA polypeptide or a homolog thereof, and a pharmaceutically acceptable carrier.

In another further aspect, the invention provides a method for modulating NIK ubiquitination in a cell comprising increasing or decreasing the level of a SIVA polypeptide activity or expression in said cell.

In another further aspect, the invention provides a method for inducing TRAF2 ubiquitination comprising contacting an ubiquitin, E1, E2, SIVA and TRAF2 under conditions suitable for ubiquitination.

DETAILED DESCRIPTION OF THE INVENTION

Figure 1:
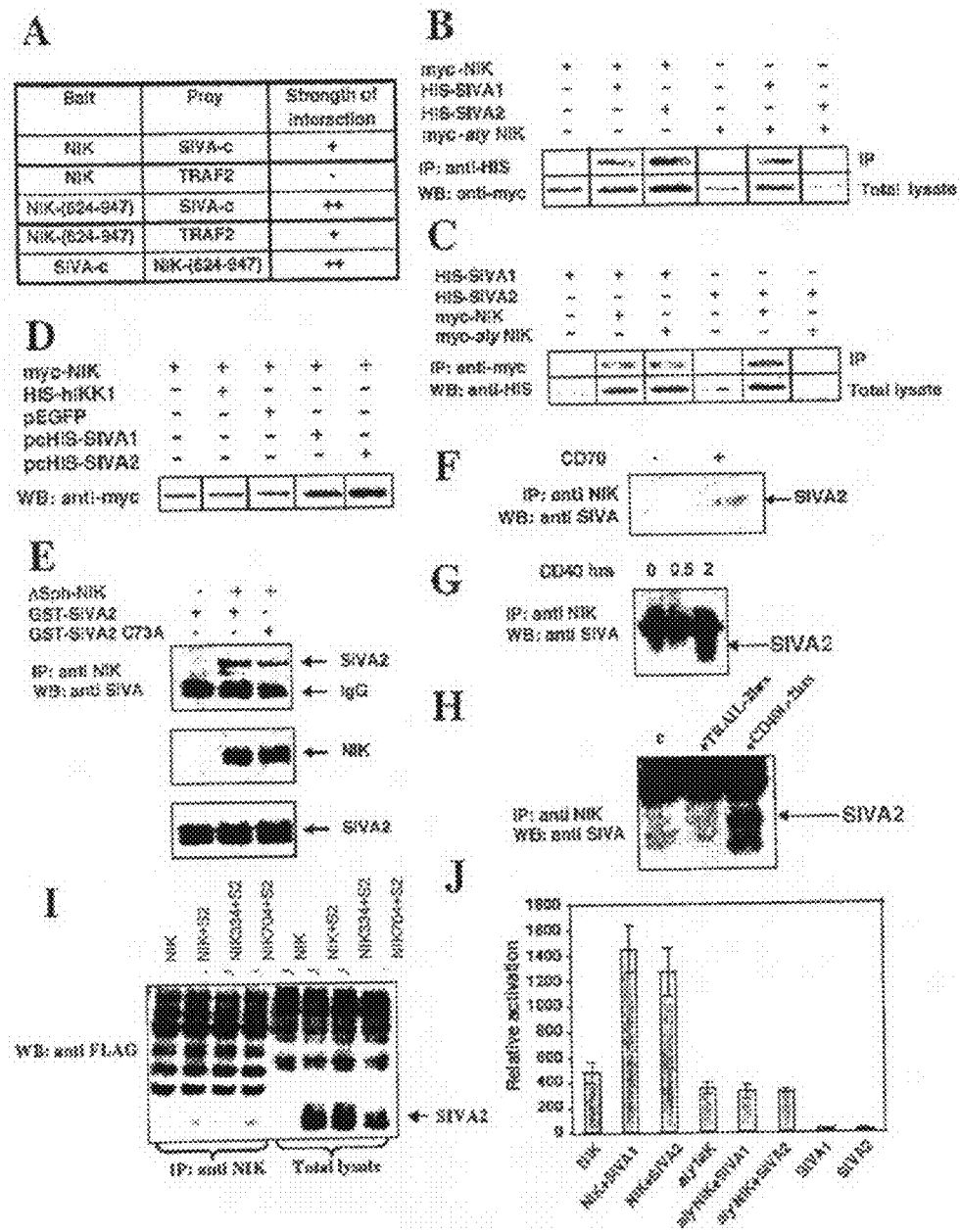
FIGS. 1A-1J show that SIVA binds NIK both in vivo and in vitro and modulates its function. A. Binding of NIK to SIVA in yeast two-hybrid tests. The binding of NIK and its N-terminally truncated mutant (NIK 624-947) to the C-terminal part of SIVA (amino acids 123-175 in SIVA1 or 58-110 in SIVA2) or TRAF2 was assessed in transformed SFY526 yeast. '++' and '+' indicate development of strong colour within one hour and 3 hours after initiation of the assay, respectively, and '−' no development of colour within 24 hours. B. Co-immunoprecipitation of NIK (or of NIK to which a missense mutation corresponding to that found in the aly mice was introduced) with SIVA and C, SIVA with NIK from transiently transfected HEK 293T cells. D. Enhancement of the expression of transfected NIK by co-expressed SIVA. NIK, SIVA, IKK1 and GFP were transfected in 1:1 ratio and total lysates were analysed by Western blotting 24 hrs post transfection. E. In vitro binding of NIK and SIVA2. Bacterially expressed GST-SIVA2 and baculovirally expressed NIK with out N-terminus were mixed and incubated at 30° C. for 30 min. Anti-NIK immunoprecipitate was analysed by Western blotting with anti-SIVA. F. CD70 facilitates the association of SIVA2 with NIK. Ramos cells constitutively expressing myc-tagged NIK was treated for 20 min with CD70 followed by immunoprecipitation of NIK and Western analysis of the association of SIVA with it. Culture supernatant of HEK 293T cells expressing CD70 was used at 50% dilution for treating cells in all the experiments. G. CD40L triggering prompts association of NIK with SIVA2. Human BJAB lymphoblastoid cells constitutively expressing transfected NIK were infected with a retroviral vector expressing SIVA2 and a puromycin-resistance selection marker. The puromycin resistant pool of cells was activated for indicated time points with CD40L or H. TRAIL (100 ng/ml). NIK was immunoprecipitated and co-precipitated SIVA analysed by Western blotting. For CD40L treatment, cells were resuspended in culture supernatants of HEK 293T cells expressing CD40L. I. Co-expression of NIK and its TRAF2 binding domain mutants in HeLa cells. (NIK 304*- amino acids 332-335, SVEE mutated to SVAA and NIK 704*-amino acids 702-705 PAEE mutated to PAAA). Anti-NIK immunoprecipitates analysed by Western blotting for SIVA2 co-precipitation (left-four lanes) and total lysates showing SIVA2 expression level (right-four lanes). J. Enhancement of NIK-mediated NF-κB activation by co-expressed SIVA. Effect of the over-expression of NIK, alone or together with SIVA1 or SIVA2 on the expression of NF-κB luciferase in HEK 293T cells was assessed 24 hrs after transfection. Note that the expression of aly NIK results just as well in significant NF-κB activation. However, SIVA does not enhance this activation. The data presented are the means of those obtained in two experiments in which each test was done in triplicates.

It was found according to the present invention, that SIVA has ubiquitination-related activity and is capable of directly inducing self-ubiquitination and ubiquitination of TRAF2.

Ubiquitylation, also termed ubiquitination, refers to the process particular to eukaryotes whereby a protein is post-translationally modified by covalent attachment of a small protein named ubiquitin [originally ubiquitous immunopoeitic polypeptide (UBIP)]. Ubiquitin ligase is a protein which covalently attaches ubiquitin to a lysine residue on a target protein. The ubiquitin ligase is typically involved in poly-ubiquitylation: a second ubiquitin is attached to the first, a third is attached to the second, and so forth.

The ubiquitin ligase is referred to as an "E3" and operates in conjunction with an ubiquitin-activating enzyme (referred herein as "E1") and an ubiquitin-conjugating enzyme (referred herein as "E2"). There is one major E1 enzyme, shared by all ubiquitin ligases, which uses ATP to activate ubiquitin for conjugation and transfers it to an E2 enzyme. The E2 enzyme interacts with a specific E3 partner and transfers the ubiquitin to the target protein. The E3, which may be a multi-protein complex, is generally responsible for targeting ubiquitination to specific substrate proteins. In some cases it receives the ubiquitin from the E2 enzyme and transfers it to the target protein or substrate protein; in other cases it acts by interacting with both the E2 enzyme and the substrate.

It has been shown according to the invention that SIVA2 is an E3 ligase. Thus, in one aspect, the invention relates to a method for identifying a SIVA polypeptide having ubiquitination related activity comprising: (i) contacting polypeptides comprising an ubiquitin, an E1, and an E2, with a SIVA polypeptide; (ii) and detecting whether said ubiquitin links or binds co-valently to said SIVA polypeptide, wherein detection of ubiquitin linked to said SIVA polypeptide is indicative that said SIVA polypeptide has ubiquitination-related activity.

The SIVA polypeptide can be any polypeptide derived or based on SIVA. Examples of SIVA polypeptides include, but are not limited to SIVA1 (SEQ ID NO: 1), SIVA2 (SEQ ID NO: 2) a mutein, fused protein, functional derivative, active fraction, isoform, circularly permutated derivative thereof. An example of E2 is Ubc13/Uev1.

In vitro or cell based methods can be used to identify a SIVA polypeptide that has ubiquitination related activity.

In one embodiment of the invention the method is an in vitro method and can be carried out as follows. A reaction mixture is prepared comprising a recombinant ubiquitin, E1, E2 and of recombinant SIVA polypeptide. The amount of recombinant protein used can be 8, 0.2, 1-2 µg/ml ubiquitin, E1, E2 and the SIVA polypeptide, respectively. The proteins can be in a suitable buffer, for example, a buffer containing, 30 mM HEPES pH 7.6, 5 mM MgCl2, 2 mM ATP, 0.2 mM DTT, 5 mM Sodium Citrate, 10 mM creatine phosphate, 0.7 µg/ml creatine kinase and 5 µM ubiquitin aldehyde. The reaction is incubated at 30° C. for about 1-4 hours. The reaction may be terminated by addition of Laemmli sample buffer or diluted to 1 ml with buffer containing 20 mM HEPES pH 7.6, 150 mM NaCl, 1% Triton X-100, 1 mM EDTA and complete protease inhibitor cocktail. SIVA is immunoprecipitated using anti-SIVA or using an antibody against a tag in case that the SIVA is tagged. For example tagged SIVA can be GST-SIVA and the antibody used can be specific for GST as in the exemplified embodiments below. Next, the antibody is adsorbed to proteinG beads for 4 hours at 4° C. Immunoprecipitates are subjected to Western blotting with specific antibodies for example an anti-ubiquitin antibody. The ubiquitin in the method may employ a mutant ubiquitin in which all the lysines in the ubiquitin except K48 are mutated to arginine (Boston Biochem) to identify a SIVA polypeptide capable of K48 ubiquitination. Alternatively, the ubiquitin in the method may employ a mutant ubiquitin in which all the lysines in the ubiquitin except K63 are mutated to arginine (Boston Biochem) to identify a SIVA polypeptide capable of K63 ubiquitination like in the case of self ubiquitination.

Ubiquitin linked to SIVA can be detected for example, by Western blot analysis using anti SIVA antibody and detecting the appearance of heavier bands of SIVA and/or by using antibody against ubiquitin. For example, ubiquitin can be HIS or HA tagged. SIVA can be GST or FLAG tagged.

In one method of the invention tagged SIVA polypeptide and/or ubiquitin can be used and detected or immunoprecipitated with antibodies specific for the tag. For example, GST-SIVA2 is incubated with E1 (e.g. 200 ng/50 µl) and E2, Ubc13/Uev1 (e.g. 500 ng/50 µl), and HIS-ubiquitin enzymes in the in vitro ubiquitination assay. After 1 hr at 37° C. samples are immunoprecipitated with anti-GST antibody. Both IP and total lysates are analysed by Western blotting using anti-SIVA, anti ubiquitin or anti HIS.

In a further aspect, the invention provides methods for identifying candidate agents capable of modulating the ubiquitin-related activity of SIVA or a SIVA polypeptide, by carrying out the above method in the presence or absence of a candidate agent, wherein a change in the level of self-ubiquitination of said SIVA polypeptide in the presence of the agent is indicative that the candidate agent is capable of modulating the ubiquitination-related activity of SIVA.

NIK was found according to the present invention to undergo monoubiquitination as well as degradation inducing, K48-, and stabilizing, K63-polyubiquitinations by transient co-expression with the respective ubiquitin mutants. It is quite interesting that a single molecule is displaying all the known types of conjugation with ubiquitin. This variety of ubiquitinations might well be the determinant of functional versatility of NIK. By exploring the role of SIVA in NIK ubiquitination, it was found according to the invention that co-expression of SIVA enhanced both K48 and K63 ubiquitination of NIK. Consistently, in vitro ubiquitination experiments recombinant SIVA2 was found to be a potent ring finger dependent E3 ligase. SIVA2 is a direct and specific E3 ligase of TRAF2.

A SIVA polypeptide having direct or indirect ubiquitination-related activity can be identified according to the invention by a method comprising: (i) contacting polypeptides comprising an ubiquitin, an E1, an E2, a NIK polypeptide, and optionally an E3 in the presence or the absence of a SIVA polypeptide; (ii) measuring the level of ubiquitination of the NIK polypeptide in the presence and in the absence of the SIVA polypeptide; and (iii) comparing the level of ubiquitination of NIK in the presence and in the absence of the SIVA polypeptide, wherein increase in the level of ubiquitination of NIK in the presence of the SIVA polypeptide is indicative that the SIVA polypeptide has direct or indirect ubiquitination-related activity.

For example, in a cell based assay, plasmids encoding NIK, a SIVA polypeptide and HA tagged ubiquitin can be co transfected in cells and anti-NIK immunoprecipitate of lysed cells can be analysed by Western blotting using anti-HA antibodies. In one embodiment, the cells can be Ramos cells expressing retrovirally transduced NIK and treated with CD70. In another embodiment, the cells can be non lymphoid cells such as HEK 293T stably expressing CD27 receptor and NIK which are treated with CD70. The immunoprecipitated NIK of cell lysates can be analysed by Western blotting using anti-ubiquitin antibody to monitor NIK ubiquitination.

Also, a plasmid encoding a SIVA polypeptide can be co-transfected with a NIK plasmid and an ubiquitin encoding plasmid. The SIVA polypeptide can be, for example, SIVA 1-58 or SIVA-C plasmid and the ubiquitin can be a tagged ubiquitin such as HA-ubiquitin. The ubiquitin can be a mutant ubiquitin mutated in a lysine such as K48R or K63R mutant. The amount of plasmid that can be used is about 4 µg, 6 µg and 8 µg for NIK, SIVA and ubiquitin plasmid, respectively. The cells can be HeLa cells. Twenty-four hours post transfection cells are harvested, lysed and immunoprecipitated with anti-NIK antibody. Western blotting can be carried out with anti-HA for detection of ubiquitin conjugates on NIK.

In one of the cell based methods for identification of a SIVA polypeptide having ubiquitination related activity and/or protein degradation activity, NIK can be co-expressed with a SIVA polypeptide and a TRAF2 polypeptide in cells. The amount of plasmid that can be used is about 0.5 µg, 1.5 µg and 3.0 µg for SIVA and 0.5 µg for NIK and TRAF2. Total cell lysates are prepared 30 hrs post transfection and probed with anti-NIK for detection of ubiquitin conjugates on NIK or degradation of NIK.

In one of the cell based methods for identification of a SIVA polypeptide having ubiquitination related activity cells such as HEK 293T cells are transfected with plasmid encoding FLAG-TRAF2, HIS-SIVA2 and ubiquitin. 24 hours post transfection cells are lysed immunoprecipitated and Western blot analysed using specific antibodies to FLAG-TRAF2 are used to detect ubiquitinated TRAF2. TRAF2 ring finger mutant (C34A) can be used instead WT TRAF2 to prevent its self ubiquitination. TRAF2 ring finger mutant retained its ability to bind SIVA2.

In another cell based assay ubiquitinated TRAF2 recruited to the CD27 receptor by stimulation with FLAG-CD70 and overexpression of SIVA and co-immunoprecipitation by anti-FLAG can be used. SIVA2 can be overexpressed by using the TREX system and induction with 1 uM doxycycline before stimulation with CD70.

Cell based assays of ubiquitination induced by SIVA polypeptides may be carried out without exogenous ubiquitin and with any kind of cells including, but not limited to, HeLa cells, HEK 293T cells, and Ramos cells.

In vitro ubiquitination assays can be carried out for example by employing a reaction containing recombinant HIS-ubiquitin, E1, E2 (e.g. Ubc13/Uev1 heterodimer), a recombinant SIVA polypeptide which can be a fusion protein with GST like for example GST-SIVA2 or GST-SIVAC73A, and a recombinant TRAF2 which can be a FLAG tagged TRAF2. The proteins can be in a buffer containing, 30 mM HEPES pH 7.6, 5 mM MgCl2, 2 mM ATP, 0.2 mM DTT, 5 mM Sodium Citrate, 10 mM creatine phosphate, 0.2 µg/ml creatine kinase and 5 µM ubiquitin aldehyde. Anti FLAG or anti TRAF2 can be used to detect modified (ubiquitinated) TRAF2.

SIVA induces cell death in a caspase dependent mitochondrial pathway (Py et al., 2003). Consistent with its suspected role as inducer of apoptosis, SIVA is upregulated in response to UV and oxidative stress in different cell types and is a direct transcriptional target of the tumor suppressors p53 and E2F1 (Fortin et al., 2004). In the process of apoptosis, caspase-8 is known to cleave proteins like NIK and thus suppress NF-κB, which plays a pivotal role in cell survival and proliferation (Foehr et al., 2000). Likewise, high doses of SIVA2 also degraded the co-expressed NIK and this effect was compromised by proteasome inhibition. It was found according to the present invention that SIVA2 also induces K48 ubiquitination of NIK, which was greatly reduced by mutation of the K670 residue in NIK. Together, these observations point to the regulation of NIK by SIVA2 through the classical ubiquitin-proteasome pathway (Glickman and Ciechanover, 2002). Interestingly, both K48 ubiquitination and degradation of NIK in response to SIVA overexpression occurred even in the complete absence of the SIVA2 ring finger region as well as with the catalytically inactive SIVA ring finger mutant suggesting that SIVA may be not a direct E3 of NIK for inducing K48 ubiquitination SIVA may require an accessory E3 protein working in tandem to mediate ubiquitination. SIVA has been shown to bind to another ring finger protein called OSTL. OSTL may be the E3 accessory protein since it contains B-box-like ring finger motif and is postulated to have a role in B cell signaling and survival (Fontanari Krause et al., 2003). Similarly, TRAF3 was also reported as an indirect ubiquitinating enzyme of NIK causing its degradation (Liao et al., 2004). However, it was shown according to the invention that TRAF3 degraded both wild type NIK and the NIK K670A mutant with similar effectiveness indicating that the molecular mechanisms involved in SIVA2 and TRAF3 mediated NIK degradation differ. SIVA2 and TRAF3 may co-operatively function to ubiquitinate NIK.

Surprisingly, it was found according to the invention while assessing the ability of TRAF3 to impose NIK degradation that NIK modulates TRAF3 affecting its cellular levels, ubiquitination and rate of degradation. This modulation of TRAF3 was peculiar in the sense that it did not result in full degradation of TRAF3, but rather in accumulation of a distinct low molecular weight form of TRAF3 (dTRAF3). Interestingly SIVA2, yet not SIVA1, greatly augmented this NIK-induced cleavage of TRAF3. This is the first observation demonstrating a functional difference between the two splice variants of SIVA. Though direct binding of SIVA2 and TRAF3 occurred only feebly, presence of wild type or kinase dead NIK greatly stabilized their interaction. As in the case of p100-NIK-IKK1 complex where the binding is not influenced by the kinase function of NIK (Xiao et al., 2004), here also NIK appears to play the role of an adaptor protein linking TRAF3 and SIVA2. This is the first time that the formation of NIK-SIVA2-TRAF3 complex, TRAF3 cleavage and ubiquitination co-operatively by NIK and SIVA2 was observed.

Exploring further the type of TRAF3 ubiquitination by co-expression of ubiquitin mutants, it was found according to the invention that TRAF3 predominantly undergoes K63 ubiquitination and that SIVA2 generates dTRAF3 in a K63 ubiqutination dependent manner. Furthermore, ring finger mutation of SIVA2 also blocked generation of dTRAF3. Both NIK induced and SIVA2 induced dTRAF3 formation were blocked by proteasome inhibition and not by lysosome or caspase inhibition. The processing of the D347A mutant TRAF3 (Lee et al., 2001), by SIVA2 and NIK also suggested that this process is caspase independent. This is an important finding suggesting the involvement of K63 ubiquitination in proteasome-dependent processing of TRAF3. SIVA2 may be an E3 for K63 ubiquitination of TRAF3 and NIK may function, as an adaptor or as a kinase, in the processing of TRAF3. These findings show mutual regulation of NIK and TRAF3 co-operatively with SIVA2.

The ring finger of TRAF3, although not contributing to the ubiquitination of TRAF3 by SIVA2 or subsequent generation of dTRAF3, turned out to have major impact on induced alteration of the solubility of the protein. Remarkably, the ring finger mutant TRAF3 was massively ubiquitinated and stayed in the triton insoluble compartment indicating a role for the ring finger in TRAF3 trafficking.

Due that it was found according to the invention that SIVA can induce ubiquitination of TRAF3, it is provided a method for identifying a SIVA polypeptide having direct or indirect ubiquitination-related activity comprising: (i) contacting polypeptides comprising an ubiquitin, an E1, an E2, a TRAF3 polypeptide, and optionally an E3 in the presence or the absence of a SIVA polypeptide; (ii) measuring the level of ubiquitination of the TRAF3 polypeptide in the presence and in the absence of the SIVA polypeptide; and (iii) comparing the level of ubiquitination of TRAF3 in the presence and in the absence of the SIVA polypeptide, wherein increase in the level of ubiquitination of TRAF3 in the presence of the SIVA polypeptide is indicative that the SIVA polypeptide has direct or indirect ubiquitination-related activity. In one embodiment of the invention a NIK polypeptide can be added in step (i).

In one exemplary embodiment of the invention a cell based assay is carried out which uses a TRAF3 plasmid, a NIK plasmid and ubiquitin plasmid co-transfected into cells such as HEK293T cells. The amount of plasmid that can be used is about 3, 4, and 4 μg for TRAF3, NIK and ubiquitin, respectively or the same amount of plasmid of about 4 μg can be used for each protein. Cells are harvested 24 hrs post transfection and total lysates analysed by Western blotting using anti-TRAF3 antibody to see modified TRAF3 forms which represent ubiquitinated TRAF3.

In another exemplary embodiment of the invention, cells are transfected with HIS-TRAF3, FLAG-SIVA2 and HA-Ubiquitin K48R, lysed and anti HIS immunoprecipitate of the lysate is subjected to Western blotting using anti HA antibody. The amount of plasmid used can be 6, 6, and 4 mg/ml of HIS-TRAF3, FLAG-SIVA2 and HA-Ubiquitin, respectively. In one alternative embodiment, the lysate is immunoprecipitated with anti FLAG antibody to precipitate SIVA2 and probed with anti-TRAF3 in Western blots.

In a further aspect, the invention provides methods for identifying candidate agents capable of modulating a direct or indirect ubiquitination-related activity of a SIVA polypeptide on a NIK and/or TRAF3 polypeptide, by carrying out the above method in the presence or absence of a candidate agent, wherein a change in the level ubiquitination of said NIK and/or TRAF3 polypeptide in the presence of the candidate agent is indicative that the candidate agent is capable of modulating the ubiquitination-related activity of SIVA on a NIK and/or TRAF3 polypeptide. The candidate molecule can be a small molecule.

It was found according to the invention, by following the degradation of NIK and NIK K670A by the SIVA ring finger mutant, that the ring finger mutation in SIVA2 nullified the protection of NIK conferred by its lysine 670 mutation resulting in effective degradation of the NIK K670A upon its co-expression with SIVA2 ring finger mutant. One possible explanation is that there exist two opposing types of ubiquitination of NIK, both mediated by SIVA2. In the transient in vivo ubiquitination experiments it has been found according to the invention that SIVA2 promotes both K48 and K63 types of ubiquitination of NIK and that the SIVA2 N-terminus is involved in K48 ubiquitination and degradation of NIK. Linking these two observations, of the K63 ubiquitination of NIK by SIVA2 and not by SIVA2 1-58 and of the ability of mutant SIVA2 ring finger to interfere with the ubiquitination of NIK, it seems quite possible that the ring finger is involved in K63 ubiquitination. Consequently, when NIK K670A and SIVA C73A are expressed together, NIK will have only K48 type of ubiquitination at sites other than lysine 670. In the absence of the stabilizing K63 ubiquitination, the impact of the residual K48 ubiquitination will be prevalent, resulting in effective degradation of NIK. In other words, ring finger mutation in SIVA2 appears to neutralize the protective effect that the NIK K670A mutation has against NIK degradation by SIVA2. Further confirmation of SIVA2-induced K63 ubiquitination of NIK was obtained from the inhibitory effects of mutant Ubc13, a K63 specific E2 (Deng et al., 2000), and CYLD, a K63 specific deubiquitinase (Kovalenko et al., 2003), on NIK-K63 ubiquitination upon co-expression with SIVA2.

Since the in vitro self-K63 ubiquitination of SIVA2 was also blocked by the ring finger mutation, both in vivo and in vitro, K63 ubiquitination seems to be the exclusive function of the ring finger of SIVA2.

SIVA is expressed basally at an extremely low level and one possibility for the weak effects of SIVA suppression might be that SIVA exerts its function only upon upregulation of its level. Pertinently, it has been shown that SIVA is a stress-induced protein and that elevated SIVA levels cause cell death (Fortin et al., 2004; Henke et al., 2000; Padanilam et al., 1998). In line with this, both in constitutive and inducible expression SIVA2 interfered with CD27 and CD40 induced NF-κB activation. This inhibition of the NIK-mediated alternative NF-κB pathway most likely reflects the ability of SIVA2 to cause the degradation of NIK. Based on this, it is tempting to speculate that down regulating the pro-survival role of NIK by SIVA2 contributes to the apoptotic role of the latter in conditions of stress.

SIVA is a minor cellular protein, which is normally expressed at an extremely low level and is able to exert a strong biological effect. NIK appears to play an important role in stabilizing SIVA by directly phosphorylating SIVA. Consistently, kinase inactive NIK failed to stabilize SIVA2 expression. Neither kinase inactive IKK1 or IKK2 failed to interfere with NIK induced SIVA2 phosphorylation in an in vitro kinase assay showing that SIVA2 is a genuine novel NIK substrate. Phosphorylation of many cellular proteins precedes their ubiquitination (Karin and Ben-Neriah, 2000). Phosphorylation by NIK may be a prerequisite for the ubiquitinating function of SIVA2.

It is shown herein a complex regulation of protein modification and degradation mechanisms that, without being bond by the mechanism, can be seen as a programmed fine-tuning system where NIK upon activation, phosphorylates SIVA leading to its stabilization. Later NIK utilizes SIVA for its stabilization-inducing K63 ubiquitination and for cleaving TRAF3, which is an inhibitor of NIK function. Once the cell requires the termination of NIK signaling, SIVA probably binds with a new protein synthesized as a result of NF-κB activation, and forms a K48 ubiquitinating complex effecting NIK degradation. Probably, this act as an auto regulatory loop limiting NIK signaling and, when stress further upregulates SIVA level, it functions to inhibit survival pathways and induce apoptosis. These results indicate that SIVA has dual effect on NIK ubiquitination with opposing consequences. The enhancement of NIK level and thereby its function resulting from co-expression of low doses of SIVA2 could well be a consequence of the suppression of NIK repressors, e.g. TRAF3. Thus, SIVA2 may ubiquitinate and degrade TRAF3 in vivo, resulting in elevation of NIK level.

Identifying the exact location of SIVA action i.e. at the membrane or in the cytoplasm is also crucial to define its exact function. In addition to the CD27 receptor by which SIVA was identified, two other membrane receptors have also been suggested to directly bind to SIVA. One of them is GITR, a TNFR family member expressed mainly in T cells, involved in both apoptosis and NF-κB activation pathways (Spinicelli et al., 2002, Nocentini et al., 2005). CD4 is the third membrane receptor told to bind SIVA and this binding is suggested to modulate apoptosis of CD4+ T cells through a caspase dependent mitochondrial pathway (Petit et al., 2004).

Though SIVA was suggested to bind to TRAF2 binding sites in CD27, GITR and OX40 (Spinicelli et al., 2002), no real-life evidence has been presented in this regard. This, possible, membrane recruitment of SIVA is particularly important by the fact that the bona fide adaptor of NIK, TRAF2, was found herein to degrade NIK in transient expression and SIVA2 protected NIK from TRAF2 induced degradation. Moreover, TRAF2 was suggested recently to act as a negative regulator of the alternative NF-κB pathway (Grech et al., 2004). Since the function of NIK, a TRAF2 interacting protein, is crucial for the alternative NF-κB pathway, speculatively, this novel role of TRAF2 to inhibit alternative pathway could result from NIK degradation induced by TRAF2. Whether SIVA2 plays any role at endogenous level in stabilizing NIK, once it is recruited to the receptor e.g. CD27, through TRAF2, is a fascinating question. In line with this, TRAF2 recruited to the CD27 receptor was found massively ubiquitinated distinguishing it from the TRAF2 recruited to the TNF receptor that does not recruit NIK. The results herein show that SIVA2 but not the mutant SIVA2C73A directly induces TRAF2 K63 ubiquitination. TRAF5 is considered to be a close functional and structural homolog of TRAF2, and they both are implicated in NF-κB activation (Chung et al. 2002). TRAF2 resembles to TRAF6, but to a lesser extent, while differing significantly from TRAF1 and TRAF3.

It was shown according to the invention on in vitro ubiquitination assays performed in a 50 µl reaction volume containing recombinant HIS-ubiquitin-K63 only (a recombinant HIS-ubiquitin where all the lysines in the ubiquitin except K63 are mutated to arginine, Boston Biochem) (8 µg), E1 (0.2 m), E2 (0.5 µg) and 1-2 µg of recombinant GST-SIVA or GST-SIVAC73A with FLAG tagged TRAF2 that. FLAG tagged TRAF2 was transiently expressed and purified using anti FLAG M2 SIVA2 but not the mutant SIVA2C73A directly induces K63 ubiquitination of TRAF2. Constitutively expressing SIVA-C terminus in Ramos cells mimics TRAF2 deficiency in B cells, therefore SIVA-C can be used in diseases associated with excessive TRAF2 activity or expression, or responsible to inhibition of TRAF2. Silencing of SIVA in cells by siRNA can be used in diseases associated with decreased TRAF2 activity or expression, or responsible to enhancement of TRAF2. TRAF2 binds to SIVA2 and binding occurs only when the ring finger is present such as in SIVA2 and SIVA2 1-81. TRAF2 ring finger mutant retained its ability to bind SIVA2. SIVA enhances K48 ubiquitination of TRAF2 in HEK 293T as a function of its ring finger.

It was shown according to the invention that SIVA2 regulates ubiquitination of TRAF2 recruited to CD27 receptor in Ramos cells. The effect of silencing of SIVA in TRAF2 ubiquitination recruited to the CD27 receptor was explored. For this purpose, 293-CD27 cells were transfected with pSUPER SIVA. 48 hours later, cells were treated with FLAG-CD70 to induce recruitment of TRAF2 to the CD27 receptor. Cells were lysed and the CD27 receptor complex was immunoprecipitated using anti-FLAG antibody. Receptor associated TRAF2 was probed with anti-TRAF2 antibody. pSUPER SIVA transfected cells were compared to control pSUPER transfected cells for the level of TRAF2 in the cytoplasm following CD70 stimulation. CD70 triggering resulted in degradation of TRAF2 in a SIVA dependent manner.

Thus, in another aspect, the invention relates to a method for identifying a SIVA polypeptide capable inducing ubiquitination-related activity on a TRAF2, TRAF5 or TRAF6 polypeptide comprising: (i) contacting polypeptides comprising an ubiquitin, an E1, an E2, and a SIVA polypeptide with a TRAF2, TRAF5 or TRAF6 polypeptide; (ii) and detecting whether said ubiquitin binds to said TRAF2, TRAF5 or TRAF6 polypeptide wherein detection of ubiquitin linked to said TRAF2, TRAF5 or TRAF6 polypeptide is indicative that said SIVA polypeptide has ubiquitination-related activity.

In one embodiment of the invention the following reaction is prepared. The reaction contains recombinant HIS-ubiquitin or HIS-ubiquitin-K63 only, E1, E2 (Ubc13/Uev1 heterodimer) (both E1 an E2 were purchased from Boston Biochem) and a recombinant GST-SIVA or GST-SIVA polypeptide or mutant, with FLAG tagged TRAF2 in a buffer containing, 30 mM HEPES pH 7.6, 5 mM MgCl2, 2 mM ATP, 0.2 mM DTT, 5 mM Sodium Citrate, 10 mM creatine phosphate, 0.2 µg/ml creatine kinase and 5 µM ubiquitin aldehyde. FLAG tagged TRAF2 can be prepared by transfecting pcFLAG TRAF2 into HEK 293T cells. About 24 hours post transfection cells are lysed in 1% Trition X100 containing lysis buffer and immunoprecipitated using anti FLAG M2 beads (Sigma). Immunoprecipitated TRAF2 is eluted with FLAG peptide and concentrated using microcon column (MWCO3000) and used in the in vitro ubiquitination reaction. Reactions are incubated at 30° C. for 1 hour. TRAF2 is immunoprecipitated using anti-FLAG M2 beads for 4 hours at 4° C. Immunoprecipitates are subjected to Western blotting with anti TRAF2 (H249, Santacruz) antibody.

In a further aspect, the invention provides methods for identifying candidate agents capable of modulating a ubiquitination-related activity of a SIVA polypeptide on a TRAF2 polypeptide, by carrying out the above method in the presence or absence of a candidate agent, wherein a change in the level ubiquitination of said TRAF2 polypeptide in the presence of the candidate agent is indicative that the candidate agent is capable of modulating the ubiquitination-related activity of SIVA on the TRAF2 polypeptide. The candidate molecule can be a small molecule.

Interestingly, SIVA proteins possess a unique box-B-like ring finger lacking any His residues (CSS-CVRAVDGKAVCGQCERALCGQCVRTCWGC, SEQ ID NO: 6) and has a zinc finger in their C-terminus (Prasad et al. 1997). The amino-terminal ring finger and the carboxy-terminal coiled-coil domain structures, which are characteristic of other B-box-containing proteins are absent in SIVA. Instead, the box-B-like ring finger of SIVA has a Cys-rich region in the carboxyl terminus. It was our finding (reached by two-hybrid screening) that the zinc/ring finger region of SIVA binds to the NIK C-terminus, which has initially directed our attention to the possible involvement of NIK in CD27 signaling. So far, no function has been ascribed to the box-B-like ring finger of SIVA and it is quite surprising that in this decade when ubiquitin research pioneers the signaling field, the potent ring finger 'E3 ligase' activity, which was found according to the present invention to be associated with the box-B-like ring finger of SIVA, was overlooked.

Thus in another aspect, the invention relates to a method for testing or identifying a ubiquitination-related activity of a polypeptide harbouring a B-box-like ring of SEQ ID NO:6 or a homolog thereof comprising: (i) contacting polypeptides comprising an ubiquitin, an E1, and an E2, a polypeptide harbouring a B-box-like ring of SEQ ID NO:6 or a homolog thereof and optionally TRAF2; (ii) and detecting whether said ubiquitin links to said polypeptide harbouring a B-box-like ring or to TRAF2, wherein detection of ubiquitin linked to said polypeptide harbouring a B-box-like ring or to TRAF2 is indicative that said polypeptide harbouring a B-box-like ring has ubiquitination-related activity.

Two or more structures are said to be homologous if they are alike because of shared ancestry. Homology among proteins and DNA is often concluded on the basis of sequence similarity, especially in bioinformatics. For example, in general, if two genes have an almost identical DNA sequence, it is likely that they are homologous. Many algorithms exist to cluster protein sequences into sequence families, which are sets of mutually homologous sequences. Homology of sequences can be of two types: orthologous or paralogous.

Two similar genes in two different species that originated from a common ancestor are orthologous. Homologous sequences are orthologous if they were separated by a speciation event: if a gene exists in a species, and that species diverges into two species, then the divergent copies of this gene in the resulting species are orthologous. A second definition of orthologous describes any two genes in two different species with very similar functions. Homologous sequences are paralogous if they were separated by a gene duplication event: if a gene in an organism is duplicated to occupy two different positions in the same genome, then the two copies are paralogous. The genes encoding myoglobin and hemoglobin are considered to be ancient paralogs.

In a further aspect, the invention provides methods for identifying candidate agents capable of modulating ubiquitination-related activity of a polypeptide harbouring a B-box-like ring of SEQ ID NO:6 or a homolog thereof on a said polypeptide or on a TRAF2 polypeptide, by carrying out the above method in the presence or absence of a candidate agent, wherein a change in the level ubiquitination of said polypeptide harbouring a B-box like ring or of a TRAF2 polypeptide in the presence of the candidate agent is indicative that the candidate agent is capable of modulating the ubiquitination-related activity of a polypeptide harbouring a B-box-like ring of SEQ ID NO:6 or a homolog thereof. The candidate molecule can be a small molecule.

Examples of polypeptides harbouring a B-box-like ring of SEQ ID NO: 6 or a homolog thereof include polypeptides having a B-box ring finger motif lacking HIS.

In one embodiment of the invention, the polypeptide harbouring a B-box-like ring is a SIVA polypeptide.

Ubiquitinated proteins or polypeptides can be detected by Western blots as exemplified in the present invention or by any other assay known in the art.

As mentioned, SIVA is a minor cellular protein, which is normally expressed at an extremely low level and is able to exert a strong biological effect. NIK appears to play an important role in stabilizing SIVA. Likewise, high doses of SIVA2 also degraded the co-expressed NIK and this effect was compromised by proteasome inhibition. It was found according to the present invention that SIVA2 also induces K48 ubiquitination of NIK, which was greatly reduced by mutation of the K670 residue in NIK. Together, these observations point to the regulation of NIK by SIVA2 through the classical ubiquitin-proteasome pathway (Glickman and Ciechanover, 2002). Interestingly, both K48 ubiquitination and degradation of NIK in response to SIVA overexpression occurred even in the complete absence of the SIVA2 ring finger region as well as with the catalytically inactive SIVA ring finger mutant suggesting that SIVA may be not a direct E3 of NIK for inducing K48 ubiquitination. SIVA may require an accessory E3 protein working in tandem to mediate ubiquitination. SIVA has been shown to bind to another ring finger protein called OSTL. OSTL may be the E3 accessory protein since it contains B-box-like ring finger motif and is postulated to have a role in B cell signaling and survival (Fontanari Krause et al., 2003). Similarly, TRAF3 was also reported as an indirect ubiquitinating enzyme of NIK causing its degradation (Liao et al., 2004). However, It was shown according to the invention that TRAF3 degraded both wild type NIK and the NIK K670A mutant with similar effectiveness indicating that the molecular mechanisms involved in SIVA2 and TRAF3 mediated NIK degradation differ. SIVA2 and TRAF3 may co-operatively function to ubiquitinate NIK.

As mentioned, it was found according to the present invention that high concentration of SIVA induces NIK degradation, even in the absence of the c-terminus of SIVA. Also, it was found according to the invention that SIVA2, yet not SIVA1, greatly augmented NIK-induced cleavage of TRAF3. This is the first observation demonstrating a functional difference between the two splice variants of SIVA. Though direct binding of SIVA2 and TRAF3 occurred only feebly, presence of wild type or kinase dead NIK greatly stabilized their interaction. As in the case of p100-NIK-IKK1 complex where the binding is not influenced by the kinase function of NIK (Xiao et al., 2004), here also NIK appears to play the role of an adaptor protein linking TRAF3 and SIVA2. This is the first time that the formation of NIK-SIVA2-TRAF3 complex, TRAF3 cleavage and ubiquitination co-operatively by NIK and SIVA2 was observed.

Thus in another aspect, the invention relates to a method for identifying a SIVA polypeptide capable of inducing protein degradation comprising contacting a SIVA polypeptide with a NIK and/or TRAF3 polypeptide and detecting NIK and/or TRAF3 polypeptide degradation, wherein detection of NIK and/or TRAF3 full or partial degradation is indicative of the capability of said SIVA polypeptide to induce protein degradation.

The method can be carried out in vitro or can be a cell based method. In one exemplary embodiment, the following cell based method is approached. Cells are co transfected with plasmid encoding wild type NIK (0.5 µg plasmid) or NIK K670A mutant and with increasing concentration of SIVA2 encoding plasmid (e.g. 1.0, 2.0 and 3.0 µg plasmid) and/or with TRAF3 encoding plasmid. After transfection the cells are lysed and degradation of NIK, and/or TRAF3 is detected by Western blot analysis using specific antibody. Actin can be used as loading control.

In a further aspect, the invention provides methods for identifying candidate agents capable of modulating the capability of said SIVA polypeptide to induce protein degradation, by carrying out the above method in the presence or absence of a candidate agent, wherein a change in the level of NIK and/or TRAF3 full or partial degradation in the presence of the candidate agent is indicative that the candidate agent is capable of modulating NIK and/or TRAF3 full or partial degradation by SIVA. The candidate molecule can be a small molecule.

In another aspect, the invention relates to identification of an agent capable of modulating the association of the complex between NIK, TRAF3 and a SIVA polypeptide comprising forming a complex of NIK, TRAF3 and a SIVA in the presence or in the absence of a candidate agent and detecting of the ability of the candidate molecule to modulate NIK, TRAF2 and a SIVA polypeptide association, wherein a candidate molecule capable of altering the complex formation is an agent capable of modulating the association of NIK, TRAF3 and SIVA. For example, cells may be transfected with each of the plasmid encoding a SIVA polypeptide and a TRAF polypeptide with and without a NIK polypeptide and incubated in the presence or the absence of a test agent. 24 hrs post transfection total lysates can be immunoprecipitated by an antibody which precipitates SIVA and the immunoprecipitates can be proved in Western blot with anti TRAF-3. A test agent capable of inhibiting or inducing co-precipitation of TRAF-2 mediated by SIVA and NIK is an agent that modulates the formation of said NIK-SIVA2-TRAF3 complex. The agent can increase or decrease the level of the NIK-TRAF3-SIVA complex.

In a further aspect, the invention provides a tripartite complex comprising NIK, TRAF3 and a SIVA.

It was shown according to the invention a complex regulation of protein modification and degradation mechanisms that, without being bound by the mechanism, can be seen as a programmed fine-tuning system where NIK upon activation, lead to SIVA stabilization. Later NIK utilizes SIVA for its stabilization-inducing K63 ubiquitination and for cleaving TRAF3, which is an inhibitor of NIK function. Once the cell requires the termination of NIK signaling, SIVA probably binds with a new protein synthesized as a result of NF-κB activation, and forms a K48 ubiquitinating complex effecting NIK degradation. Probably, this act as an auto regulatory loop limiting NIK signaling and, when stress further upregulates SIVA level, it functions to inhibit survival pathways and induce apoptosis. These results indicate that SIVA has dual effect on NIK ubiquitination with opposing consequences. The enhancement of NIK level and thereby its function resulting from co-expression of low doses of SIVA2 could well be a consequence of the suppression of NIK repressors, e.g. TRAF3. Thus, SIVA2 may ubiquitinate and degrade TRAF3 in vivo, resulting in elevation of NIK level.

Identifying the exact location of SIVA action i.e. at the membrane or in the cytoplasm is also crucial to define its exact function. In addition to the CD27 receptor by which SIVA was identified, two other membrane receptors have also have been suggested to directly bind to SIVA. One of them is GITR, a TNFR family member expressed mainly in T cells, involved in both apoptosis and NF-κB activation pathways (Spinicelli et al., 2002, Nocentini et al., 2005). CD4 is the third membrane receptor told to bind SIVA and this binding is suggested to modulate apoptosis of CD4+ T cells through a caspase dependent mitochondrial pathway (Petit et al., 2004).

Based on the findings according to the invention the favourite candidates to be the substrates of SIVA are NIK, TRAF2, TRAF3 and possibly TRAF5 and TRAF6. The unregulated activity of SIVA, NIK, TRAF2, and TRAF3 are associated with certain disease, disorders or conditions such as in the pathology of viral infection (TRAF2&3, NIK, SIVA), side effects of chemotherapy (SIVA), side effects of ischemia reperfusion (SIVA), situations associated with upregulation of SIVA, autoimmune diseases associated with activation of the alternative NF-κB pathway in a way that depends on NIK (TRAF2&3, SIVA), and diseases associated with unregulated lymphocyte activity (NIK, SIVA, TRAF2&3). For example, TRAF2 upregulation/activation is associated with excessive immune activation and inflammation. NIK upregulation/activation is associated with autoimmune conditions and cancer. TRAF3 upregulation/activation is associated perhaps with immune deficiency. SIVA upregulation/activation is associated with chemo- and radiotherapy side effects and with ischemia and ischemic reperfusion. Thus, modulation, namely activation or inhibition of the ubiquitinating-related or degradation-related activity of a SIVA polypeptide or of a polypeptide harbouring a B-box-like ring of SEQ ID NO: 6 or a homolog thereof may be beneficial for treating or preventing said disease, condition or disorder.

Thus, in one aspect the invention provides the use of an agent capable of modulating the direct or indirect ubiquitination related activity of a polypeptide harboring a B box like ring of the sequence in SEQ ID NO: 6 or a homolog sequence thereof, such as SIVA, in the manufacture of a medicament for treatment or prevention of a disease, disorder or condition whose pathology or course is associated with the activity and/or levels of TRAF2, NIK, TRAF3 and/or SIVA.

The invention provides specific methods for identifying candidate agents capable of modulating the ubiquitin-related activity of SIVA, a SIVA polypeptide or of a polypeptide harbouring a B-box-like ring of SEQ ID NO: 6 or a homolog thereof.

Examples of test agents or candidate agents that can be screened in the methods of the invention include, but are not limited to, small organic molecules, peptides (e.g. antibodies), nucleic acids, and molecules from natural extracts, carbohydrates or any other substance. Test agents include synthetic organic compounds created e.g. by combinatorial chemistry. The compounds tested may be obtained not only through combinatorial chemistry, but also by other high throughput synthesis methods. Automated techniques enable the rapid synthesis of libraries of molecules, large collections of discrete compounds, which can be screened. Producing larger and more diverse compound libraries increases the likelihood of discovering a useful drug within the library. For high throughput screening robots can be used to test inhibition or activation of SIVA mediated ubiquitination and/or protein degradation by thousands of compounds.

It was shown according to the invention that Ramos cells constitutively expressing SIVA-C terminus mimics TRAF2 deficiency in B cells. TRAF2 deficient B cells display high level of p52 (constitutive alternative NF-κB) and TRAF3 (Grech et al., 2004). Similarly, it was found according to the invention that Ramos cells which were engineered to stably express SIVA C terminus show high level of p52 as well as TRAF3 and decreased expression of TRAF2. The hyper NF-κB activation resulting from SIVAc expression may result in enhanced expression of NF-κB dependent immunomediators from cells.

Thus, the invention provides the use of a SIVA polypeptide such as SIVAc, SIVA 1-58, SIVA 1-81 and SIVA2C73A or an agent capable of modulating the ubiquitin related or protein degradation related activity of SIVA in the manufacture of a medicament for treating a disease, disorder or condition by or trough modulation of the immune system.

It was found according to the present invention that SIVA2 also induces K48 ubiquitination of NIK, which was greatly reduced by mutation of the K670 residue in NIK. Thus, such mutant of NIK can be used in the manufacture of a medicament for treating a disease, disorder or condition responsive to modulation of the immune system.

The invention also provides the use of an agent capable of modulating the formation of the NIK-SIVA-TRAF3 complex, in the manufacture of a medicament for the treatment of an immune disease disorder or condition and/or a disease disorder or condition whose pathology or course is associated with excessive NF-κB expression or activity and/or a disease disorder or condition whose pathology or course is associated with excessive activity of NIK such as inflammation or cancer.

In another aspect, the invention provides isolated polypeptides such as an isolated polypeptide comprising a C-terminal fragment of a SIVA polypeptide including the B-box-like ring finger and/or the Zinc finger motifs except for SIVA1 and SIVA2. The invention provides isolated polypeptides such as amino acid residues 58 to 110 of SIVA2 set forth in SEQ ID NO: 3; an N-terminal fragment of a SIVA polypeptide lacking the Zn finger motif 1-81 (SEQ ID NO: 5); a polypeptide comprising an N-terminal fragment of a SIVA; a polypeptide lacking the Zn finger motif and the B-box-like ring finger motif of SIVA2 1-58 (SEQ ID NO: 4); a polypeptide consisting of SEQ ID NO: 4, SEQ ID NO: 5; a polypeptide comprising a SIVA polypeptide mutated at a cysteine residue located at the ring finger motif; a NIK mutant on the lysine residue 670, or a fragment thereof.

As used herein the term "muteins" refers to analogs of a protein, in which one or more of the amino acid residues of the naturally occurring components of the protein are replaced by different amino acid residues, or are deleted, or one or more amino acid residues are added to the original sequence of the protein, without changing considerably the activity of the resulting products as compared with the original protein. These muteins are prepared by known synthesis and/or by site-directed mutagenesis techniques, or any other known technique suitable therefore.

Muteins in accordance with the present invention include proteins encoded by a nucleic acid, such as DNA or RNA, which hybridizes to DNA or RNA, which encodes the protein, in accordance with the present invention, under stringent conditions. The term "stringent conditions" refers to hybridization and subsequent washing conditions, which those of ordinary skill in the art conventionally refer to as "stringent". See Ausubel et al., Current Protocols in Molecular Biology, supra, Interscience, N.Y., §§6.3 and 6.4 (1987, 1992), and Sambrook et al. (Sambrook, J. C., Fritsch, E. F., and Maniatis, T. (1989) Molecular Cloning: A Laboratory Manual, Cold Spring Harbor Laboratory Press, Cold Spring Harbor, N.Y.).

Without limitation, examples of stringent conditions include washing conditions 12° 20-° C. below the calculated Tm of the hybrid under study in, e.g., 2×SSC and 0.5% SDS for 5 minutes, 2×SSC and 0.1% SDS for 15 minutes; 0.1×SSC and 0.5% SDS at 37° C. for 30-60 minutes and then, a 0.1× SSC and 0.5% SDS at 68° C. for 30-60 minutes. Those of ordinary skill in this art understand that stringency conditions also depend on the length of the DNA sequences, oligonucleotide probes (such as 10-40 bases) or mixed oligonucleotide probes. If mixed probes are used, it is preferable to use tetramethyl ammonium chloride (TMAC) instead of SSC. See Ausubel, supra.

Any such mutein preferably has a sequence of amino acids sufficiently duplicative of that of SIVA, such as to have substantially similar, or even better, activity as SIVA. For example, one activity of SIVA is the capability of inducing self or TRAF2 ubiquitination. Assays for measuring SIVA and TRAF2 ubiquitination, are described in the examples below. Another activity of SIVA is to induce directly or indirectly ubiquitination of NIK or TRAF3 described in the examples below. A further activity of SIVA is to induce protein degradation, such as degradation of NIK and/or TRAF3 (full or partial) as described in the examples below. As long as the mutein is capable to have substantial activity, such as one of the mentioned activities of SIVA, it can be considered to have substantially similar activity to SIVA. Thus, it can be determined whether any given mutein has at least substantially the same activity as the SIVA of the present invention by means of routine experimentation as shown for SIVA in the examples below.

In a preferred embodiment, any such mutein has at least 40% identity or homology with the amino acid sequence of SIVA. More preferably, it has at least 50%, at least 60%, at least 70%, at least 80% or, most preferably, at least 90% identity or homology thereto.

Identity reflects a relationship between two or more polypeptide sequences or two or more polynucleotide sequences, determined by comparing the sequences. In general, identity refers to an exact nucleotide to nucleotide or amino cid to amino acid correspondence of the two polynucleotides or two polypeptide sequences, respectively, over the length of the sequences being compared.

For sequences where there is not an exact correspondence, a "percent identity" may be determined. In general, the two sequences to be compared are aligned to give a maximum correlation between the sequences. This may include inserting "gaps" in either one or both sequences, to enhance the degree of alignment. A percent identity may be determined over the whole length of each of the sequences being compared (so-called global alignment), that is particularly suitable for sequences of the same or very similar length, or over shorter, defined lengths (so-called local alignment), that is more suitable for sequences of unequal length.

Methods for comparing the identity and homology of two or more sequences are well known in the art. Thus for instance, programs available in the Wisconsin Sequence Analysis Package, version 9.1 (Devereux J et al 1984, Nucleic Acids Res. 1984 Jan. 11; 12(1 Pt 1):387-95.), for example the programs BESTFIT and GAP, may be used to determine the % identity between two polynucleotides and the % identity and the % homology between two polypeptide sequences. BESTFIT uses the "local homology" algorithm of Smith and Waterman (J Theor Biol. 1981 Jul. 21; 91(2):379-80 and J Mol Biol. 1981 Mar. 25; 147(1):195-7. 1981) and finds the best single region of similarity between two sequences. Other programs for determining identity and/or similarity between sequences are also known in the art, for instance the BLAST family of programs (Altschul S F et al, 1990 J Mol Biol. 1990 Oct. 5; 215(3): 403-10, Proc Natl Acad Sci USA. 1990 July; 87(14): 5509-13, Altschul S F et al, Nucleic Acids Res. 1997 Sep. 1; 25(17): 3389-402) and FASTA (Pearson W R, Methods Enzymol. 1990; 183: 63-98. Pearson J Mol Biol. 1998 Feb. 13; 276(1): 71-84).

Muteins of SIVA, which can be used in accordance with the present invention, include a finite set of substantially corresponding sequences as substitution peptides or polynucleotides which can be routinely obtained by one of ordinary skill in the art, without undue experimentation, based on the teachings and guidance presented herein.

Preferred changes for muteins in accordance with the present invention are what are known as "conservative" substitutions. Conservative amino acid substitutions of SIVA may include synonymous amino acids within a group which have sufficiently similar physicochemical properties that substitution between members of the group will preserve the biological function of the molecule (Grantham Science. 1974 Sep. 6; 185(4154): 862-4). It is clear that insertions and deletions of amino acids may also be made in the above-defined sequences without altering their function, particularly if the insertions or deletions only involve a few amino acids, e.g., under thirty, and preferably under ten, and do not remove or displace amino acids which are critical to a functional conformation, e.g., cysteine residues. Proteins and muteins produced by such deletions and/or insertions come within the purview of the present invention.

Examples of production of amino acid substitutions in proteins which can be used for obtaining muteins of SIVA, for use in the present invention include any known method steps, such as presented in U.S. Pat. Nos. 4,959,314, 4,588,585 and 4,737,462, to Mark et al; U.S. Pat. No. 5,116,943 to Koths et al., U.S. Pat. No. 4,965,195 to Namen et al; U.S. Pat. No. 4,879,111 to Chong et al; and U.S. Pat. No. 5,017,691 to Lee et al; and lysine substituted proteins presented in U.S. Pat. No. 4,904,584 (Shaw et al).

In one embodiment of the invention, the SIVA mutein is one mutated at a cysteine residue located at the B-box like ring finger of SIVA, preferably at cysteine residue 73 of SIVA2.

"Functional derivatives" as used herein cover derivatives of SIVA, and their muteins, which may be prepared from the functional groups which occur as side chains on the residues or are additions to the N- or C-terminal groups, by means known in the art, and are included in the invention as long as they remain pharmaceutically acceptable, i.e. they do not destroy the activity of the protein which is substantially similar to the activity of SIVA.

"Functional derivatives" also comprise multimers made up of SIVA in which changes have been introduced in the sequence of the amino acids making up the SIVA by any conventional method. These changes may comprise elongation or truncation of SIVA molecule or deletion or replacement of one or more amino acids of the SIVA. It is understood that none of the above changes may affect the ubiquinating and/or degradation properties of SIVA.

These derivatives may, for example, include polyethylene glycol side-chains, which may mask antigenic sites and extend the residence of SIVA in body fluids. Other derivatives include aliphatic esters of the carboxyl groups, amides of the carboxyl groups by reaction with ammonia or with primary or secondary amines, N-acyl derivatives of free amino groups of the amino acid residues formed with acyl moieties (e.g. alkanoyl or carboxylic aroyl groups) or O-acyl derivatives of free hydroxyl groups (for example that of seryl or threonyl residues) formed with acyl moieties.

An "active fraction" according to the present invention may e.g. be a fragment of SIVA. The term fragment refers to any subset of the molecule, that is, a shorter peptide that retains the desired biological activity of SIVA8. Fragments may readily be prepared by removing amino acids from either end of SIVA and testing the resultant fragment for its activity in macrophages and/or in the model of local inflammation. Proteases for removing one amino acid at a time from either the N-terminal or the C-terminal of a polypeptide are known, and so determining fragments, which retain the desired biological activity, involves only routine experimentation.

In one embodiment of the invention, the SIVA active fraction is one corresponding to a C-terminal fragment of a SIVA polypeptide including the B-box like ring finger and/or the Zinc finger motif, such as fragments of sIVA2 consisting of residues 58 to 110 (SEQ ID NO: 3). In another embodiment, the SIVA active fraction is one corresponding to an N-terminal fragment of SIVA lacking the Zn finger motif, the B-box-like ring finger or both, such as fragments the fragments of SIVA from residues 1-58 (SEQ ID NO: 4) or from residues 1-81 (SEQ ID NO: 5).

As active fractions of SIVA, muteins and fused proteins thereof, the present invention further covers any fragment or precursors of the polypeptide chain of the protein molecule alone or together with associated molecules or residues linked thereto, e.g., sugar or phosphate residues, or aggregates of the protein molecule or the sugar residues by themselves, provided said fraction has substantially similar activity to SIVA.

The term "fused protein" refers to a polypeptide comprising a SIVA, or a mutein or fragment thereof, fused with another protein, which, e.g., has an extended residence time in body fluids. A SIVA may thus be fused to e.g., an immunoglobulin or a fragment thereof.

"Isoforms" of SIVA are proteins capable of having SIVA activity or fragment thereof, which may be produced by alternative splicing.

The term "circularly permuted derivatives" as used herein refers to a linear molecule in which the termini have been joined together, either directly or through a linker, to produce a circular molecule, and then the circular molecule is opened at another location to produce a new linear molecule with termini different from the termini in the original molecule. Circular permutations include those molecules whose structure is equivalent to a molecule that has been circularized and then opened. Thus, a circularly permuted molecule may be synthesized de novo as a linear molecule and never go through a circularization and opening step. The preparation of circularly permutated derivatives is described in WO95/27732.

In another aspect, the invention provides isolated polynucleotides, such as those set forth in SEQ ID NO: 7 SEQ ID NO: 8 or SEQ ID NO: 9, which encode polypeptides according to the invention.

Expression of a polypeptide of the invention in a mammalian cell may be approached by inserting the DNA coding for the peptide into a vector comprising a promoter, optionally an intron sequence and splicing donor/acceptor signals, and further optionally comprising a termination sequence. These techniques are in general described in Ausubel et al., Current Protocols in Molecular Biology (Chapter 16), Greene Publications and Wiley Interscience, New York, N.Y., 1987-1995; Sambrook et al., Molecular Cloning: A Laboratory Manual, Cold Spring Harbor Laboratory, Cold Spring Harbor, N.Y., 1989.

The above promoter, intron, and termination sequences are operable in mammalian cells. The promoter is preferably a strong promoter such as the above-noted RSV, CMV, or MPSV promoter. The promoter may also be the SV40 early promoter (Everett, et al. 1983, and references therein), or a cellular promoter, such as the beta-actin promoter or the ELF-1 promoter (Tokushige, et al., 1997). Also, a hybrid promoter may be used, such as the hybrid between the lac operator and the human ELF-1 alpha promoter as described by Edamatsu et al. 1997, the CMV-beta actin hybrid promoter described by Akagi et al (1997), or the hybrid between the operator sequences and the CMV promoter (Furth et al., 1994, and references therein).

Intron sequences, which may be inserted as complete sequences, i.e., including the splice donor and acceptor sites, may be inserted into the coding sequence of the polypeptide, which it is desired to express. Insertion if such intron sequences may enhance RNA stability and thus enhance production of the desired polypeptide. While in principle, suitable intron sequences may be selected from any gene containing introns, exemplary intron sequences are the beta-actin intron, the SV 40 intron, and the p55 TNF receptor intron.

The intron sequence may contain enhancer elements, which may enhance transcription from the above-noted promoters.

Often, intron sequences also contain transcriptional or translational control sequences that confer tissue specific expression. Therefore, when it is desired to express a polypeptide of the invention in a tissue-specific manner, such intron sequences may be advantageously employed. An example of an intron containing tissue-specific enhancer elements is the erythroid-specific enhancer located in intron 8 of the human 5-aminolevulinate synthase 2 gene (Surinya et al. 1998), and a discussion of the principle of enhancing protein production using intron sequences, together with example intron sequences, is provided in Huang et al. 1990.

Transcriptional termination sequences and polyadenylation signals may be added at the 3' end of the DNA coding for the polypeptide that it is desired to express. Such sequences may be found in many or even most genes. Advantageously, the SV 40 polyadenylation signal can be used (Schek et al., 1992, and references therein).

Vectors for expression of polypeptides of invention in a mammalian cell could be used for example the pcDNA3.1 vector (Invitrogen), which contains the CMV promoter for driving expression of the gene encoding the desired polypeptide and pMPSVEH vectors with the MPSV promoters.

Recombinant polypeptides can be produced either in bacterial or eukaryotic (e.g. CHO) cultured host cells transfected with vectors encoding such polypeptides or in transgenic animals. When using transgenic animals it is particularly advantageous to produce heterologous polypeptides in their milk. Dairy animals such as cattle, sheep and goats are thus exemplary hosts. See, for example, patent specifications WO 88/00239, WO 90/05188, WO 91/02318, and WO 92/11757; and U.S. Pat. Nos. 4,873,191; 4,873,316; and 5,304,489, which are incorporated herein by reference in their entirety.

The polypeptides may comprise half-life extending moieties such as a high molecular weight polymer resulting in "fusion polypeptides or proteins" with extended half-life in body fluids. For example, polypeptides according to the invention can be fused to a protein such as, for example, an immunoglobulin or to a high molecular weight polymer, such as polyethylene glycol (PEG), or the like.

The invention pertains to a polypeptide according to the invention as defined above, or to a salt thereof and/or derivative thereof and/or a fusion polypeptide thereof.

The term "salts" herein refers to both salts of carboxyl groups and to acid addition salts of amino groups of the peptides of the invention. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids such as, for example, hydrochloric acid or sulfuric acid, and salts with organic acids such as, for example, acetic acid or oxalic acid. Of course, any such salts must have substantially similar activity to the peptide of the invention.

The present invention also provides expression vectors comprising the DNA sequence encoding a polypeptide of the invention and methods for their production by introducing said vector in prokaryotic or eukaryotic host cells, such as insect cells, yeast cells, or mammalian cell such as HeLa, HEK 293T and CHO cells, growing the cells and isolating the protein produced.

Moreover, the invention provides a viral vector encoding a polypeptide.

In another aspect, the invention provides a pharmaceutical composition comprising an agent capable of modulating the ubiquitin related activity of a polypeptide harbouring a B-box-like ring of sequence of SEQ ID NO: 6 or a homolog sequence thereof, and a pharmaceutically acceptable carrier.

In a further aspect, the invention provides a pharmaceutical composition comprising an agent capable of modulating the protein degradation mediated by the activity of a polypeptide harbouring a B-box-like ring of sequence of SEQ ID NO: 6 or a homolog sequence thereof, and a pharmaceutically acceptable carrier.

It has been shown according to the invention that the C-terminal fragment of SIVA, such as the fragment of SIVA spanning residues 58 to 110 (SEQ ID NO: 3), has a dominant negative effect on NIK and CD27 induced NF-κB activation at high concentrations. At low concentrations and in a stable cell line it exhibits enhancing effects on NF-κB activation. Thus, in another further aspect, the invention provides a polypeptide corresponding to the C-terminal fragment of SIVA including the B-box-like ring finger and/or the Zinc finger motifs and a polynucleotide (or DNA) encoding said polypeptide.

Also, it was found according to the invention that the N-terminal fragment of SIVA, such as the fragment of SIVA spanning residues 1 to 58 (SEQ ID NO: 4) or 1 to 81 (SEQ ID NO: 5), like intact SIVA, can induce degradation of NIK. Therefore, another aspect of the invention, relates to a polypeptide corresponding to the N-terminal fragment of a SIVA polypeptide lacking the Zn finger motif the B-box-like ring finger motif or both, and to a polynucleotide (or DNA) encoding said polypeptide.

The invention relates also to polynucleotides encoding the polypeptides of the invention such as those set forth in SEQ ID NO: 7, SEQ ID NO: 8 and SEQ ID NO: 9.

The polypeptides of the invention may be produced, in eukaryotic or eukaryotic expression systems, intra-cellulary, periplasmic or may be secreted into the medium. The produced polypeptides of the invention may be recovered in soluble or insoluble form (inclusion bodies). A vector comprising a polynucleotide encoding the polypeptides of the invention might be used for expression of said polypeptides in prokaryotic or eukaryotic systems. An expression vector encoding an effective signal peptide, such as the human growth hormone signal peptide, fused to the polynucleotide (or DNA) encoding polypeptides of the invention may be used for eukaryotic expression and secretion.

The present invention provides polypeptides of the invention such as those set forth in SEQ ID NO: 3, SEQ ID NO: 4, and SEQ ID NO: 5 or a mutein, fusion protein, functional derivative, circularly permutated derivative or fragment thereof, or salt thereof, or a polynucleotide encoding said polypeptides of the invention, for the manufacture of a medicament for the treatment of a disease disorder or condition. For example, for treatment of a disease disorder or condition associated with SIVA, NIK, TRAF2, and TRAF3 such as the pathology of viral infection, side effects of chemotherapy, side effects of ischemia reperfusion, situations associated with upregulation of SIVA, autoimmune diseases associated with activation of the alternative NF-κB pathway in a way that depends on NIK, and diseases associated with unregulated lymphocyte activity.

A therapeutic or research-associated use of these tools necessitates their introduction into cells of a living organism. For this purpose, it is desired to improve membrane permeability of peptides, polypeptides and polynucleotides.

Derivatization with lipophilic structures may be used in creating peptides and proteins with enhanced membrane permeability. For instance, the sequence of a known membranotropic peptide as noted above may be added to the sequence of the peptide or polypeptide. Further, the peptide or polypeptide may be derivatized by partly lipophilic structures such as the above-noted hydrocarbon chains, which are substituted with at least one polar or charged group. For example, lauroyl derivatives of peptides have been described by Muranishi et al., 1991. Further modifications of peptides and polypeptide comprise the oxidation of methionine residues to thereby create sulfoxide groups, as described by Zacharia et al. 1991. Zacharia and co-workers also describe peptide or derivatives wherein the relatively hydrophobic peptide bond is replaced by its ketomethylene isoester (COCH2). These and other modifications known to the person of skill in the art of protein and peptide chemistry enhance membrane permeability.

Guidance for using lipid-based carriers for intracellular delivery of therapeutic molecules, such polypeptides of the present invention is well known in the art (Abra R M. et al., 2002. J Liposome Res. 12:1-3; Park J W., 2002. Breast Cancer Res.; 4(3):95-9; Bendas G., 2001. BioDrugs 15:215-24; Maruyama K., 2000. Biol Pharm Bull. 23:791-9; Hong K. et al., 1999. Ann N Y Acad Sci. 886:293-6; Margalit R., 1995. Crit Rev Ther Drug Carrier Syst. 12:233-61; Storm G. and Crommelin D J., 1997. Hybridoma 16:119-25; Park J W. et al., 1997. Adv Pharmacol. 40:399-435).

Another way of enhancing membrane permeability is the use receptors, such as virus receptors, on cell surfaces in order to induce cellular uptake of the peptide or protein. This mechanism is used frequently by viruses, which bind specifically to certain cell surface molecules. Upon binding, the cell takes the virus up into its interior. The cell surface molecule is called a virus receptor. For instance, the integrin molecules CAR and AdV have been described as virus receptors for Adenovirus, see Hemmi et al. 1998, and references therein. The CD4, GPR1, GPR15, and STRL33 molecules have been identified as receptors/co-receptors for HIV, see Edinger et al. 1998 and references therein.

Thus, conjugating peptides, polypeptide or polynucleotides to molecules that are known to bind to cell surface receptors will enhance membrane permeability of said peptides, polypeptide or polynucleotides. Examples for suitable groups for forming conjugates are sugars, vitamins, hormones, cytokines, transferrin, asialoglycoprotein, and the like molecules. Low et al., U.S. Pat. No. 5,108,921, describes the use of these molecules for the purpose of enhancing membrane permeability of peptides, polypeptide and polynucleotides, and the preparation of said conjugates.

Low and co-workers further teach that molecules such as folate or biotin may be used to target the conjugate to a multitude of cells in an organism, because of the abundant and unspecific expression of the receptors for these molecules.

The above use of cell surface proteins for enhancing membrane permeability of a peptide, polypeptide or polynucleotide of the invention may also be used in targeting said polypeptide, or polynucleotide of the invention to certain cell types or tissues. For instance, if it is desired to target cancer cells, it is preferable to use a cell surface protein that is expressed more abundantly on the surface of those cells. Examples are the folate receptor, the mucin antigens MUC1, MUC2, MUC3, MUC4, MUC5AC, MUC5B, and MUC7, the glycoprotein antigens KSA, carcinoembryonic antigen, prostate-specific membrane antigen (PSMA), HER-2/neu, and human chorionic gonadotropin-beta. The above-noted Wang et al., 1998, teaches the use of folate to target cancer cells, and Zhang et al. 1998, teaches the relative abundance of each of the other antigens noted above in various types of cancer and in normal cells.

The polypeptide, peptide or polynucleotide of the invention may therefore, using the above-described conjugation techniques, be targeted to certain cell type as desired. For instance, if it is desired to inhibit activation of NIK in cells of the lymphocytic lineage, a polypeptide, peptide or polynucleotide of the invention fragment thereof, mutants and derivatives of the invention may be targeted at such cells, for instance, by using the MHC class II molecules that are expressed on these cells. This may be achieved by coupling an antibody, or the antigen-binding site thereof, directed against the constant region of said MHC class II molecule to the polypeptide or peptide of the invention. Further, numerous cell surface receptors for various cytokines and other cell communication molecules have been described, and many of these molecules are expressed with in more or less tissue- or cell-type restricted fashion. Thus, when it is desired to target a subgroup of T cells, the CD4 T cell surface molecule may be used for producing the conjugate of the invention. CD4-binding molecules are provided by the HIV virus, whose surface antigen gp42 is capable of specifically binding to the CD4 molecule.

The polypeptide and polynucleotide sequences of the invention may be introduced into cells by the use of a viral vector. The use of vaccinia vector for this purpose is detailed in chapter 16 of Current Protocols in Molecular Biology. The use of adenovirus vectors has been described e.g. by Teoh et al., 1998, Narumi et al, 1998, Pederson et al, 1998, Guang-Lin et al., 1998, and references therein, Nishida et al., 1998, Schwarzenberger et al 1998, and Cao et al., 1998. Retroviral transfer of antisense sequences has been described by Daniel et al. 1998.

When using viruses as vectors, the viral surface proteins are generally used to target the virus. As many viruses, such as the above adenovirus, are rather unspecific in their cellular tropism, it may be desirable to impart further specificity by using a cell-type or tissue-specific promoter. Griscelli et al., 1998 teach the use of the ventricle-specific cardiac myosin light chain 2 promoter for heart-specific targeting of a gene whose transfer is mediated by adenovirus.

Alternatively, the viral vector may be engineered to express an additional protein on its surface, or the surface protein of the viral vector may be changed to incorporate a desired peptide sequence. The viral vector may thus be engineered to express one or more additional epitopes, which may be used to target; said viral vector. For instance, cytokine epitopes, MHC class II-binding peptides, or epitopes derived from homing molecules may be used to target the viral vector in accordance with the teaching of the invention.

The present invention encompasses pharmaceutical compositions comprising one or more active substance selected from one or more polypeptides of the invention and/or polynucleotides or vectors harbouring their sequences or antisense. The present invention encompasses pharmaceutical compositions comprising specific antibodies able to recognize and bind in a SIVA polypeptide regions responsible for ubiquitinating SIVA, TRAF2, NIK and TRAF3.

The definition of "pharmaceutically acceptable" is meant to encompass any carrier, which does not interfere with effectiveness of the biological activity of the active ingredient and that is not toxic to the host to which it is administered. For example, for parenteral administration, the active protein(s) may be formulated in a unit dosage form for injection in vehicles such as saline, dextrose solution, serum albumin and Ringer's solution.

The active ingredients of the pharmaceutical composition according to the invention can be administered to an individual in a variety of ways. The routes of administration include intradermal, transdermal (e.g. in slow release formulations), intramuscular, intraperitoneal, intravenous, subcutaneous, oral, intracranial, epidural, topical, and intranasal routes. Any other therapeutically efficacious route of administration can be used, for example absorption through epithelial or endothelial tissues or by gene therapy wherein a DNA molecule encoding the active agent is administered to the patient (e.g. via a vector), which causes the active agent to be expressed and secreted in vivo. In addition, the polypeptide(s) according to the invention can be administered together with other components of biologically active agents such as pharmaceutically acceptable surfactants, excipients, carriers, diluents and vehicles.

The invention relates to the use of specific antibodies able to recognize and bind in a SIVA polypeptide region responsible for SIVA, TRAF2, TRAF3 and NIK ubiquitination, in the manufacture of a medicament for the treatment of a disease.

The invention also relates to a method for the treatment of a disease involving ubiquitination of SIVA, TRAF2, TRAF3, and/or NIK in the pathogenesis of said disease comprising administration of a therapeutically effective amount of specific antibodies able to recognize regions in SIVA responsible for ubiquitination, to a subject in need.

For parenteral (e.g. intravenous, subcutaneous, intramuscular) administration, the active protein(s) can be formulated as a solution, suspension, emulsion or lyophilized powder in association with a pharmaceutically acceptable parenteral vehicle (e.g. water, saline, dextrose solution) and additives that maintain isotonicity (e.g. mannitol) or chemical stability (e.g. preservatives and buffers). The formulation is sterilized by commonly used techniques.

The bioavailability of the active polypeptide(s) according to the invention can also be ameliorated by using conjugation procedures which increase the half-life of the molecule in the human body, for example linking the molecule to polyethylenglycol, as described in the PCT Patent Application WO 92/13095.

A "therapeutically effective amount" is such that when administered, the said polypeptides, polynucleotide or virus of the invention induces a beneficial effect in preventing or the course of a disease. The dosage administered, as single or multiple doses, to an individual may vary depending upon a variety of factors, including the route of administration, patient conditions and characteristics (sex, age, body weight, health, and size), extent of symptoms, concurrent treatments, frequency of treatment and the effect desired. Adjustment and manipulation of established dosage ranges are well within the ability of those skilled in the art.

All references cited herein, including journal articles or abstracts, published or unpublished U.S. or foreign patent application, issued U.S. or foreign patents or any other references, are entirely incorporated by reference herein, including all data, tables, figures and text presented in the cited references. Additionally, the entire contents of the references cited within the references cited herein are also entirely incorporated by reference.

Reference to known method steps, conventional methods steps, known methods or conventional methods is not any way an admission that any aspect, description or embodiment of the present invention is disclosed, taught or suggested in the relevant art.

Having now described the invention, it will be more readily understood by reference to the following examples that are provided by way of illustration and are not intended to be limiting of the present invention.

EXAMPLES

Material and Methods

Reagents: mCD70, hCD40L and hBLyS/BAFF were produced by large-scale transfection of human embryonic kidney (HEK) 293T cells with the relevant expression constructs (see below). TNF, a gift from Dr. G. Adolf, Boehringer Institute, Vienna, Austria, was applied to cells at a concentration of 100 ng/ml. MG132 and Lactacystin were purchased from Calbiochem, and G418 was from Life Technologies, Zeocin from invivogen and Blasticidin, Puromycin and Ponasterone from Invitrogen. Recombinant TRAIL was purchased from Alexis. Recombinant HIS-Ubiquitin K48 only, HIS-Ubiquitin K63 only, human E1, Ubc13-Uev1 heterodimer were obtained from Boston Biochem. Ubiquitin aldehyde was from A.G. Scientific.

Antibodies: Anti-p52 antibody was purchased from Upstate Biotechnologies, antibodies against p65, p52, p50, RelB, TRAF2, IKK1 (M280 & H744), SIVA, TRAF3, NIK (H-248) were from Santa Cruz Biotechnology, anti-HIS, anti-FLAG, anti-FLAG M2-beads, and anti-b actin from Sigma, anti-ubiquitin and anti-GST from Covance, anti-GFP from Roche, anti-κBα from Transduction Laboratories. The anti-NIK monoclonal antibody NIK-81 was raised by immunizing mice with a KLH-coupled peptide corresponding to a sequence within the NIK kinase domain (CRLGRGSFGEV-HRMEDK-amino acids 405-420 SEQ ID NO: 34). Anti-NIK, anti-HA and anti-myc (clone-9E10) monoclonal antibodies were purified from mouse ascitic fluids on affinity columns to which their corresponding peptides were coupled.

The human B lymphoblastoid lines of Burkitt lymphoma origin, Ramos, Raji, and BJAB, were cultured in RPMI medium. All adherent cells HEK293T, HeLa and MEF were cultured in Dulbecco's modified Eagle's medium. Both culture media were supplemented with 10% fetal calf serum, 100 U/ml pencillin, and 100 mg/ml streptomycin.

BJAB cells stably expressing NIK with a C-terminal TAP tag (Rigaut et al., 1999), was created by 1 mg/ml G418 selection of electroporated cells. SIVA2 was introduced into BJAB NIK stable cell line by retroviral transduction followed by selection with 1 mg/ml puromycin. Ramos cells stably expressing NIK N-terminally tagged with myc (myc-NIK), created by nucleofection using Amaxa nucleofector device and selection using 1 mg/ml puromycin. Ramos cells stably expressing HIS-SIVA2 and Ramos mycNIK.

Ecdysone inducible 293 cell lines expressing SIVA2 were created following the manufacturers instructions (Invitrogen) and later, myc NIK and myc NIK K670A were introduced into these cells by retroviral transduction and selection with 1 mg/ml puromycin.

Expression vectors: The cDNAs for the extracellular domains of mCD70, hCD40L, were PCR-amplified from ESTs and cloned in fusion with a modified leucine zipper and FLAG tag (Fanslow et al., 1994), into pcDNA3 (Invitrogen). pCS3MTNIK and pCS3MT-NIK KK429,430AA, expression vectors for wild-type and 'kinase-dead' NIK fused N-terminally to a six myc tag, were obtained from Dr. Michael Kracht, Germany. pEGFP was purchased from Clontech. Human NIK with a mutation (G860R) corresponding to that of the mouse aly mutation (G856R) (Shinkura et al., 1999), and all other point mutations described were generated with a site-directed mutagenesis kit (Stratagene). Ubiquitin plasmid to assess monoubiquitination (Ub KKKK 11,29,48,63 RRRR) was kindly provided by Prof Yosef Yarden, Weizmann Institute of Science, Israel. The proteasome subunit C8, with a C-terminal myc tag was generated by PCR and cloned into pcDNA3 vector (Invitrogen).

NIK-pCS3MTNIK with N-terminal 6 myc tag, aly NIK, Kinase dead NIK, NIK K670A were generated from pCS3MTNIK by site directed mutagenesis using pfu DNA polymerase using the manufacturer's protocol (Stratagene).

A vector for expressing NIK N-terminally fused to the myc tag (EQKLISEEDL, SEQ ID NO: 35) was obtained from Dr. Michael Kracht, Germany.

Yeast two-hybrid screening: The system used for screening was the Matchmaker version III (clontech). The prey was pre-transformed human bone marrow library (cat# HY4053AH) that offers high stringent quadruple drop out (QDO) selection along with a-gal assay. Clones growing on plates without LEU, TRP, HIS and ADE were reconfirmed by a-gal assay, which is much more specific than the usual, often leaky, b-gal assay. Plasmids of the positive clones were prepared as follows. Single clones were inoculated into QDO liquid broth and grown overnight at 37° C. Cells were pelleted at 10,000 g and resuspended in 200 µl of buffer containing 2% Triton X-100, 1% SDS, 100 mM NaCl, 10 mM Tris pH8.0, and 1 mM EDTA. The lysates were vortexed for 2 min after adding 200 µl of phenol: chloroform: isoamyl alcohol (25:24:1) and 0.3 g of 600 microns acid washed glass beads (Sigma). Supernatant was collected by centrifugation at 12,000 g and the DNA was precipitated by sodium acetate/ethanol precipitation method (Sambrook et al., 1989). Encoded inserts from the plasmids were amplified by PCR with the primers specific for the library vector pACT2. For further biochemical analysis of individual clones, the amplicons were directly cloned into the N-terminally HIS tagged mammalian expression vector pcDNA3.1 (Invitrogen).

Expression of recombinant proteins: For bacterial expression of GST fusion proteins, IκBα 1-54, SIVA2 and SIVA2 C73A were cloned into pGEX vector and expressed in BL-21 cells following manufacturer's protocol (GST Gene Fusion System, 3rd ed, Pharmacia Biotech). The induction was done at OD600 of 0.6 with 1 mM IPTG. To avoid the formation of insoluble protein and inclusion bodies, the bacterial culture was grown at 25° C. instead of 37° C.

HIS-NIK 338-947 was expressed baculovirally in insect cells in our lab as described previously.

PCR and RT-PCR: PCRs for site directed mutagenesis and amplifying various cDNAs were performed using Pfu Turbo DNA polymerase following manufacturer's instructions (Stratagene). All the RT-PCRs were carried out using Superscript II following manufacturers protocol (Invitrogen).

Plasmid Transfections, Immunoblotting, and Immunoprecipitations:

Plasmid transfections were performed by one of the following methods:
  a. Calcium phosphate precipitation method (Sambrook et al., 1989).
  b. Amaxa nucleofection (Amaxa biosystems)
  c. Gene porter (Gene therapy systems)
  d. Lipofectamine2000 (Invitrogen)
  e. Regular electroporation was performed as follows—

Cells (10×10⁶/electroporation) were washed once and resuspended in 400 µl serum free medium with 25 µg of the plasmid. Cells mixed with DNA were transferred into 0.4 cm gap cuvette and incubated in ice for 10 min. Electroporation was done at 0.24 KV, 960 µF and the time constant was optimized to 40, in a BIORAD Genepulser. After the pulse, cells were kept in ice for 5 min and later transferred into growth medium.

Immunoblotting and immunoprecipitations were performed as described (Ramakrishnan et al., 2004). Typically, 1.5×10⁶ HEK 293T cells were seeded into 10 cm plates. Following a 24 hr period of incubation the cultures were transfected with respective plasmids while maintaining a total DNA concentration of 15 µg per plate by adding empty vector.

Typically, HEK293T cells were seeded onto 90-mm plates (1.5×10⁶ cells/plate) and transfected using the calcium phosphate precipitation method (Sambrook et al., 1989) a day later using a total amount of 10 µg DNA in 10 ml of DMEM medium with 10% FBS. For co-transfection a 1:1 mixture of the plasmids encoding tested proteins was used. Twenty four hours following transfection the cells were rinsed once with phosphate buffered saline (PBS) and lysed in 1 ml of lysis buffer (10 mM Tris-HCl (pH 7.6), 250 mM NaCl, 1% NP-40, 1 mM EDTA, 1 mM PMSF) which included 1' complete protease inhibitor cocktail (Roche Molecular Biochemicals). Pre-cleared lysates were incubated for 2 hours at 4° C. with 2 µg of anti-myc or anti-HIS antibody preabsorbed to protein-G-Sepharose beads (Amersham biosciences). The beads were then rinsed with lysis buffer, subjected to SDS-PAGE, and the proteins were transferred to a nitrocellulose membrane and probed with the indicated antibodies. The antibodies were visualized with horseradish peroxidase (HRP)-coupled secondary antibodies, using the enhanced chemiluminescence (ECL) Western blotting detection system (Amersham) according to the manufacturer's instructions.

To prepare lysate of cells, typically, cells were harvested 24 hr following transfection then lysed in 1% Triton X-100 lysis buffer [(1% Triton X-100, 150 mM NaCl, 1 mM EDTA, 20 mM Tris-cl (pH 7.6) and 1× complete protease inhibitor (Roche)]. All immunoprecipitations were carried out by incubation for 4 hours at 4° C. with the specific antibodies and protein G sepharose beads (Amersham Pharmacia).

Lysis condition differs where nuclear and cytoplasmic extract are separated (Schreiber et al., 1989).

In vitro kinase assay: Kinase assays of transfected and endogenous proteins were carried out as described (Ramakrishnan et al., 2004).

Luciferase assay: Cells were seeded in 6-well plate (HEK 293T 200000, HeLa 100000, MEF 100000 cells/well). HEK 293T and HeLa cells were transfected by the calcium phosphate precipitation method and MEFs were transfected with a liposome-based reagent (Gene therapy systems). Luciferase cDNA under regulation of the HIV-LTR (human immunodeficiency virus long terminal repeat) NF-κB promoter was used as the reporter plasmid. After 24 hours, cells were lysed in 120 µl of lysis buffer as described (Fred M. Ausubel, 1996), and 10-200 lysate was used for the luciferase assay.

siRNA and lentiviral transduction: Stable and transient expression of siRNA and lentiviral transductions were done as described (Ramakrishnan et al., 2004).

Nucleotide and Amino Acid Sequence of SIVA 1 and SIVA 2 and Fragments:

```
SIVA1-nucleotide sequence (Acc# NM_006427)
                                                              (SEQ ID NO: 10)
atgcccaagcggagctgcccttcgcggacgtggccccgctacagctcaaggtccgcgtgagccagagggagttgagccg cggcgtgtgcgccgagcgctactcgcaggaggtcttcgagaagaccaagcgactcctgttcctcggggcccaggcctacc tggaccacgtgtgggatgaaggctgtgccgtcgttcacctgccagagtccccaaagcctggccctacaggggccccgagg gctgcacgtgggcagatgctgattggaccagacggccgcctgatcaggagccttgggcaggcctccgaagctgacccatc tggggtagcgtccattgcctgttcctcatgcgtgcgagccgtggatgggaaggcggtctgcggtcagtgtgagcgagccc tgtgcgggcagtgtgtgcgcacctgctggggctgcggctccgtggcctgtaccctgtgtggcctcgtggactgcagtgac atgtacgagaaagtgctgtgcaccagctgtgccatgttcgagacctga SIVA2-nucleotide sequence (Acc# NM_021709)
                                                              (SEQ ID NO: 11)
atgcccaagcggagctgcccttcgcggacgtggccccgctacagctcaaggtccgcgtgagccagagggagttgagccg cggcgtgtgcgccgagcgctactcgcaggaggtcttcgaccatctggggtagcgtccattgcctgttcctcatgcgtgc gagccgtggatgggaaggcggtctgcggtcagtgtgagcgagccctgtgcgggcagtgtgtgcgcacctgctgggctg
```

-continued

```
ggctccgtggcctgtaccctgtgtggcctcgtggactgcagtgacatgtacgagaaagtgctgtgcaccagctgtgccat
gttcgagacctgaggctggctca
```

SIVA1-amino acid sequence
(SEQ ID NO: 1)
MPKRSCPFADVAPLQLKVRVSQRELSRGVCAERYSQEVFEKTKRLLFLGAQAYLDHVWDEGCAVVHLPESPKPGPTGAPR

AARGQMLIGPDGRLIRSLGQASEADPSGVASIACSSCVRAVDGKAVCGQCERALCGQCVRTCWGCGSVACTLCGLVDCSD

MYEKVLCTSCAMFET

SIVA2-amino acid sequence
(SEQ ID NO: 2)
MPKRSCPFADVAPLQLKVRVSQRELSRGVCAERYSQEVFDPSGVASIACSSCVRAVDGKAVCGQCERALCGQCVRTCWGC

GSVACTLCGLVDCSDMYEKVLCTSCAMFET

SIVAc-amino acid sequence
(SEQ ID NO: 3)
KAVCGQCERALCGQCVRTCWGCGSVACTLCGLVDCSDMYEKVLCTSCAMFET SIVAc-nucleotide sequence
(SEQ ID NO: 7)
```
aaggcggtctgcggtcagtgtgagcgagccctgtgcgggcagtgtgtgcgcacctgctggggctgcggctccgtggcct
gtaccctgtgtggcctcgtggactgcagtgacatgtacgagaaagtgctgtgcaccagctgtgccatgttcgagacc
```

SIVA2 1-58 amino acid sequence
(SEQ ID NO: 4)
MPKRSCPFADVAPLQLKVRVSQRELSRGVCAERYSQEVFDPSGVASIACSSCVRAVDG SIVA2 1-58 nucleotide sequence
(SEQ ID NO: 8)
```
atgcccaagcggagctgccccttcgcggacgtggccccgctacagctcaaggtccgcgtgagccagagggagttgagccg
cggcgtgtgcgccgagcgctactcgcaggaggtcttcgacccatctggggtagcgtccattgcctgttcctcatgcgtgc
gagccgtggatggg
```

SIVA2-1-81 amino acid sequence
(SEQ ID NO: 5)
MPKRSCPFADVAPLQLKVRVSQRELSRGVCAERYSQEVFDPSGVASIACSSCVRAVDGKAVCGQCERALCGQCVRTCWGC

G

SIVA2 1-81 nucleotide sequence
(SEQ ID NO: 9)
```
atgcccaagcggagctgccccttcgcggacgtggccccgctacagctcaaggtccgcgtgagccagagggagttgagccg
cggcgtgtgcgccgagcgctactcgcaggaggtcttcgacccatctggggtagcgtccattgcctgttcctcatgcgtgc
gagccgtggatgggaaggcggtctgcggtcagtgtgagcgagccctgtgcgggcagtgtgtgcgcacctgctggggctgc
ggc
```

The oligonucleotide sequences for site-directed mutagenesis and for suppression of protein synthesis by RNA interference: Human NIK with a mutation corresponding to that of the mouse aly mutation (G860R) was generated with sense
(SEQ ID NO: 12)
5'-ccaagctatttcaatcgtgtgaaagtccaaatac-3'
and antisense
(SEQ ID NO: 13)
5'-gtatttggactttcacacgattgaaatagcttgg-3'

NIK, with its sequence altered to make it non-complementary to the NIK siRNA that was used, was generated with sense
(SEQ ID NO: 14)
5'-gagggtctggaatacctacattcccgcaggattctgcatggg-3' and antisense
(SEQ ID NO: 15)
5'-cccatgcagaatcctgcgggaatgtaggtattccagaccctc-3' as primers.

The TRAF2 binding motifs in the N- and C-terminus of NIK were mutated by the following oligos;

NIK334
sense strand
(SEQ ID NO: 16)
5'-catgagaagttttctgtggcggcataccctagtgcatgctctg-3' antisense strand
(SEQ ID NO: 17)
5'-cagagcatg-cactaggtatgccgccacagaaaacttctcatg-3'

-continued

NIK704
sense strand
(SEQ ID NO: 18)
5'-gggcccggccagctgcggcgacaacaggcagagcc-3' antisense strand
(SEQ ID NO: 19)
5'-ggctctgcctgttgtcgccgcagctggccggggccc-3'

The following siRNA sequences were introduced into the pSUPER vector (with the sequence ttcaagaga as spacer):

For human SIVA-NC3, sense strand
(SEQ ID NO: 20)
5'-gatccctgaataaacctctttatatttcaagagaatataaagaggtttattcattttggaaa-3' antisense strand
(SEQ ID NO: 21)
5'-agcttttccaaaaatgaata-aacctctttatattctcttgaaatataaagaggtttattcaggg-3'

SIVA131
sense strand
(SEQ ID NO: 22)
5'-gatccccgcagtgacatgtacgagaattcaag-agattctcgtacatgtcactgcttttggaaa-3' antisense strand
(SEQ ID NO: 23)
5'-agcttttccaaaaagcagtgacatgtacgagaatctcttgaattctcg-tacatgtcactgcggg-3'

SIVA275 sense strand
(SEQ ID NO: 24)
5'-gatccccactgcagtgacatgtacgattcaagagatcgtacatgtcact-gcagttttttggaaa-3' antisense strand
(SEQ ID NO: 25)
5'-agcttttccaaaaaactgcagtgacatgtacgatctcttgaatcgtacatgtcactgcagtggg-3'

SIVA278 sense strand
(SEQ ID NO: 26)
5'-gatccctagcgtccattgcctgttcttcaagagagaacaggcaatggacgctattttggaaa-3' antisense strand
(SEQ ID NO: 27)
5'-agcttttccaaaaatagcgtccattgcctgttctctcttgaagaacaggcaatggacgctaggg-3'

SIVA518 sense strand
(SEQ ID NO: 28)
5'-gatccccgtgacatgtacgagaaagtttcaagagaactttctcgtacatgtcacttttggaaa-3' antisense strand
(SEQ ID NO: 29)
5'-agcttttccaaaaagtg-acatgtacgagaaagttctcttgaaactttctcgtacatgtcacggg-3'

SIVA521 sense strand
(SEQ ID NO: 30)
5'-gatcccccagctgtgccatg-ttcgattcaagagatcgaacatggcacagctggttttggaaa-3' antisense strand
(SEQ ID NO: 31)
5'-agcttttccaaaaaccagctgtgccatgttcgatct-cttgaatcgaacatggcacagctgggg-3'

GFP sense strand
(SEQ ID NO: 32)
5'-gatccccgctacctgttccatggccattcaagagatggccatgg-aacaggtagcttttggaaa-3' antisense strand
(SEQ ID NO: 33)
5'-agcttttccaaaaagctacctgttccatggccatctcttgaatggccatggaacaggt-agcggg-3'

RNAi knock out. Hairpin siRNA was expressed using the pSUPER vector, as previously described (Brummelkamp et al., 2002). Briefly, a double-stranded oligonucleotide was designed to contain the forward and reverse sequences corresponding to a region in the human SIVA open reading frame antisense strand. The two oligonucleotides were annealed and cloned into the pSUPER vector for expression under the control of the H1 RNA promoter (Brummelkamp et al., 2002). Transient transfection with up to 5-fold excess of this pSUPER-SIVA was performed, as described above.

A lentiviral vector (as previously described by Lois et al., 2002) was used in order to express the pSUPER-SIVA constitutively in Ramos cells. Typically, the cassette including the H1 promoter (Brummelkamp et al., 2002) and SIVA RNAi was excised from the pSUPER vector using EcoRI and HindIII (both from New England Biolabs), the sticky ends were blunted using T4 DNA polymerase (New England Biolabs), and the blunted fragment was inserted into the blunted PacI site of the GFP-expressing FUGW lentiviral vector (Lois et al., 2002). Transduced cells were sorted by FACS for GFP expression (FACS Vantage, Becton-Dickinson). Sorted cells exhibited expression of GFP and deficiency of SIVA for months.

In vitro self ubiquitination: Typically, in vitro ubiquitination assays were performed in a 50 μl reaction volume containing recombinant using a recombinant HIS-ubiquitin where all the lysines in the ubiquitin except K63 are mutated to arginine (Boston Biochem) (8 μg), E1 (0.2 μg), E2 (0.5 μg) and 1-2 μg of recombinant GST-SIVA or GST-SIVAC73A in a buffer containing, 30 mM HEPES pH 7.6, 5 mM MgCl2, 2 mM ATP, 0.2 mM DTT, 5 mM Sodium Citrate, 10 mM creatine phosphate, 0.2 μg/ml creatine kinase and 5 μM ubiquitin aldehyde. Reactions were incubated at 30° C. for 1 hour. The reactions were terminated by addition of Laemmli sample buffer or diluted to 1 ml with buffer containing 20 mM HEPES pH 7.6, 150 mM NaCl, 1% Triton X-100, 1 mM EDTA and complete protease inhibitor cocktail. SIVA was immunoprecipitated using anti-GST antibody adsorbed to proteinG beads for 4 hours at 4° C. Immunoprecipitates were subjected to Western blotting with the indicated antibodies.

Preparation of viral inoculum. Phoenix-ampho cells (1.5×10$^6$ Cells seeded in 9 cm plates) (gift from Prof. Gary Nolan, Stanford university) were transfected by the calcium phosphate method with pBABE puro SIVA2 vector (20 μg/plate) and the conditioned medium containing the virus was collected 48 hours post transfection. 5 ml of medium containing virus was added to 45 ml of RPMI medium containing the BJAB cells (20×10$^6$ cells) and two days later the cells were subjected to selection in puromycin (SIGMA p'7255) containing medium (500 ng/ml) for 4 days. After 4 days, puromycin concentration was increased (1 μg/ml) and the cells were allowed to expand in culture conditions.

Ramos cells constitutively expressing SIVAc. Several single RAMOS B-lymphoblastoid cell clones expressing SIVA-c (constitutively transfected with pSIVAc) were isolated and grown. The expression vector employed to obtain the cell clones expressing SIVAc produces His tagged SIVAc (the His-tag is fused to the C-terminus of SIVAc). RAMOS B-lymphoblastoid cell clones expressing SIVA-c were prepared as follows. B-lymphoblastoid cells were transfected by nucleofection (Amaxa Biosystems) with pSIVAc or control vector pC HIS. 48 hours post transfection; the cells were selected in medium supplemented with 1000 ng/ml Neomycin (G418, Gibco BRL 11811-031) for 30 days. After selection, single cell clones were analyzed by Western blotting using anti-HIS for monitoring the expression of SIVA-c. A positive selected clone was grown and used for experiments.

Example 1

NIK Binds to SIVA, an Adapter Protein Associated with CD27

Screening a human bone-marrow two-hybrid library using NIK as bait it was found that NIK binds to a C-terminal fragment of SIVA (See FIG. 1A) As in the case of NIK-binding to TRAF2 (Malinin et al., 1997), the SIVA fragment was found to bind to the C-terminal part of NIK, and this binding was stronger than that observed with the full-length NIK protein (FIG. 1A), quite likely due to the propensity of the N-terminal part of NIK to bind to its C-terminus and thus block its binding to other proteins (Xiao and Sun, 2000).

To test whether NIK can bind SIVA in mammalian cells, NIK was expressed either with SIVA1 or SIVA2, the two known SIVA splice variants (Yoon et al., 1999), in transiently transfected HEK-293T cells. As shown in FIGS. 1B and 1C, NIK co-immunoprecipitated bidirectionally with both splice-variants of SIVA from lysates of the transfected cells.

Interestingly, the cellular levels of SIVA1 and SIVA2 in the transfected cells were increased by the co-expression of NIK, apparently reflecting stabilization of SIVA by its associated NIK molecules. At the particular dose of SIVA cDNA applied in this set of experiments, the expression of NIK was also enhanced by the co-expression of either of the two splice-variants of SIVA. Such enhancement was not observed upon co-expression of GFP or IKK1 with NIK (FIGS. 1B, C and D). Notably, upon co-expression with aly NIK, the two SIVA isoforms displayed difference in effects. While both SIVA1 and aly NIK were stabilized and interacted upon their co-expression, SIVA2 did not stabilize the co-expressed aly NIK nor was SIVA2 stabilized by aly NIK. Due to this lack of stabilization the binding of aly NIK to SIVA2 could not be assessed (FIGS. 1B and C).

To recapitulate the interaction of NIK and SIVA in vitro, GST tagged SIVA2 was expressed in bacteria and an N-terminal deletion mutant of NIK (NIK 338-947) was expressed in baculovirus. Co-incubation of the two proteins, followed by immunoprecipitation of NIK pulled down SIVA2 specifically, thus reconfirming that their interaction in vivo is direct (FIG. 1E).

Furthermore, endogenous SIVA2 was also found to interact with a stably expressed NIK in Ramos cells after CD70 ligand treatment (FIG. 1F). Likewise, in BJAB cells stably expressing NIK and retrovirally transduced with SIVA2, these two proteins interacted after long term treatment with CD40 ligand, but not with TRAIL, another TNF family ligand (FIGS. 1G-H). By contrast, no interaction of SIVA1 and NIK was observed in a stable cell line expressing the two proteins (not shown).

A previous report addressing the interaction of SIVA with CD27 and GITR receptors suggested that SIVA binds to TRAF2 binding domains in the two receptors (Spinicelli et al., 2002). Since NIK is also a TRAF-binding protein one could suspect that SIVA and TRAF2 bind to NIK competitively. However, two mutant versions of NIK with altered TRAF2 binding domains in the NIK N and C termini bound SIVA as effectively as wild type NIK (FIG. 1). SIVA also appears to be capable of affecting NIK function. When expressed alone, SIVA1 and SIVA2 caused only slight activation of NF-κB. However, both splice-variants of SIVA significantly enhanced the activation of NF-κB by co-expressed NIK while having no effect on the activation of NF-κB by the NIK aly mutant (FIG. 1j).

Example 2

Figure 2:
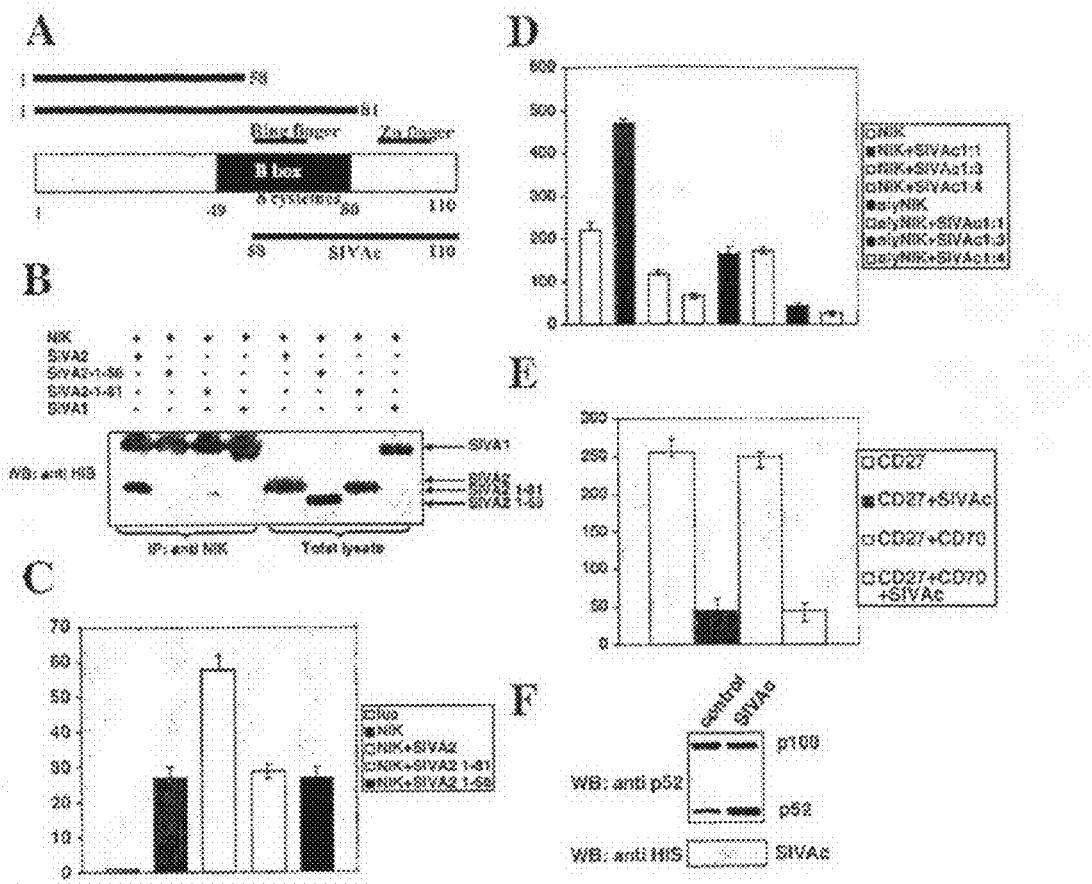
FIGS. 2A-2F show that the Ring/Zinc finger region of SIVA is involved on modulation of the function of NIK. A. Diagrammatic representation of the structure of SIVA2 and of the deletion mutants used in the experiments. B. myc tagged NIK and HIS tagged SIVA2 and two C-terminal deletion mutants thereof were expressed in HEK 293T cells followed by immunoprecipitation of NIK and Western blot analysis as indicated. C. Effect of the over-expression of NIK, alone or together with SIVA2 and its deletion mutants on the expression of NF-κB luciferase in HEK 293T cells was assessed 24 hours after transfection. D. Effect of SIVA-C expression on NIK and aly NIK induced NF-kB activation and E. Effect of SIVA-C expression on CD70 induced NF-kB activation in CD27 transfected HEK 293T cells. The data presented are the mean of those obtained in two experiments in which each test was done in triplicates. F. SIVA-C terminus was expressed constitutively in RAMOS B-lymphoblastoid cells. Western blot detection of the His tagged SIVA2 (lower panel). Nuclear extracts were probed with anti-p52 antibody (top panel).

A Domain in SIVA Containing Ring Finger Like and Zinc Finger Like Motifs is Crucial for Binding NIK and Contributes to the SIVA-Induced Modification of NIK Function Siva contains a Ring/Zinc finger homolog cysteine rich region in its C-terminus (FIG. 2A). So far, no function has been attributed to this 'B-box-like ring' domain. Deletion analysis to define the NIK binding domain in the B-box-like ring of SIVA2 suggested that the terminal Zinc finger like domain is the major NIK binding region (FIG. 2B). Indeed, direct binding of NIK to a truncated SIVA (SIVA-C), which lacks the N-terminal portion of SIVA (from residue 1 to 57, FIG. 2A) was detected in transiently transfected cells (FIG. 2F). In line with this, a reporter gene assay showed that once the Zinc finger domain is deleted, SIVA2 loses its ability to potentiate NIK induced NF-κB activation (FIG. 2C). To test the possibility that expression of this truncated binding domain may behave as a competitive inhibitor, binding to and blocking NIK function, SIVA-C terminus was expressed in cells together with NIK. Interestingly, like the full length SIVA2, also SIVA-C terminus at low concentration showed enhancing effect on NIK induced NF-κB activation (FIG. 2D). This inhibitory effect was also observed in a more physiologically meaningful condition as the overexpressed SIVA-C also compromised CD27 induced NF-κB activation, probably by binding to and blocking NIK function (Ramakrishnan et al., 2004) (FIG. 2E). Consistently, stable clones of Ramos cell line constitutively expressing low level of SIVA-C showed elevated basal level of p52 (FIG. 2F); most likely by activation of NIK function causing enhanced p100 processing.

Example 3

SIVA Promotes Polyubiquitination of NIK

Figure 3:
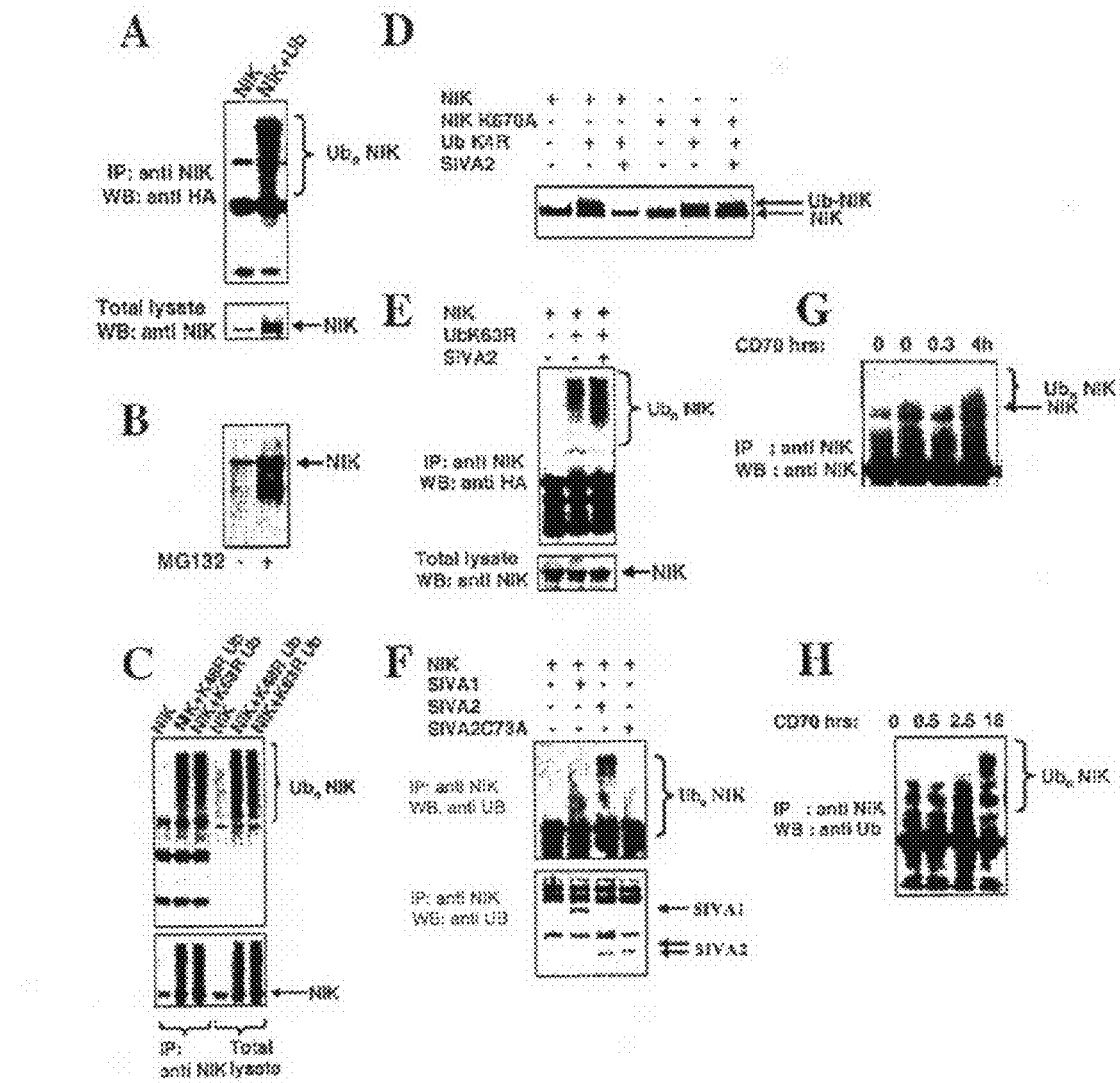
FIGS. 3A-3H show that ubiquitination of NIK is mediated by SIVA2. A. Plasmids encoding NIK and Ubiquitin were transfected at 1:3 ratio into HEK 293T cells. Twenty-four hours later lysates were prepared and immunoprecipitated with anti-NIK antibody and analysed by Western blotting. B. HeLa cells were transfected with NIK and exposed to the proteasomal inhibitor MG132 (25 µM) for the last 4 hours of 24 hours transfection. DMSO was used as the diluent control and total lysates analysed by Western blotting using anti-NIK. C. NIK was co-expressed with ubiquitin mutants at 1:3 ratio in HEK 293T cells. The immunoprecipitated NIK analysed by Western blotting with anti-ubiquitin antibody. D. Co-transfection of NIK or NIK K670A with SIVA2 and an ubiquitin where 4 lysines were replaced by arginine to eliminate polyubiquitination in HeLa cells. Total cell lysates were analysed by anti-NIK Western blotting. E. Co-transfection of NIK with SIVA2 and HA tagged ubiquitin mutant plasmid that cannot form K63 polyubiquitin chains. Anti-NIK immunoprecipitate was analysed by anti-HA Western blotting to monitor K48 linked polyubiquitin chains. F. NIK was transiently over-expressed in HEK 293T cells with SIVA1, SIVA2 or SIVA2 in which the ring finger was mutated (C73A). NIK was immunoprecipitated from the cell lysates and probed for ubiquitin conjugation to NIK (top panel) probed for the co-precipitation of the SIVA proteins (bottom panel). G. Ramos cells expressing retrovirally transduced NIK were treated with CD70. Immunoprecipitated NIK was analysed by Western blotting using anti-NIK antibody. H. HEK 293T cells stably expressing CD27 receptor and NIK were treated with CD70. Immunoprecipitated NIK was analysed by Western blotting using anti-ubiquitin antibody to monitor NIK ubiquitination.

NIK undergoes ubiquitination upon co-expression with ubiquitin (FIG. 3A). Exposure of NIK expressing cells to proteasomal inhibitors results in accumulation of polyubiquitinated NIK (FIG. 3B). Employing various ubiquitin mutants, it was found that NIK could conjugate both to K48 and K63 polyubiquitin chains (FIG. 3C). Surprisingly, NIK also showed monoubiquitination upon co-expression with an ubiquitin mutant whose lysines were replaced with arginines (K11, 29, 48, 63R) (FIG. 3D). In consistence with the monoubiquitination, manual scanning of the NIK sequence showed the presence of an Ubiquitin Interacting Motif [UIM, a potential ubiquitin binding sequence (Hofmann and Falquet, 2001)]. It was found that addition of SIVA2 enhanced both K48 and K63 types of NIK ubiquitination (FIGS. 3E, 3A and 3B), while having no impact on monoubiquitination of NIK (FIG. 3D). Mere co-expression of NIK and SIVA in HEK 293T cells caused appearance of polyubiquitinated NIK with endogenous ubiquitin (FIG. 3F). Interestingly, high molecular weight forms of NIK corresponding to NIK conjugated with endogenous polyubiquitin chains were found also in Ramos (FIG. 3G) and HEK 293T (FIG. 3H) cell lines expressing tagged NIK after CD27 activation. This finding along with the recruitment of SIVA2 to NIK is in line with the possible involvement of SIVA in CD27 function (Prasad et al., 1997). SIVA1 also induced ubiquitination of NIK, but to a lesser extent compared to SIVA2 (FIG. 3F). Since the ring finger motif is important for catalytic activity of ubiquitinating enzymes, one of the conserved cysteine residues in the ring finger-like domain of SIVA2 was mutated (SIVA2 C73A) to study its consequence on NIK ubiquitination. It was found that the ring finger mutant SIVA2 showed dramatically reduced ability to ubiquitinate NIK further confirming the specificity of the reaction (FIG. 3F).

Example 4

Figure 4:
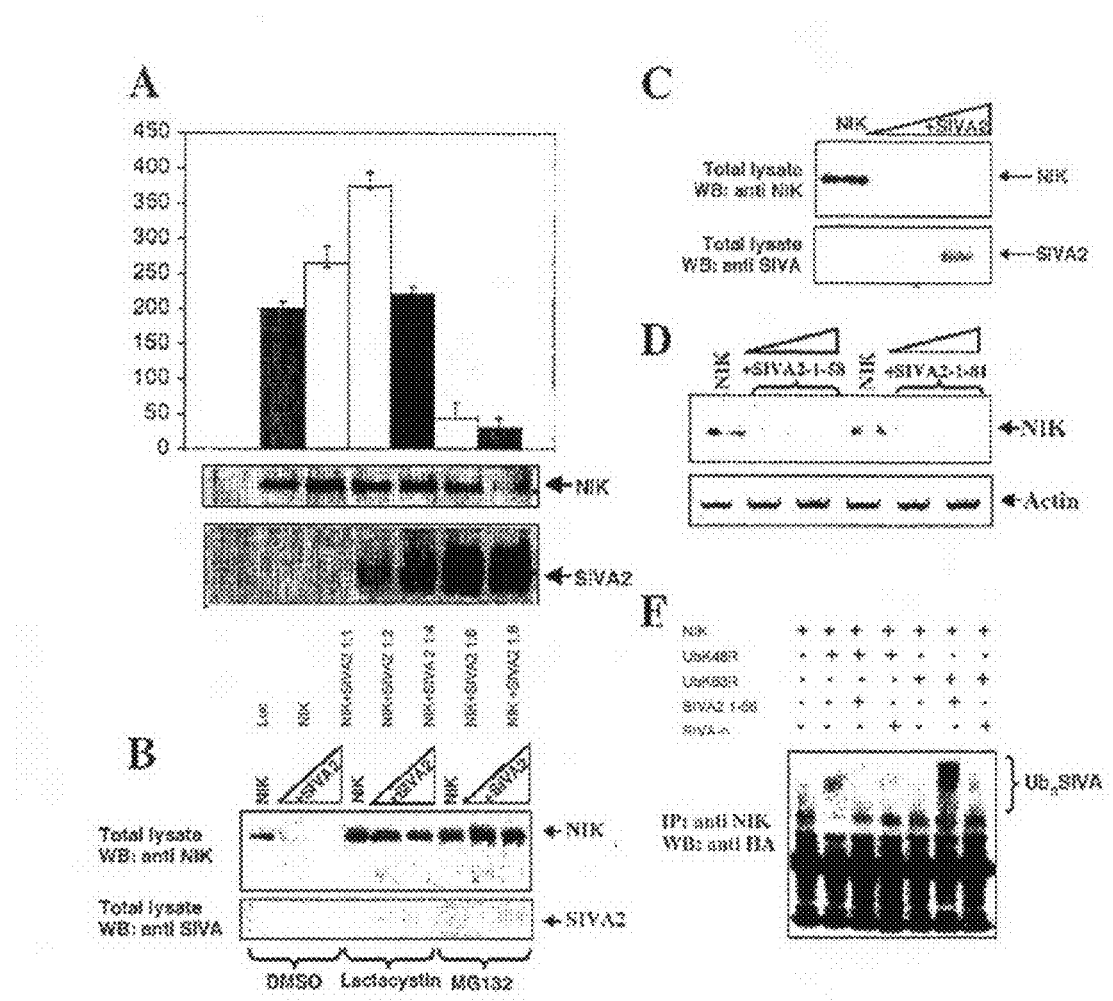
FIG. 4A-4E shows negative regulation of NIK by SIVA2. A. NIK 0.5 µg and SIVA2 at the indicated ratios were transiently expressed in HEK 293T cells with an NF-κB reporter luciferase. Twenty four hours later the cells were lysed and their luciferase activity was determined luminometrically. Result represents mean of duplicates from one of the three independent experiments. B. NIK (0.5 µg plasmid) without or with SIVA2 (1.5 µg and 3 µg plasmid) was transiently expressed in HeLa cells. During last 6 hrs of 30 hrs incubation cells were treated with the proteasomal inhibitors, Lactacystin 20 µM or MG132 50 µM and total lysates were analysed by Western blotting. C. SIVA2 plasmid (1.5 µg and 3 µg) was transfected into HEK 293T cells stably expressing NIK. Thirty hours post transfection, total lysates were analysed by Western blotting for NIK and SIVA2 levels. D. Two deletion mutants of SIVA2 were co-transfected with NIK (0.5 µg) at 1:3 and 1:6 ratios. NIK levels in the lysates were assessed thirty hours post transfection. Lower panel shows actin as loading control. E. NIK plasmid (4 µg) was co-transfected with SIVA 1-58 or SIVA-C plasmid (8 µg) and HA-ubiquitin K48R or K63R mutant plasmid (6 µg) in HeLa cells. Twenty-four hours post transfection cells were harvested, lysed and immunoprecipitated with anti-NIK antibody. Western blotting was performed with anti-HA for detection of ubiquitin conjugates on NIK.

SIVA2 Negatively Regulates NF-κB Activation—an Activity Most Likely Reflecting its Ability to Impose NIK Degradation SIVA is a pro-apoptotic molecule and induces cell death in a caspase dependent mitochondrial pathway. Consistent with its key role in apoptosis, SIVA is upregulated in response to UV and oxidative stress in different cell types and is a direct transcriptional target of tumor suppressors p53 and E2F1 (Fortin et al., 2004). In the process of apoptosis, caspase 8 is known to cleave proteins like NIK to suppress NF-κB pathway, a pathway which plays a pivotal role in cell survival and proliferation (Foehr et al., 2000). While assessing the effect of SIVA2 expression on NIK induced NF-κB activation it was found that, while having stimulatory effect at low doses, SIVA2 at high doses completely suppressed NIK induced NF-κB activation (FIG. 4A). This was well correlated with the expression level of NIK in cells, having dramatically reduced level of NIK in presence of high concentrations of SIVA2 (FIG. 4B, first three lanes). Since SIVA2 augments K48 ubiquitination of NIK in transient expression, it was hypothesized that SIVA2 induces K48 ubiquitination of NIK leading to its proteasomal degradation. Consistently, proteasomal inhibition with MG132 or Lactacystin efficiently protected NIK from SIVA induced degradation (FIG. 4B). Excluding the possibility of other means of degradation, expression of the pan caspase p35 baculoviral inhibitor or treatment with lysosomal inhibitor did not protect NIK from SIVA2-induced degradation (not shown). Overexpressed SIVA2 also degraded NIK expressed stably in HEK 293T cells (FIG. 4C). By contrast, SIVA1 did not show ability to impose degradation of NIK (not shown). Next, it was tested the two deletion mutants of SIVA2, one without the zinc finger and the other without both the ring and zinc fingers, for their ability to degrade NIK. Interestingly, like the full-length protein, both deletion mutants were found capable of inducing NIK degradation (FIG. 4D). Since SIVA2 1-58, devoid of ring and zinc finger, also imposed degradation of NIK, it was tempting to test whether this fragment also could induce K48 ubiquitination of NIK. Indeed, consistent with its ability to impose degradation of NIK, SIVA2 N-terminus, even though incapable of NIK binding, induced specific K48 ubiquitination of NIK (FIG. 4E). This finding suggested that SIVA is not a direct E3 of NIK inducing K48 ubiquitination, but part of an ubiquitinating complex requiring other accessory factors. Similarly, TRAF3 was also reported as an indirect ubiquitinating enzyme of NIK causing its degradation (Liao et al., 2004).

Example 5

A Lysine Residue at Position 670 of NIK is a Site of K48 Ubiquitination Involved in its Degradation by SIVA2

Figure 5:
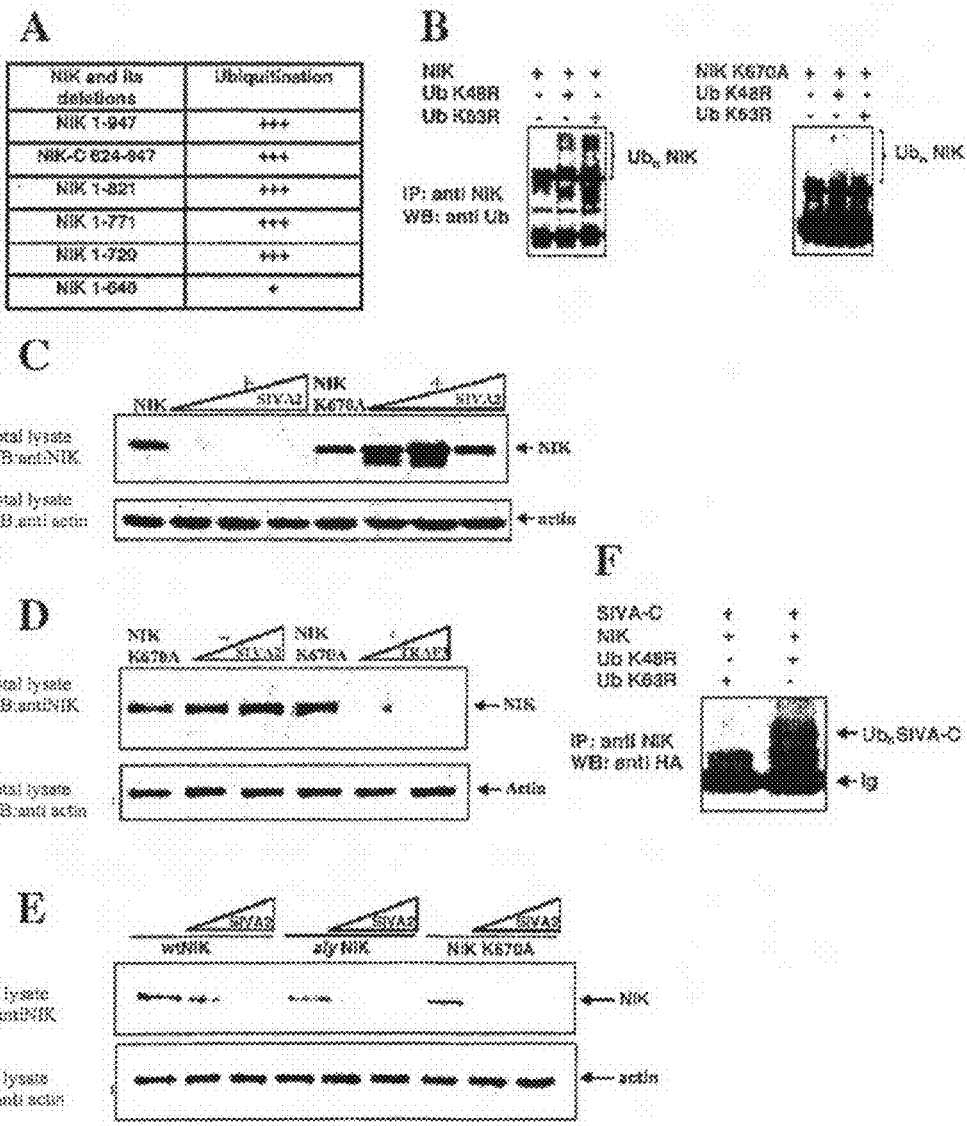
FIGS. 5A-5F show that mutation of the lysine residue 670 in NIK protects NIK from down regulation by SIVA2 A. Table showing extent of ubiquitination of various NIK deletions. B. Co-expression of NIK K670A with ubiquitin K48R and K63R mutants in HEK 293T cells (right panel) compared to the wild type NIK (left panel). Immunoprecipitated NIK was analysed by anti-ubiquitin antibody. C. Degradation of wild type NIK (0.5 µg plasmid) compared to NIK K670A mutant by increasing concentration of SIVA2 (1.0, 2.0 and 3.0 μg plasmid) and D. by TRAF3 in transfected HeLa cells. E. Degradation of wild type NIK, aly NIK and NIK K670A by SIVA2 C73A in transfected HeLa cells. The lower panels in C, D and E show actin as loading control. F. Co-precipitation of SIVA-C with NIK and its ubiquitination (Conditions as in FIG. 4E).

By serial deletion analysis it was defined a short region in NIK, amino acids 640-720, as a potential ubiquitinatable region (FIG. 5A). This region harbors three conserved lysine residues and mutation of one of these lysines to alanine, K670A, specifically decreased K48 ubiquitination of NIK (FIG. 5B right panel) as compared to the wild type NIK (FIG. 5B left panel). Since K48 ubiquitination is a marker for proteasomal degradation and since it was found herein that SIVA2 induced ubiquitination and proteasomal degradation of NIK, the degradation of NIK K670A by SIVA2 was assessed. Indeed, it was found that lysine substitution at residue 670 of NIK dramatically protected NIK from SIVA induced degradation (FIG. 5C). However, at higher concentrations of SIVA2 and prolonged culture period NIK K670A level started to fall in the cells. This proves that lysine 670 is a crucial but not the only residue involved in K48 ubiquitination of NIK by SIVA2 leading to its degradation. Lysine 670 probably serves as an initial residue undergoing K48 ubiquitination by SIVA2 sensitizing NIK to degradation. Previously, TRAF3 overexpression was reported to cause NIK degradation (Liao et al., 2004). While comparing the ability of SIVA2 and TRAF3 to impose degradation of NIK K670A, it was found that lysine 670 mutation could protect NIK only from SIVA2-induced and not from TRAF3-induced degradation (FIG. 5D). Thus, NIK is degraded both in response to SIVA2 and to TRAF3, but the molecular mechanisms involved in the two processes differ.

Next, as it was observed that SIVA ring finger mutation (SIVA2 C73A) greatly decreases its ability to ubiquitinate NIK, the consequence of expression of this mutated SIVA2 on NIK degradation was tested. Like the wild type, ring finger mutant SIVA2 also degraded NIK and aly NIK. Unexpectedly, unlike the wild type, SIVA2 C73A effectively degraded co-expressed NIK K670A (FIG. 5E).

By transient expression with different ubiquitin mutants, it was found that the ring finger region, SIVA-C, by itself undergoes K63 ubiquitination and co-precipitates with NIK (FIG. 5F). However, unlike the full-length SIVA, SIVA-C was found incapable of imposing K63 ubiquitination of NIK (FIG. 5E).

Example 6

Figure 6:
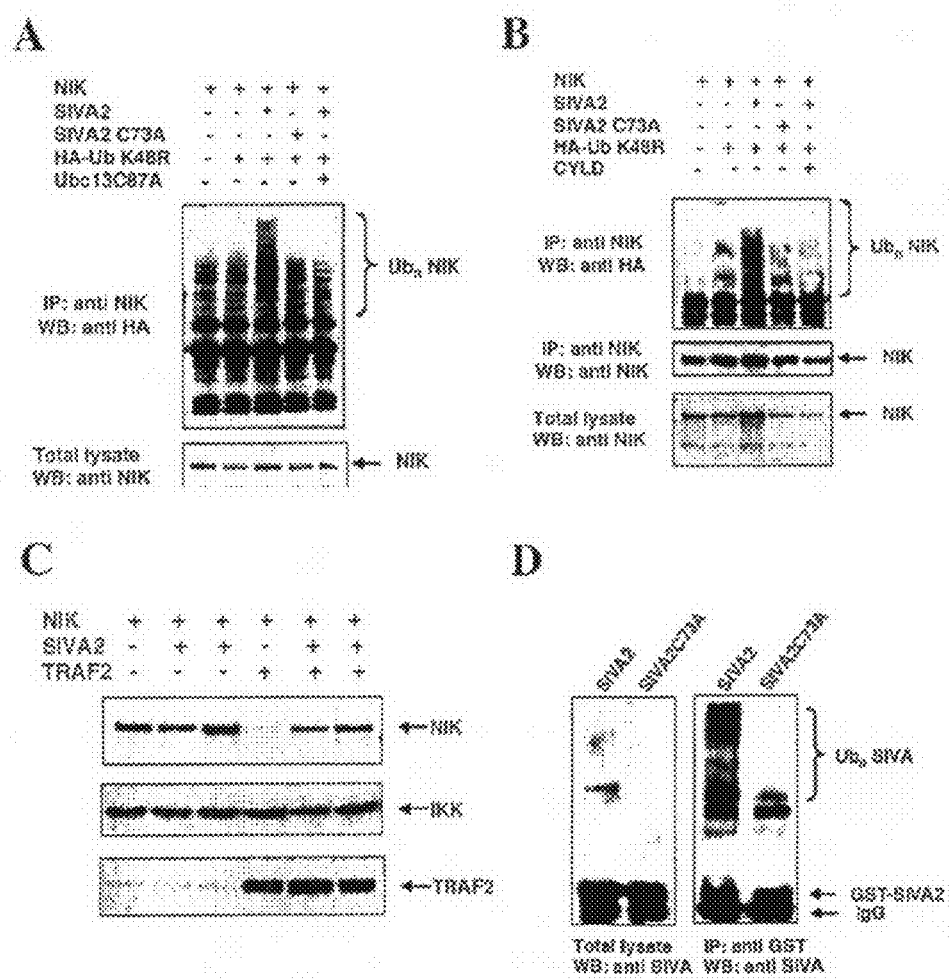
FIGS. 6A-6D show that SIVA2 is an E3 ligase. SIVA2 induced K63 ubiquitination of NIK is inhibited by A. catalytically inactive mutant Ubc13 (C87A) and B. CYLD overexpression. Indicated plasmids were co-transfected into HeLa cells and cell lysates were prepared 24 hrs post transfection. Anti-NIK immunoprecipitates were probed in Western blotting with anti-HA to detect ubiquitination and total lysates with anti-NIK. C. NIK (0.5 μg plasmid) was co-expressed with SIVA2 (1.5 μg and 3.0 μg plasmid) and TRAF2 (0.5 μg plasmid) as indicated. Total cell lysates were prepared 30 hrs post transfection and probed with anti-NIK and anti-IKK1. D. GST-SIVA2 was incubated with E1 (200 ng/50 μl) and E2, Ubc13/Uev1 (500 ng/500), enzymes in an in vitro ubiquitination assay. After 1 hr at 37° C. samples were immunoprecipitated with anti-GST antibody. Both IP and total lysates were analysed by Western blotting using anti-SIVA.

SIVA2 is an E3 Ligase Causing K63 Ubiquitination, and its Ring Finger Mediates this Function E3s are ubiquitin-protein ligases determining the selectivity and efficiency of ubiquitination reactions. Almost all known E3s utilize either a ring finger or HECT domain to participate in ubiquitination reaction (Hoffman and Pickart, 2001). To demonstrate that the SIVA2 ring finger is indeed involved in K63 ubiquitination of NIK, ubiquitin mutant K48R, which permits polyubiquitination only through K63 linked chains, was expressed in cells with NIK. As expected, SIVA2 addition greatly potentiated K63 polyubiquitination of NIK and the ring finger mutation in SIVA2 blocked this ability, demonstrating the K63 ubiquitination as a function of ring finger. Earlier, in our two hybrid screenings, one of the preys fished with NIK C-terminus was ubiquitin conjugating enzyme, Ubc13. This E2 together with a co factor, Uev1, specifically mediates K63 ubiquitination of proteins (Hofmann and Pickart, 2001). To test the involvement of Ubc13 in SIVA2 induced NIK K63 ubiquitination and to reconfirm its specificity, a catalytically inactive Ubc13 (C87A) was overexpressed to block this process (Deng et al., 2000). Consistently, Ubc13 C87A blocked SIVA2 induced NIK K63 ubiquitination (FIG. 6A).

CYLD is a deubiquitinating enzyme targeting K63 linked ubiquitin chains (Kovalenko et al., 2003). Co-expression of CYLD readily deconjugated SIVA2 induced ubiquitin chains on NIK, providing further evidence for specific K63 ubiquitination of NIK (FIG. 6B).

In addition to the in vivo ubiquitination observed, NIK K63 ubiquitination in vitro was tested. Unfortunately, it has been impossible to obtain recombinant NIK either from bacteria or insect cells due to the insolubility and inactivity of the protein prepared in these systems. So we decided to use NIK overexpressed and purified from mammalian cells or from in vitro transcription and translation rabbit reticulocyte lysate system. NIK prepared by both means showed saturating K63 ubiquitination when incubated with E1 and E2 without added E3, obstructing the analysis of the ability of SIVA2 to serve as E3 for its in vitro ubiquitination. This finding indicates that NIK expressed in mammalian system binds avidly and brings down E3 ligase(s) effecting its ubiquitination in vitro. Or, alternatively, that NIK itself possesses E3 ligase activity. Next, baculoviral system was used to express a truncated NIK, lacking the 337 N-terminal amino acids, in insect cells. This truncated NIK (338-947) was more soluble than full length NIK and was applied in the in vitro ubiquitination experiment. NIK338-947 did not show ubiquitination with or without SIVA2. This may be due to inability of this truncated NIK to participate in the process. Alternatively, it may suggest that the NIK N-terminus is the region undergoing K63 ubiquitination.

One more finding that appears to be consistent with the idea that SIVA2 acts to stabilize NIK was gained in an experiment where TRAF2, NIK and SIVA2 were co-expressed in HeLa cells. TRAF2 induced NIK degradation. As shown earlier, SIVA2 at low doses increases NIK amounts and function. In addition, as shown in FIG. 6C, low dose SIVA2 stabilized/protected NIK from TRAF2 induced degradation.

Remarkably, it was found that bacterially-expressed recombinant SIVA2 itself was self-K63 ubiquitinated in an in vitro ubiquitination reaction with added E1 and E2 (Ubc13/Uev1) establishing it as a potent E3 ligase also capable of inducing auto-ubiquitination (FIG. 6D).

Example 7

Figure 7:
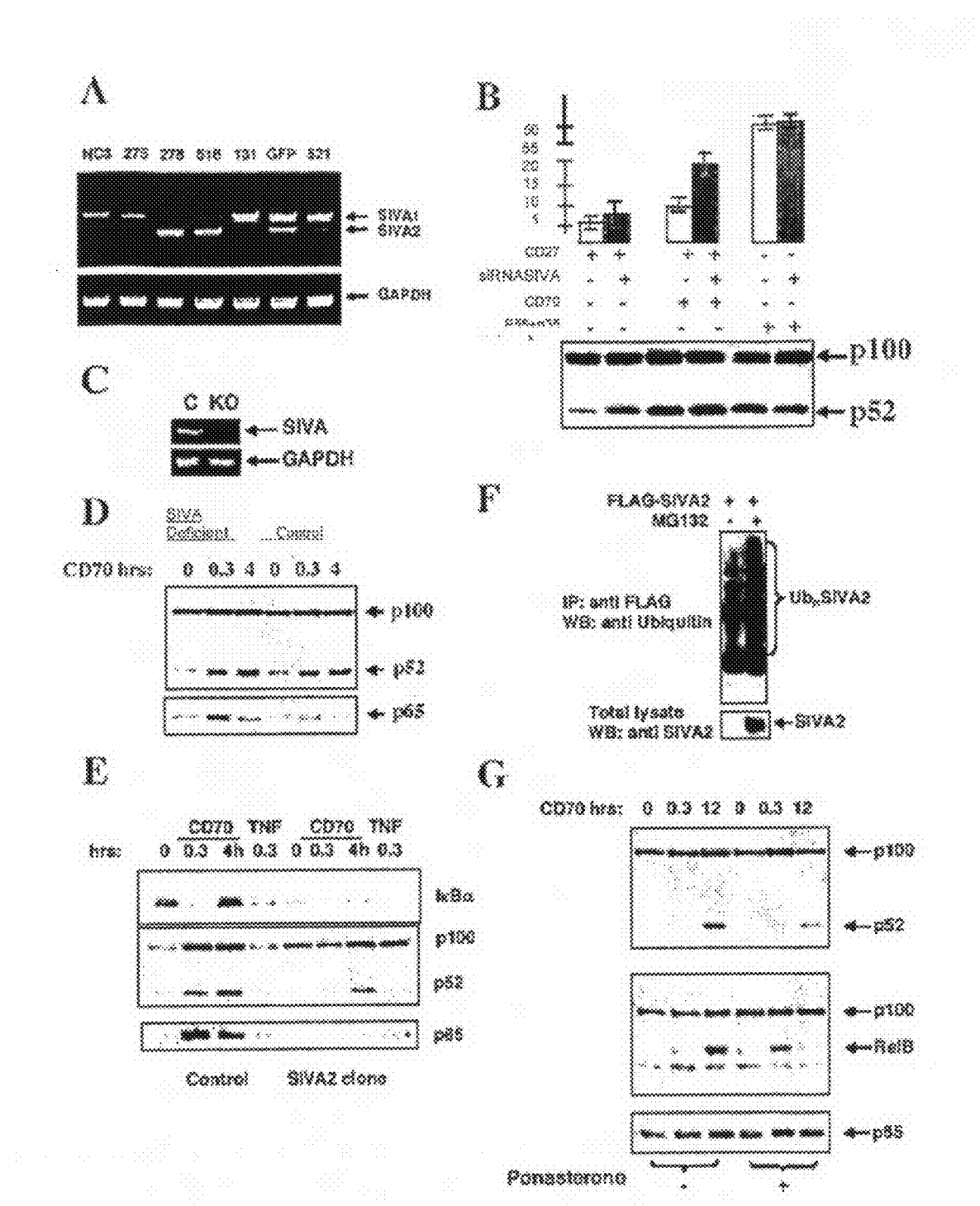
FIGS. 7A-7H show that upregulation or downregulation of SIVA interferes with the function of NIK. A. RT-PCR to test efficiency of various pSUPER-siRNAs to 20' suppress SIVA in HEK 293T cells. Six well plates were seeded with 200,000 cells/well and transfected with various pSUPER-siRNAs by lipofectamine 2000 reagent (Invitrogen). Cells were harvested after 48 hrs of transfection and RNA was extracted using TRIZOL (Invitrogen) reagent. Bottom panel shows GAPDH as control for quantitation. B. HEK293T cells were co-transfected with CD27 or p55 TNFR and p35 (pan caspase inhibitor to protect cells from TNFR induced death), NF-κB luciferase reporter and pSUPER-SIVA siRNA NC3. Twenty-six hours later CD27 transfected cells were treated with CD70 for 4 h, followed by assessment of luciferase activity as well as p52 generation. C. SIVA mRNA levels in Ramos cells transduced with lentiviral vector encoding siRNA NC3 under H1 promoter. D. CD70 induced NF-κB nuclear translocation in Ramos cells in which SIVA expression was suppressed by lentiviral transduction of siRNA SIVA. E. Ramos cells ($1\times10^6$/time point) constitutively expressing SIVA2 and vector control cells were treated with CD70 or TNF for the indicated time points. Cytoplasmic and nuclear extracts were analysed using indicated antibodies. F. Immunoprecipitation of transiently expressed FLAG-SIVA2 from HeLa cells. MG132 was applied at 25 μM for the last 4 hrs of 24 hrs transfection. G. CD27 receptor and ecdysone inducible SIVA2 were stably expressed in 293 cells with ecdysone repressor. Six well plates were seeded with 200,000 cells/well and SIVA2 was induced with 10 μM ecdysone analogue, ponasterone. CD70 was applied together with the inducer for 12 hrs or for the last 20 min of 12 hrs induction. Cells were harvested, nuclear and cytoplasmic extracts were prepared and analysed by Western blotting. H. Shows the effect of SIVA silencing on nuclear translocation of p52 and p65 mediated by NIK in 293-CD27 cells treated with CD70. HEK 293T cells expressing retrovirally transduced NIK were transfected with pSUPER SIVA or pSUPER empty vector as control treated with CD70 expressing medium for 8 hours or remain untreated, and nuclear and cytoplasmic extracts were prepared and analyzed by Western blotting with appropriate specific antibodies for detection of NIK, p100, p52, and p65. Actin specific antibodies were used to detect actin, as the internal control. The results show that silencing of SIVA elevates the levels of NIK in the cytoplasm and of p52 in the nucleus.
Figure 7:
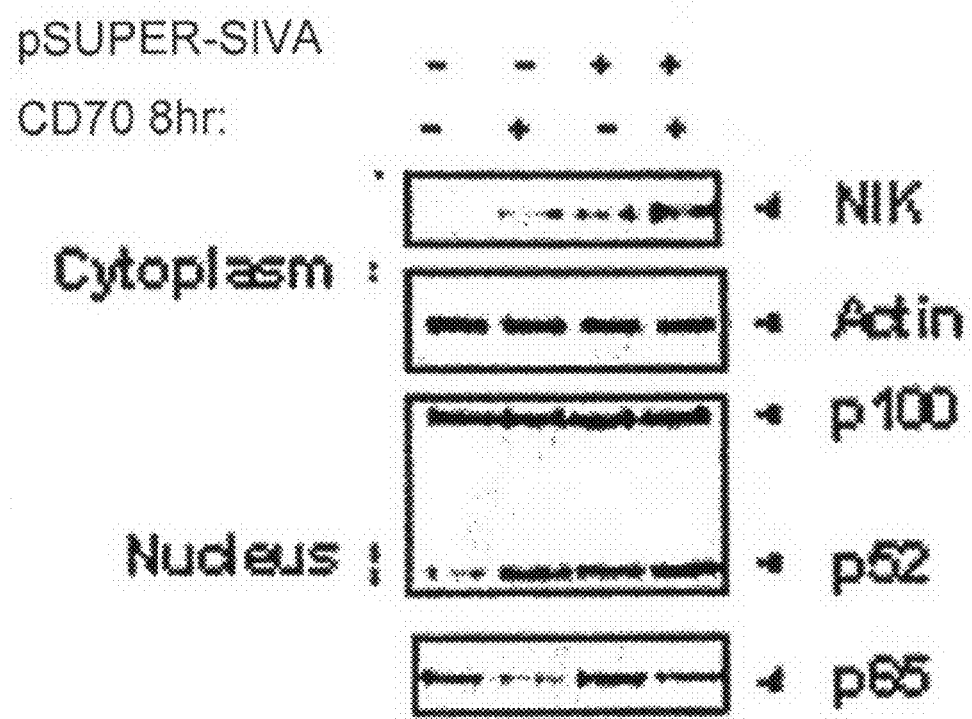

Exploring the Physiological Significance of the Findings that Inducible SIVA2 Expression in Cells Interferes with NIK Function Initially, it was attempted to study SIVA function by suppressing its expression by the small interfering RNA (siRNA) approach. Several siRNAs were designed and cloned into pSUPER vector (Brummelkamp et al., 2002) and tested in HEK 293T cells for their ability to reduce SIVA message. By RT-PCR, two best suppressors, pSUPER-NC3 and pSUPER-275 (FIG. 7A) were selected for further experiments. Transient expression of the pSUPER-NC3 in the context of CD27 induced NF-κB reporter gene activation in HEK 293T cells showed a two-fold increase in luciferase activity (FIG. 7B). In view of the finding that SIVA can induce down regulation of NIK, this finding may imply that lowering SIVA levels promotes CD27-induced signaling through elevation of NIK levels. Next, it was attempted to create SIVA deficient cell lines. For this purpose, lentivirus expressing SIVA specific siRNA was prepared as described (Lois et al., 2002) and different cell lines were transduced. No complete suppression of SIVA was obtained in Ramos, RAJI or BJAB cells with this approach. Testing CD27 signaling in Ramos cells where approximately 75% reduction in SIVA level was achieved (FIG. 7C), only minor differences in p52 and p65 translocation to the nucleus compared to the control cells was found (FIG. 7D). Slightly elevated levels of p52 and p65 in the nucleus of SIVA suppressed cells after CD70 stimulation indicating increased NIK level and function could be seen. However, these subtle differences where not sufficient to derive reliable conclusions.

SIVA is a stress-induced protein (Fortin et al., 2004; Henke et al., 2000; Padanilam et al., 1998). Therefore, it might be more reasonable and feasible to evaluate the physiological role of SIVA by studying the effect of elevated levels of SIVA rather than by following effect of its suppression. In this direction, initially, the consequence of stably expressing SIVA2 in cells was tested. In repeated attempts, SIVA2 was expressed constitutively in cells only for short durations, after which the expression was lost. Testing three different clones of Ramos cells constitutively expressing SIVA2 early after their establishment, it was found that these cells express reduced basal level of IκBα and showed decreased p100 processing and decreased p52 and p65 translocation to the nucleus after CD70 stimulation (FIG. 7E). For further consolidation of the effect of SIVA2 upregulation on NF-κB activation, it was decided to develop inducible expression system for SIVA2. To this end, ecdysone inducible 293T Ecr cells (Invitrogen) were transfected with inducible FLAG-SIVA2 and CD27 receptor and clones expressing both the introduced proteins were identified by selection for drug resistance. SIVA2 expression could be detected after induction of these cells only when exposing them to lactacystin, a proteasome inhibitor, indicating that SIVA2 is a short-lived protein with high turn-over rate, undergoing degradation soon after its synthesis. Under this condition SIVA2 accumulated in cells as early as 3 hours after application of the inducer. Likewise, extensive ubiquitination and potentiation of SIVA2 expression by proteasomal inhibitors was also observed in transient expression tests (FIG. 7F). Recapitulating the experiments done in SIVA2 constitutively expressing cell lines, it was consistently found that induction of SIVA2 expression resulted in reduction of nuclear p52 and also of RelB induction by CD70, indicating disruption of NIK function. However, unlike the Ramos cell clones constitutively expressing SIVA2, inducibly expressed SIVA2 did not significantly affect CD70 induced p65 nuclear translocation in 293 cells (FIG. 7G).

Next, the effect of SIVA silencing on nuclear translocation of P52 and p65 mediated by CD70 induction in HEK 293T cells was explored. For this purpose, HEK 293T cells expressing retrovirally transduced NIK were transfected by calcium phosphate precipitation method with pSUPER SIVA or pSUPER empty vector, pSUPER vector encoding scrambled non specific sequence and pSUPER vector encoding siRNA for GFP sequence as control. Cells transfected with pSUPER SIVA or pSUPER control vector were treated with CD70 expressing medium for 8 hours or remain untreated, nuclear and cytoplasmic extracts were prepared and analyzed by Western blotting with appropriated specific antibodies for detection of NIK, p100, p52, and p65. Actin specific antibodies were used to detect actin, as the internal control. The results show that silencing of SIVA elevates the levels of NIK in the cytoplasm and of p52 in the nucleus (FIG. 7H).

Example 8

NIK Directly Phosphorylates SIVA2 Causing its Stabilization

Figure 8:
FIGS. 8A-8C show that SIVA2 may possibly be a substrate of NIK. A. myc-NIK, HIS-SIVA2 and their mutants were co-expressed as indicated in HEK 293T cells followed by immunoprecipitation of SIVA and in vitro kinase reaction. B. SIVA2 was co-expressed with wild type or kinase inactive NIK in HeLa cells. Twenty four hrs post transfection total lysates were analysed for SIVA expression. Bottom panel shows actin as loading control. C. In vitro kinase assay (top panel). NIK (6 μg plasmid) and kinase dead IKK1 or IKK2 (6 μg plasmid each) were co-expressed with FLAG-SIVA2 (8 μg plasmid) in HEK 293T cells. Twenty four hours post transfection, anti-FLAG immunoprecipitation was performed from the lysates and kinase assay was performed. Total lysates were analysed by Western blotting using the indicated antibodies for verifying the expression level of transfected proteins (bottom panel).
Figure 8:
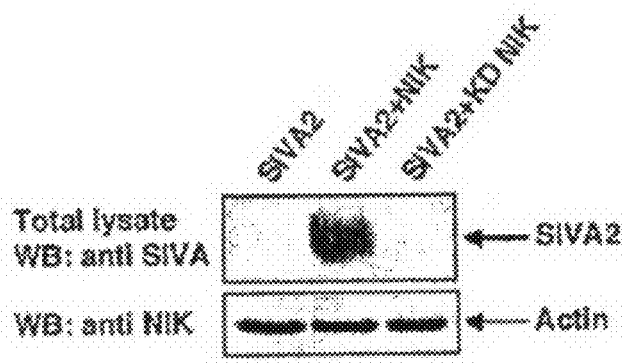
Figure 8:
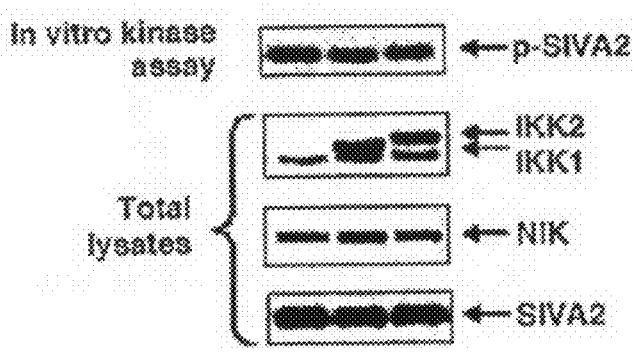

To explore the mechanism accounting for the increase in SIVA protein levels upon co-expression with NIK, it was investigated whether this modulation involves the kinase function of NIK. Using an in vitro kinase assay, it was found that NIK readily phosphorylated SIVA2 suggesting that SIVA2 may be a physiological substrate of NIK. SIVA was earlier reported to undergo tyrosine phosphorylation by ARG kinase at Y34 (Cao et al., 2001a). However it is shown herein that the NIK-induced phosphorylation of SIVA2 is not affected by the Y34F mutation. Also, no phosphorylation of SIVA2 was observed with a kinase-dead NIK (FIG. 8A). While analyzing the total lysates of the cells in these experiments for checking expression of SIVA2, it was found that, while NIK greatly stabilized the co-expressed SIVA2, kinase-dead NIK completely lacked this ability indicating a role of SIVA2 phosphorylation by NIK in SIVA2 stabilization (FIG. 8B). To determine whether NIK-induced SIVA2 phosphorylation is a direct event or one mediated by the downstream kinases of NIK, it was tested whether kinase-inactive IKK1 or IKK2 can interfere with it. Unlike the phosphorylation of NF-κB p100 where NIK exerts it effect through IKK1 (Senftleben et al., 2001), neither of the mutants, of IKK1 or IKK2 had any significant effect on SIVA2 phosphorylation by NIK. These preliminary findings suggest that SIVA2 phosphorylation may be a direct consequence of NIK interaction with SIVA2 (FIG. 8C).

Example 9

SIVA2, but not SIVA1, Promotes NIK Induced Ubiquitination and Cleavage of TRAF3

Figure 9:
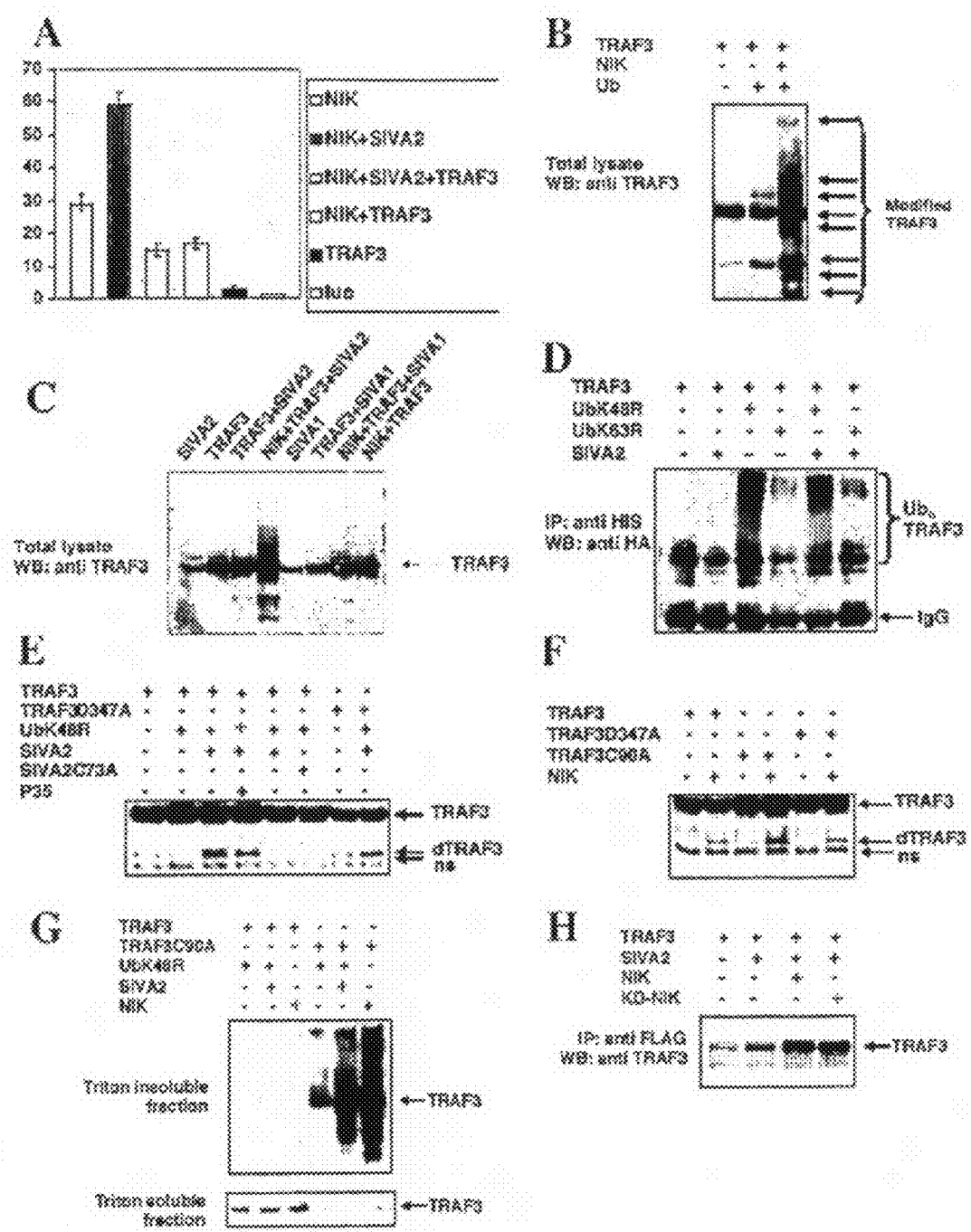
FIGS. 9A-9H show TRAF3 ubiquitination and cleavage mediated by NIK co-operatively with SIVA2. A. HEK 293T cells (200000 cells/well) were seeded in 6 well plates and 24 hours later transfected with the following plasmids as indicated in the figure: myc NIK 0.2 μg, FLAG-SIVA2 0.3 μg, HIS-TRAF3 0.3 μg and HIV-Luciferase 1.0 μg. Twenty four hours later the cells were lysed and their luciferase activity was determined luminometrically. Result represents mean of duplicates from one of the two independent experiments. B. TRAF3 plasmid (3.0 μg), NIK plasmid (4.0 μg) and ubiquitin plasmid (4.0 μg) were co-transfected into HEK 293T cells in 9 cm plates ($1.5\times10^6$ cells/plate). Cells were harvested 24 hrs post transfection and total lysates analysed by Western blotting using anti-TRAF3 antibody. The arrow marks indicates modified TRAF3 forms. C. HEK293T ($1.5\times10^6$ cells/plate) seeded in 9 cm were transfected with 4.0 μg each of the indicated plasmids. Cells were harvested 24 hrs post transfection and total lysates were analysed by anti-TRAF3 Western blotting. D. HIS-TRAF3 (4.0 FLAG-SIVA2 (6.0 μg) and HA-Ubiquitin K48R (6.0 μg) were transfected as in 13 and anti HIS immunoprecipitate was subjected to Western blotting using anti HA antibody. E. Transfections were performed as in D. In lane 4, 4.0 μg of P35 plasmid was also co-transfected. Lane 5 was treated with 25 μM of MG132 for the 8 hours of 28 hours incubation following transfection. F and G. Transfections were performed as in C and 28 hours post transfections cells were harvested and lysed in 1% Triton X-100 containing buffer for 20 min in ice. The lysate was centrifuged at 10000 g and the supernatant was collected as triton soluble fraction. Pellet was resuspended in sample buffer and boiled to obtain triton insoluble fraction. H. Transfections were performed as in C and the lysates were immunoprecipitated with anti FLAG antibody to precipitate SIVA2 and probed with anti-TRAF3.

TRAF3 functions as a negative regulator of NIK, inducing its ubiquitin mediated degradation (Liao et al., 2004). In line with this, overexpression of TRAF3 suppressed NIK induced NF-κB reporter activity. TRAF3 also suppressed the enhancing effect of NIK function conferred by co-expression of SIVA2, at low levels (FIG. 9A).

In the course of these experiments, it was surprisingly found that NIK also modulates TRAF3 levels and affects its ubiquitination and degradation. In the presence of exogenous ubiquitin, NIK dramatically amplified TRAF3 ubiquitination, yielding multiple TRAF3 band pattern in reducing gel. Addition of ubiquitin or NIK alone also modulated TRAF3 to some extent. Careful analysis revealed that, in addition to ubiquitination, a low molecular weight band comprising the N-terminal domain (as it retained the N-terminal HIS tag) of TRAF3 (dTRAF3) appeared as a major cleavage product (FIG. 9B).

Next, the effect of SIVA proteins on NIK induced ubiquitination and cleavage of TRAF3 was tested. Since ubiquitin expression alone affected TRAF3, this experiment was performed without exogenous ubiquitin in order to limit the background. In this set-up, NIK alone caused little modification of TRAF3. However, a clear differential effect of SIVA1 and SIVA2 on NIK induced modulation of TRAF3 was detected. SIVA1 had no effect on TRAF3 over what was induced by NIK. On the contrary, SIVA2 significantly increased TRAF3 ubiquitination and cleavage (FIG. 9C). Upon further analyses of the kind of ubiquitination of TRAF3 (by transient co-expression with K48 and K63 mutant ubiquitins), it was found that the major kind of polyubiquitination of TRAF3 was K63 linked, while K48 linked ubiquitination was minimal (FIG. 9D). Interestingly, co-expression of TRAF3, SIVA2 and the ubiquitin mutant capable of forming K63 linked chains, resulted in ubiquitination and cleavage of TRAF3, generating the dTRAF3 fragment even in the absence of transfected NIK. Substitution of wild type SIVA2 with the ring finger mutant SIVA2 completely abolished the dTRAF3 generation implicating a crucial role for the SIVA2 ring finger in the process. Proteasomal inhibition was also found to inhibit the SIVA2-induced dTRAF3 formation indicating the process is K63 ubiquitination and proteasome-dependent (FIG. 9E). Consistently, lysosomal inhibition did not prevent the cleavage of TRAF3, either in response to SIVA2 or to NIK (not shown). A previous report suggested a similar cleavage of TRAF3 by caspases yielding an N-terminal TRAF3 fragment (Lee et al., 2001). However, mutation of the aspartate residue at the caspase-cleavage site in TRAF3 to alanine (TRAF3D347A) did not prevent its cleavage in response to SIVA2 (FIG. 9E). Likewise, NIK-induced cleavage of TRAF3 was also not blocked by D347A mutation, but appeared enhanced, indicating that the NIK- and SIVA2-induced TRAF3 cleavage occurred by a different mechanism, most likely proteasomal processing. The ring finger mutant TRAF3 was also cleaved by NIK to a similar extent like wild type TRAF3 (FIG. 9F). Surprisingly, it exhibited dramatic ubiquitination in presence of either NIK or SIVA2 and ubiquitin mutant capable for forming K63 linked chains, and was present mostly in the triton insoluble fraction (FIG. 9G).

Next, to understand whether NIK, SIVA2 and TRAF3 really function dependently, we carried out co-precipitation experiments from cells transiently expressing these proteins. Indeed there existed a tripartite complex, which was independent of NIK kinase function. In the absence of exogenous NIK, only a weak interaction of TRAF3 and SIVA2 was observed, probably mediated by endogenous NIK. As in the case of the p100-NIK-IKK1 complex where the binding is not influenced by the kinase function of NIK (Xiao et al., 2004), here also NIK plays the role of an adaptor protein linking TRAF3 and SIVA2 (FIG. 9H).

Example 10

Induction of SIVA2 in HeLa and Ramos Cells Results in Further Activation of NF-κB In order to examine the effect of SIVA2 on the alternative activation of NF-κB, the TREX cloning system (Invitrogen) which allows tetracycline (or doxy-doxycycline, a tetracycline Analogue) inducible expression of the cloned genes was used. The SIVA2 gene was cloned in the TREX system and it was stably introduced into HeLa cells. Cells show inducible SIVA2 expression (data not shown), furthermore, when SIVA2 expression was not induced the cells respond to LIGHT ligand normally in terms of NF-κB activation.

Figure 10A:
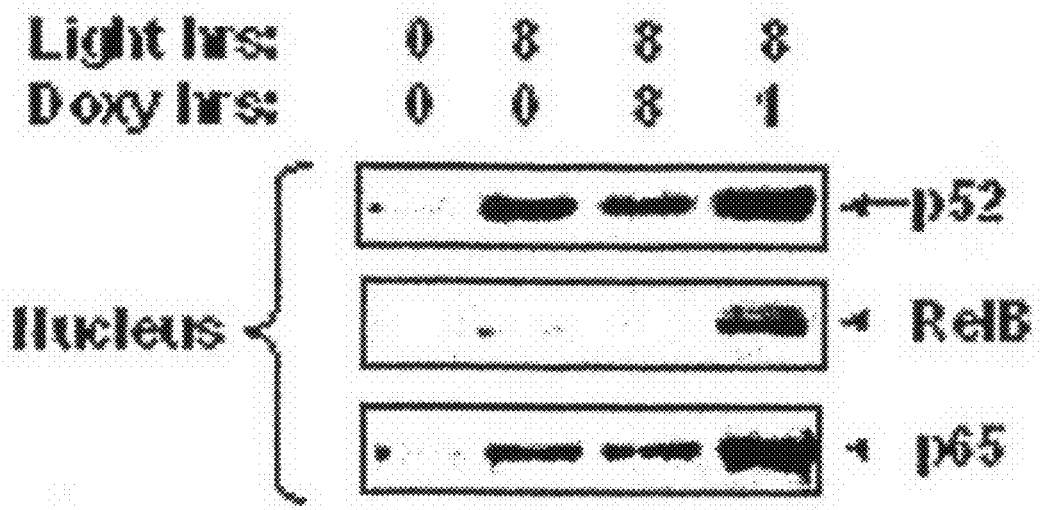
FIGS. 10A-10D show the effect of SIVA2 on ligand activation of NF-κB in HEK 293T, HeLa and Ramos cells. A. HeLa TREX cells capable of expressing tetracycline (or doxycycline) inducible SIVA2 were treated with LIGHT enriched medium for 8 hours in order to activate NF-κB. Following LIGHT treatment the cells were lysed nuclear fraction was isolated and subjected to Western blot analysis probed with anti-p52, RelB or p65 specific antibodies. LIGHT induced both p52 and p65 nuclear translocation in HeLa cells. A short time induction of SIVA2 enhanced LIGHT-mediated p52 and p65 nuclear translocation, while long time induction of SIVA2 interfered with LIGHT-mediated nuclear translocation of both p52 and p65. B. SIVA2 cDNA cloned in pIND vector was stably expressed in the 293-ecr cells (Invitrogen) system. This system allows ecdysone (or the analogue ponasterone)-mediated inducible expression of cloned SIVA2. These cells were treated for 8 hours with CD70 to induce activation of the alternative NF-κB pathway or remained untreated. After treatment, the cells were lysed, fractionated into cytoplasmic and nuclear fractions and subjected to Western blot analysis probed with anti NIK, TRAF2, TRAF3 p100 and p52 antibodies. Induction of SIVA2 for a short time, at the last hour of CD70 induction, decreased the level of TRAF2/3 and increased the levels of NIK and p100 processing resulting in increased nuclear p52 levels. Induction of SIVA2 for a long time, 8 hours along the CD70 treatment, decreased the levels of NIK and nuclear p52. C. Ramos cells harboring the TREX system capable of expressing tetracycline (or doxycycline) inducible SIVA2 or the mutant SIVA2C73A were treated with CD70 for 0, 0.3 or 8 hours and the effect of induction of SIVA2 or the mutant SIVA2C73A for long time (8 hours) short time (1 hour) on CD70 induced NF-kB activation was explored. As indicated in the figure, for the eight hours treatment of ligand with induction of SIVA, doxycycline was applied together with the ligand. For one hour induction of SIVA, doxycycline was added at the last hour of the eight hour-ligand treatment. In case of short time CD70 treatment, doxycycline was added for eight hours or for one hour and the ligand was applied for the last 0.3 hours. Cells treated and induced as indicated, were lysed, fractionated into nuclear and cytoplasmic extracts and these fractions were subjected to Western blot analysis probed with anti-IκBα, p65, p100 and p52 specific antibodies. Induction of wild type SIVA2 blocked CD70 induced IκBα degradation and p65 translocation to the nucleus. Induction of the ring finger mutant SIVA did not block CD70 induced IκBα degradation and it enhanced nuclear translocation of p65. SIVA2 induction also blocked CD70 induced p52 nuclear translocation in a ring finger dependent manner. D. Ramos TREX cells capable of expressing tetracycline inducible SIVA2 or the mutant SIVA2C73A were treated with TNF for 0, 0.3 and 4 hours and the effect of long time (4 hours) or short time (1 hour) SIVA2 or SIVA2C73A induction on TNF induced p65 translocation to the nucleus was explored as described above. Following treatments cells were lysed, fractionated into nuclear and cytoplasmic extracts, and subjected to Western blot analysis probed with anti-p65 specific antibodies. Induction of wild type SIVA2 blocked TNF induced p65 translocation to the nucleus. Induction of the ring finger mutant of SIVA did not block TNF induced nuclear translocation of p65.

HeLa TREX cells capable of expressing tetracycline inducible SIVA2 were treated with LIGHT enriched medium for 8 hours in order to activate NF-κB. Following a LIGHT treatment the cells were lysed fractionated into cytoplasmic and nuclear fractions and the nuclear fraction was subjected to Western blot analysis probed with anti-p52, RelB or p65 specific antibodies. It was found that LIGHT induced both p52 and p65, nuclear translocation in HeLa cells. The effect of induction of SIVA2 on LIGHT-mediated NF-κB activation was studied. The results obtained show that short time induction of SIVA2 enhanced LIGHT-mediated p52 and p65 nuclear translocation, while long time induction of SIVA2 interfered with LIGHT-mediated nuclear translocation of both p52 and p65 (FIG. 10A).

Figure 10B:
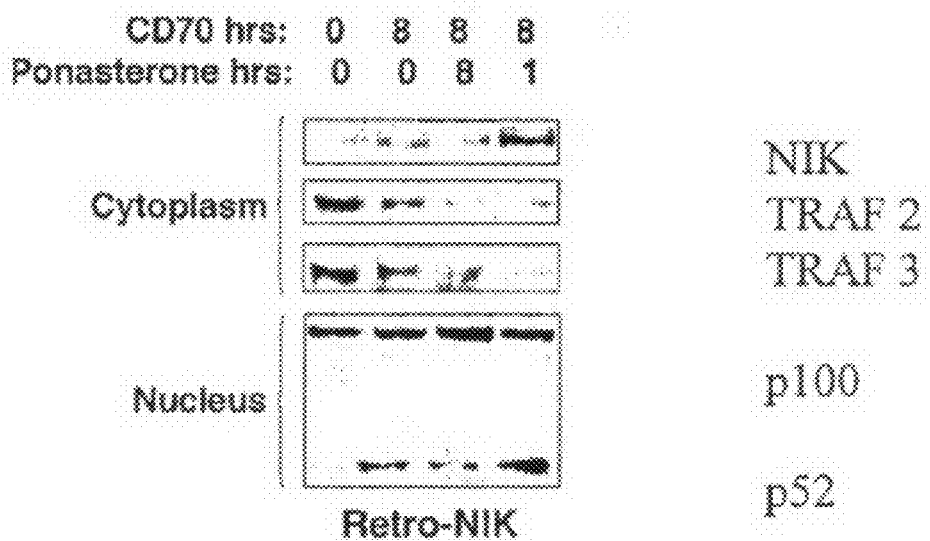

The SIVA2 gene was cloned in the 293-ecr cells (Invitrogen) system. This system allows ecdysone (or the analogue ponasterone)-mediated inducible expression of SIVA2. 293-ecr cells with the SIVA2 gene cloned were engineered to express CD27 constitutively. These cells were treated for 0, and 8 hours with CD70 to induce activation of the alternative NF-κB pathway. After treatment, the cells were lysed, fractionated into cytoplasmic and nuclear fractions and subjected to Western blot analysis probed with anti NIK, TRAF2, and TRAF3 p100 and p52 antibodies. The results show that induction of SIVA2 for a short time, at the last hour of CD70 induction, decreased the level of TRAF2/3 and increased the levels of NIK and p100 processing resulting in increased nuclear p52 levels. Induction of SIVA2 for a long time, 8 hours along the CD70 treatment, decreased the levels of NIK and nuclear p52 (FIG. 10B). These results indicate that in 293 cells SIVA has both positive and negative regulatory effects on NIK and NIK mediated NF-κB activation.

Figure 10C:
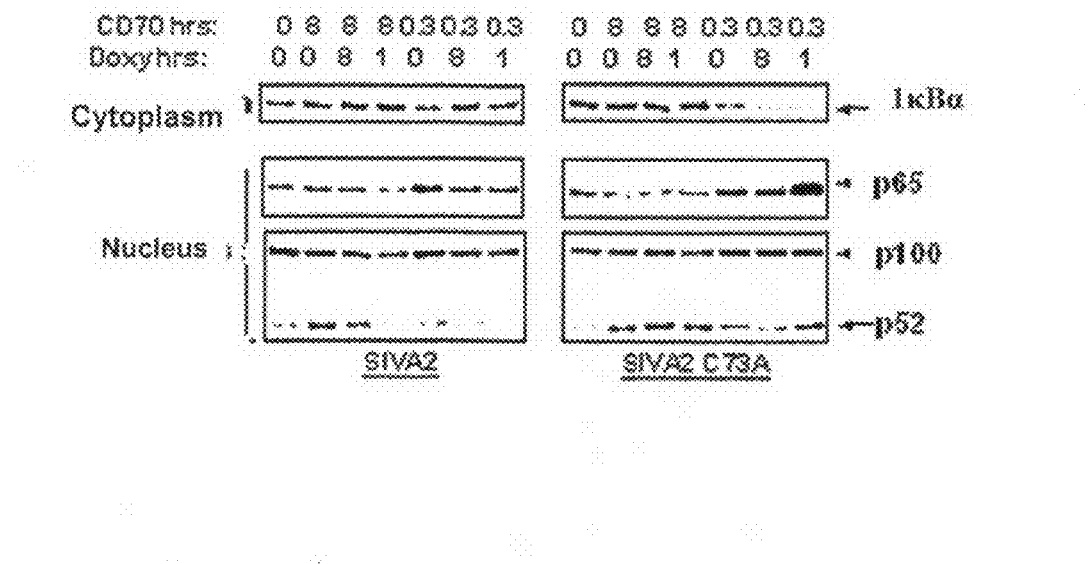

Ramos cells harboring the TREX system capable of expressing tetracycline inducible SIVA2 or the mutant SIVA2C73A were treated with CD70 to activate NF-κB and the effect of SIVA2 induction on CD70 induced NF-κB activation was studied. For this purpose, Ramos cells were treated with CD70 for 0, 0.3 or 8 hours and were induced to express SIVA2 or the mutant SIVA2C73A for long time (8 hours) short time (1 hour) or non induced. As indicated in the figure, for the eight hours treatment of ligand with induction of SIVA, doxycycline was applied together with the ligand. For one hour induction of SIVA, doxycycline was added at the last hour of eight hrs ligand treatment. In case of short time CD70 treatment, doxycycline was added for eight hrs or for one hour and ligand was applied for the last 0.3 hours. Next, the cells were lysed, fractionated into nuclear and cytoplasmic extracts and subjected to Western blot analysis probed with anti-IκBα, p65, p100 and p52 specific antibodies. The results obtained show that induction of wild type SIVA2 blocked CD70 induced IκBα degradation and p65 translocation to the nucleus (FIG. 10C). In contrast, induction of the ring finger mutant SIVA did not block CD70 induced IκBα degradation and it enhanced nuclear translocation of p65. SIVA2 induction also blocked CD70 induced p52 nuclear translocation in a ring finger dependent manner. Thus, unlike adherent cells, such as HEK 293T and HeLa, in lymphocytes short term SIVA induction did not enhance NF-kB activation, indicating that the mode of action of SIVA in non-lymphoid and lymphoid cells differs.

Figure 10D:
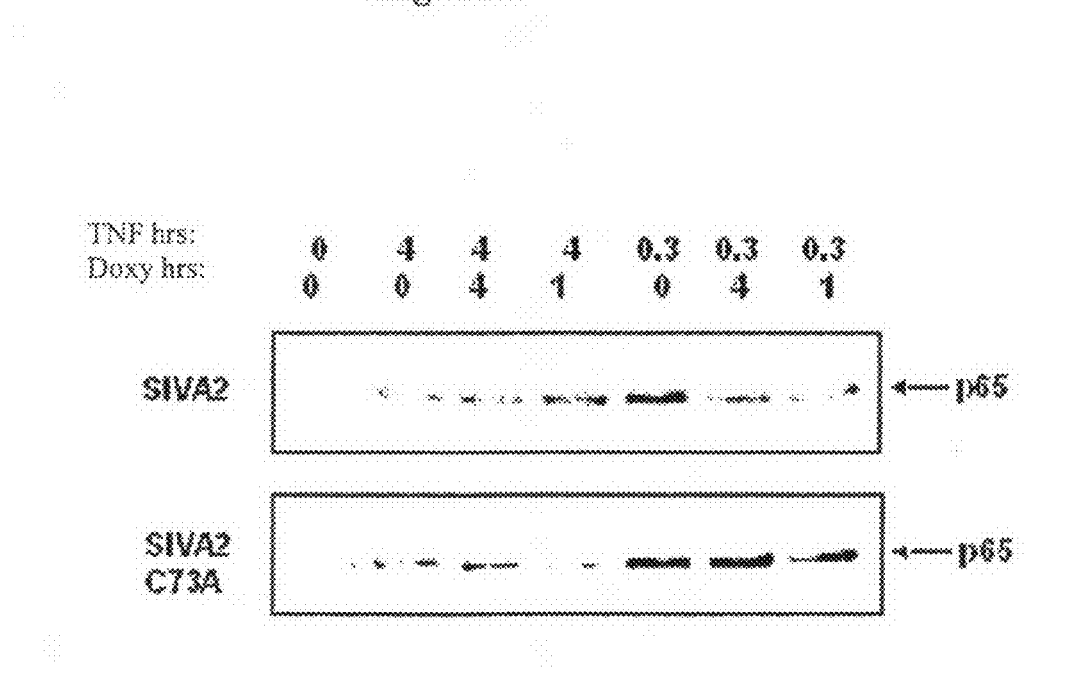

Ramos TREX cells capable of expressing tetracycline inducible SIVA2 or the mutant SIVA2C73A were treated with TNF and the effect of SIVA2 or SIVA2C73A induction on TNF induced p65 translocation to the nucleus was studied. For this purpose, Ramos cells were treated with TNF for 0, 0.3 and 4 hours and induced to express SIVA2 or the mutant SIVA2C73A for long time (4 hours) or short time (1 hour) or were left without induction as described above. The cells were lysed, fractionated into nuclear and cytoplasmic extracts, and subjected to Western blot analysis probed with anti-p65 specific antibodies. The results obtained show that induction of wild type SIVA2 blocked TNF induced p65 translocation to the nucleus (FIG. 10D). In contrast, induction of the ring finger mutant of SIVA did not block TNF induced IκBα degradation and enhanced nuclear translocation of p65.

Thus, SIVA2 elevation, suppresses TNF induced NF-κB activation in Ramos cells.

Example 12

In Vitro Ubiquitination of TRAF2 by SIVA2

Figure 11:
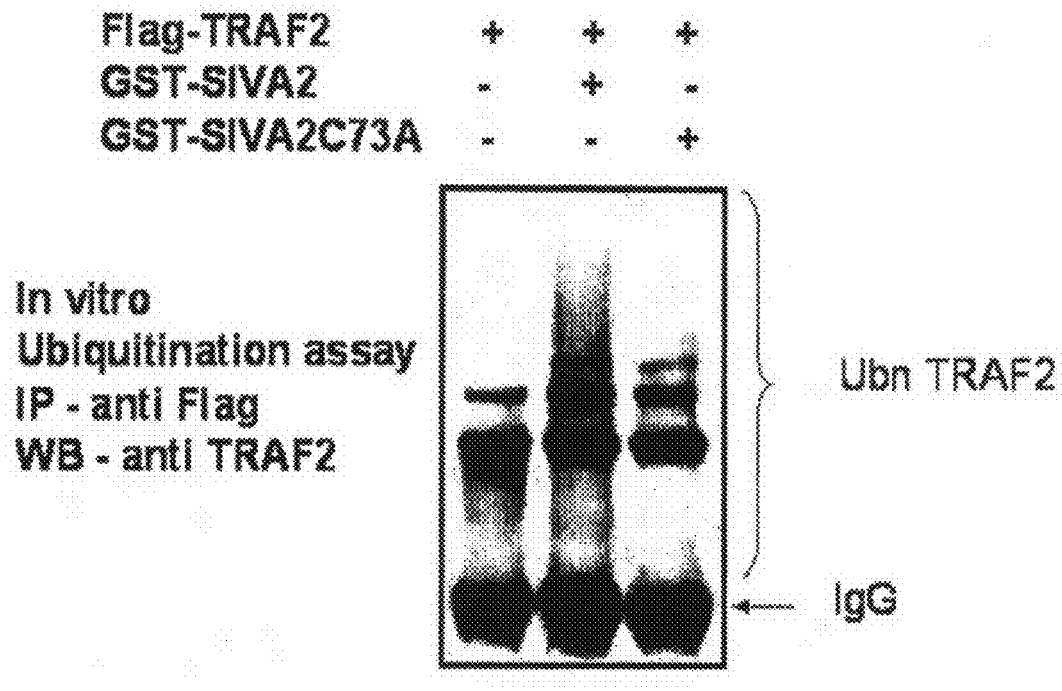
FIG. 11A-11G A. shows in vitro ubiquitination of TRAF2 by SIVA2. In vitro ubiquitination assays were performed in a reaction containing recombinant HIS-ubiquitin-K63 only, E1, E2 (Ubc13/Uev1 heterodimer) (both E1 an E2 were purchased from Boston Biochem) and of recombinant GST-SIVA or GST-SIVAC73A with FLAG tagged TRAF2 in a buffer containing, 30 mM HEPES pH 7.6, 5 mM MgCl2, 2 mM ATP, 0.2 mM DTT, 5 mM Sodium Citrate, 10 mM creatine phosphate, 0.2 μg/ml creatine kinase and 5 μM ubiquitin aldehyde. FLAG tagged TRAF2 was prepared by transfecting pcFLAG TRAF2 into HEK 293T cells. 24 hours post transfection cells were lysed in 1% Trition X100 containing lysis buffer and immunoprecipitated using anti FLAG M2 beads (Sigma). Immunoprecipitated TRAF2 was eluted with FLAG peptide and concentrated using microcon column (MWCO3000) and used in the in vitro ubiquitination reaction. Reactions were incubated at 30° C. for 1 hour. TRAF2 was immunoprecipitated using anti-FLAG M2 beads for 4 hours at 4° C. Immunoprecipitates were subjected to Western blotting with anti TRAF2 (H249, Santacruz) antibody. B. shows that Ramos cells which were engineered to stably express SIVA C terminus exhibit high level of p52 as well as TRAF3 and decreased expression of TRAF2. C. shows that TRAF2 binds to SIVA2. FLAG tagged TRAF2 was incubated at 30° C. for one hour with recombinant (bacterially expressed) GST tagged SIVA2 or GST tagged ring finger mutant SIVA2. Next, immunoprecipitation was carried out with anti-FLAG for TRAF2 and Western blotting analysis was carried out with anti SIVA to detect coprecipitating SIVA. Recombinant GST tagged bacterially expressed SIVA2 appears as two bands in western blots. Ring finger mutation in SIVA2 might cause conformational variation that results in altered binding affinity to TRAF2. This is in line with the observation in FIG. 11D, where TRAF2 was found to bind to SIVA2 ring finger. D. shows that the ring finger of SIVA is important for binding to TRAF2. HEK 293T cells were co-transfected with a plasmid encoding HIS-SIVA2 or deletions of SIVA2, SIVA2 1-58 lacking the ring finger or SIVA 1-81 and a plasmid encoding FLAG-TRAF2. 24 hours post transfection, cells were harvested and lysed. TRAF2 was immunoprecipitated using anti FLAG-M2 beads and coprecipitated SIVA2 was probed by Western blotting using anti HIS antibody. Total lysis shows the expression levels of the proteins. SIVA was not co-precipitated with TRAF2 when the ring finger is missing (SINA2 1-58) and co-precipitates only when the ring finger is present (intact SIVA2 and SIVA2 1-81). E. shows that overexpression of SIVA in HEK 293T cells enhances K48 ubiquitination of TRAF2. HEK 293T cells were transfected with plasmid encoding FLAG-TRAF2, HIS-SIVA2 and ubiquitin mutant. 24 hours post transfection cells were lysed immunoprecipitated and Western blot analysed using specific antibodies. TRAF2 ring finger mutant (C34A) was used to prevent its self ubiquitination. Ring finger mutation in TRAF2 prevented only self K63 ubiquitination. SIVA2 overexpression enhanced K48 ubiquitination of TRAF2 as a function of its ring finger. TRAF2 ring finger mutant retained its ability to bind SIVA2. F. shows that SIVA2 regulates ubiquitination of TRAF2 recruited to CD27 receptor in Ramos cells. TRAF2 recruitment to the CD27 receptor was induced by stimulation with FLAG-CD70 and TRAF2 recruited to the receptor was immunoprecipitated using anti-FLAG. SIVA2 was induced for 2 hours with 1 uM doxycycline before stimulation with CD70. IKK1 recruitment to CD27 receptor is not affected by SIVA induction. Amount of total SIVA2 expressed after doxycycline induction is shown in the bottom panel. SIVA2 induction increases ubiquitinated TRAF2 in the receptor complex in a ring dependent manner in Ramos cells G. Shows the effect of silencing SIVA on ubiquitination of TRAF2 recruited to the CD27 receptor. 293-CD27 cells were transfected with pSUPER SIVA and 48 hours later, treated with FLAG-CD70 expressing medium for 0, 15, 30 and 60 minutes, lysed and the CD27 receptor complex was immunoprecipitated using anti-FLAG antibody. Receptor associated TRAF2 was probed with anti-TRAF2 antibody. CD27 receptor and IKK1 precipitated through the ligand are shown in the bottom panels. SIVA facilitates initial TRAF2 recruitment to CD27 receptor, which is necessary for TRAF2 degradation following CD27 stimulation pSUPER SIVA transfected cells were compared to control pSUPER transfected cells for the level of TRAF2 in the cytoplasm following CD70 stimulation. CD70 triggering results in degradation of TRAF2 in a SIVA dependent manner.
Figure 11:
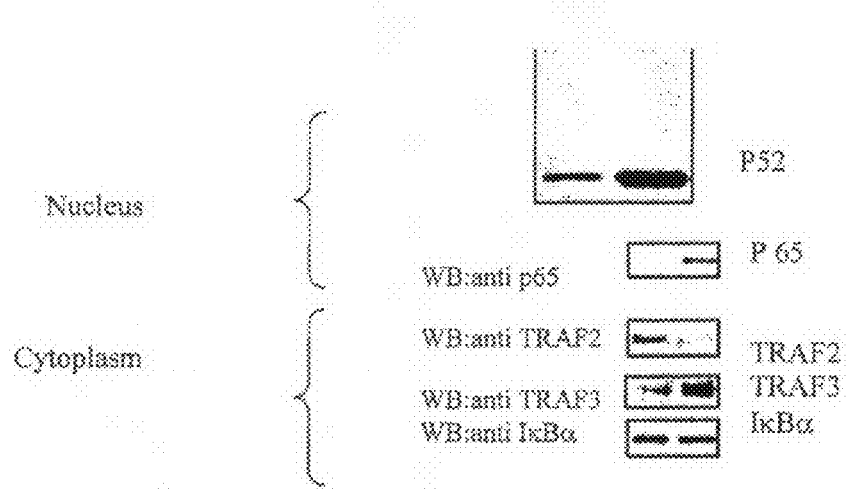

In vitro ubiquitination assays were performed in a 50 μl reaction volume containing recombinant HIS-ubiquitin-K63 only (a recombinant HIS-ubiquitin where all the lysines in the ubiquitin except K63 are mutated to arginine, Boston Biochem) (8 μg), E1 (0.2 μg), E2 (0.5 μg) and 1-2 μg of recombinant GST-SIVA or GST-SIVAC73A with FLAG tagged TRAF2. FLAG tagged TRAF2 was transiently expressed and purified using anti FLAG M2 beads (Sigma) and eluted using FLAG peptide in a buffer containing, 30 mM HEPES pH 7.6, 5 mM MgCl2, 2 mM ATP, 0.2 mM DTT, 5 mM Sodium Citrate, 10 mM creatine phosphate, 0.2 μg/ml creatine kinase and 5 μM ubiquitin aldehyde. Reactions were incubated at 30° C. for 1 hour. The reactions were diluted to 1 ml with buffer containing 20 mM HEPES pH 7.6, 150 mM NaCl, 1% Triton X-100, 1 mM EDTA and complete protease inhibitor cocktail. TRAF2 was immunoprecipitated using anti-FLAG M2 beads for 4 hours at 4° C. Immunoprecipitates were subjected to Western blotting with anti TRAF2 (H249, Santacruz) antibody. The results in FIG. 11A show that SIVA2, but not the mutant SIVA2C73A, directly induces K63 ubiquitination of TRAF2.

Example 13

Ramos Cells Constitutively Expressing SIVA-C Terminus Mimics TRAF2 Deficiency in B Cells TRAF2 deficient B cells display high level of p52 (constitutive alternative NF-κB) and TRAF3 (Grech et al., 2004). Similarly, it was found that Ramos cells which were engineered to stably express SIVA C terminus show high level of p52 as well as TRAF3 and decreased expression of TRAF2 (FIG. 11B). The hyper NF-κB activation resulting from SIVAc expression may result in enhanced expression of NF-κB dependent immunomediators from cells.

Example 14

In Vitro Binding of TRAF2 to SIVA2

Figure 11C:
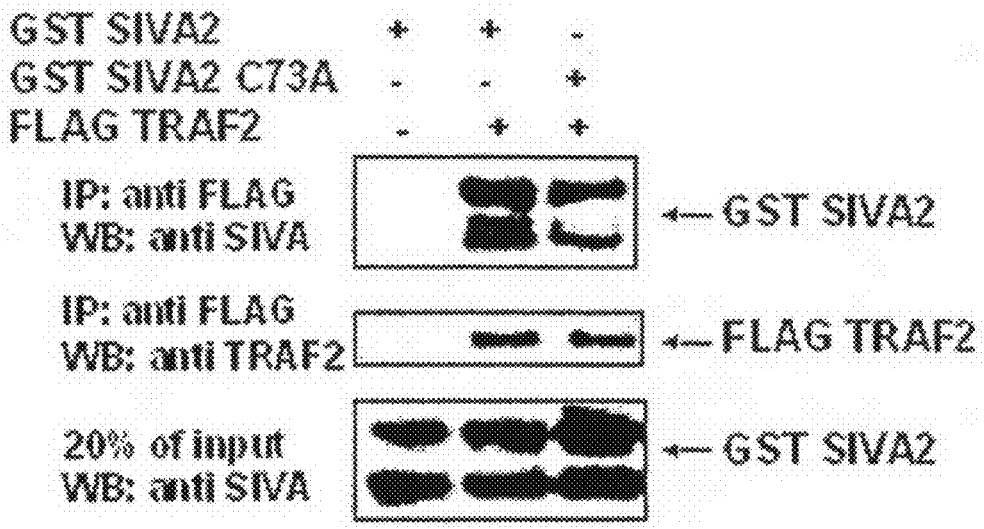
Figure 11D:
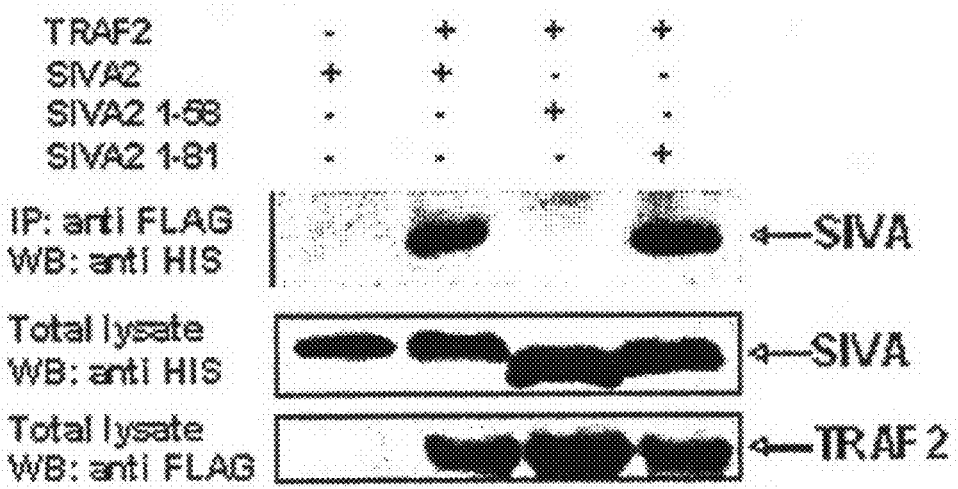

In order to explore whether TRAF2 binds to SIVA2, FLAG tagged TRAF2 was immuno-precipitated from transfected 193T cells using anti-FLAG M2 beads. TRAF2 was eluted from the beads using FLAG peptide. The eluted FLAG tagged TRAF2 was incubated with recombinant (bacterially expressed) GST tagged SIVA2 or GST tagged ring finger mutant SIVA2 at 30° C. for one hour in a volume of 50 μl of buffer (30 mM HEPES, pH 7.6, 5 mM MgCl2, 0.2 mM DTT). Next, the binding mix was diluted to 1 ml to attain the following composition –30 mM HEPES, 5 mM MgCl2, 0.2 mM DTT, 150 mM NaCl, 1% Triton X100 and 1 mM EDTA. Immunoprecipitation was carried out with anti-FLAG for TRAF2 and Western blotting analysis was carried out with anti SIVA to detect coprecipitating SIVA. The results show that TRAF2 directly binds SIVA2 in vitro and that the ring finger of SIVA is important for this binding (FIG. 11C). The latter was confirmed in the following experiment. HEK 293T cells were co-transfected with 12 ug of HIS-SIVA2 or deletions of SIVA2 lacking the ring finger (SIVA2 1-58 and SIVA 1-81) and FLAG-TRAF2 by calcium phosphate method. 24 hours post transfection; cells were harvested and lysed in 1% Triton containing lysis buffer. TRAF2 was immunoprecipitated using anti FLAG-M2 beads and coprecipitated SIVA2 was probed by Western blotting using anti HIS antibody. Total lysis in FIG. 11D show the expression levels of the proteins. The results obtained show that SIVA is not co-precipitated with TRAF2 when the ring finger is missing (SINA2 1-58) and co-precipitates only when the ring finger is present (intact SIVA2 and SIVA2 1-81). These results confirm that the ring finger in SIVA2 is required for binding of TRAF2 and SIVA2. (FIG. 11D).

Example 15

Overexpression of SIVA in HEK 293T Cells Enhances K48 Ubiquitination of TRAF2

Figure 11E:
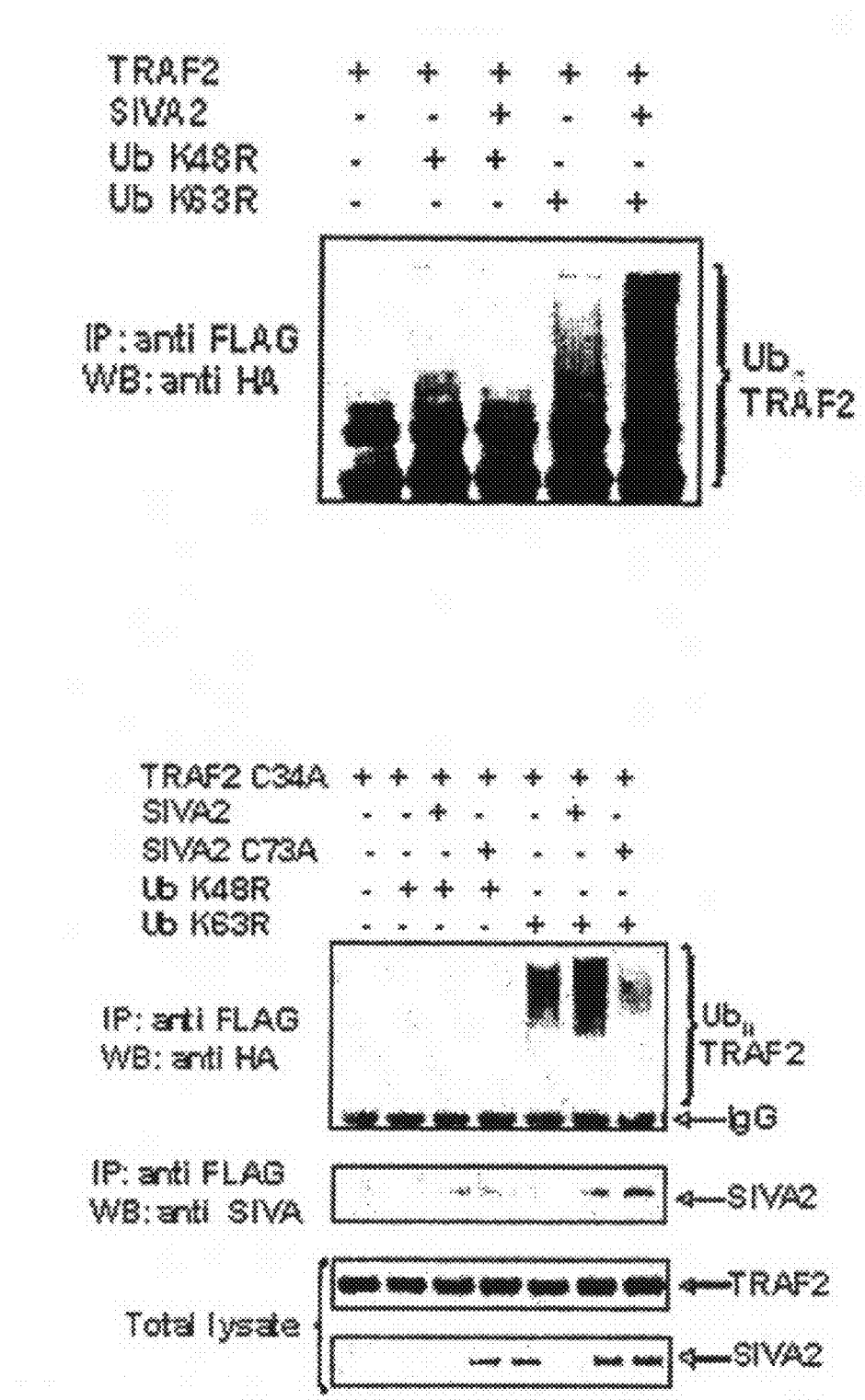

HEK 293T cells were transfected by calcium phosphate method with 4 μg of FLAG-TRAF2, 6ug of HIS-SIVA2 and 6 μg of ubiquitin mutant plasmids. 24 hours post transfection cells were lysed in 1% TritonX100 containing buffer and immunoprecipitated and Western blot analysed using specific antibodies. TRAF2 ring finger mutant (C34A) was used to prevent its self ubiquitination. Ring finger mutation in TRAF2 prevented only self K63 ubiquitination. SIVA2 enhanced K48 ubiquitination of TRAF2 as a function of its ring finger. TRAF2 ring finger mutant retained its ability to bind SIVA2 (FIG. 11E).

Example 16

Figure 11F:
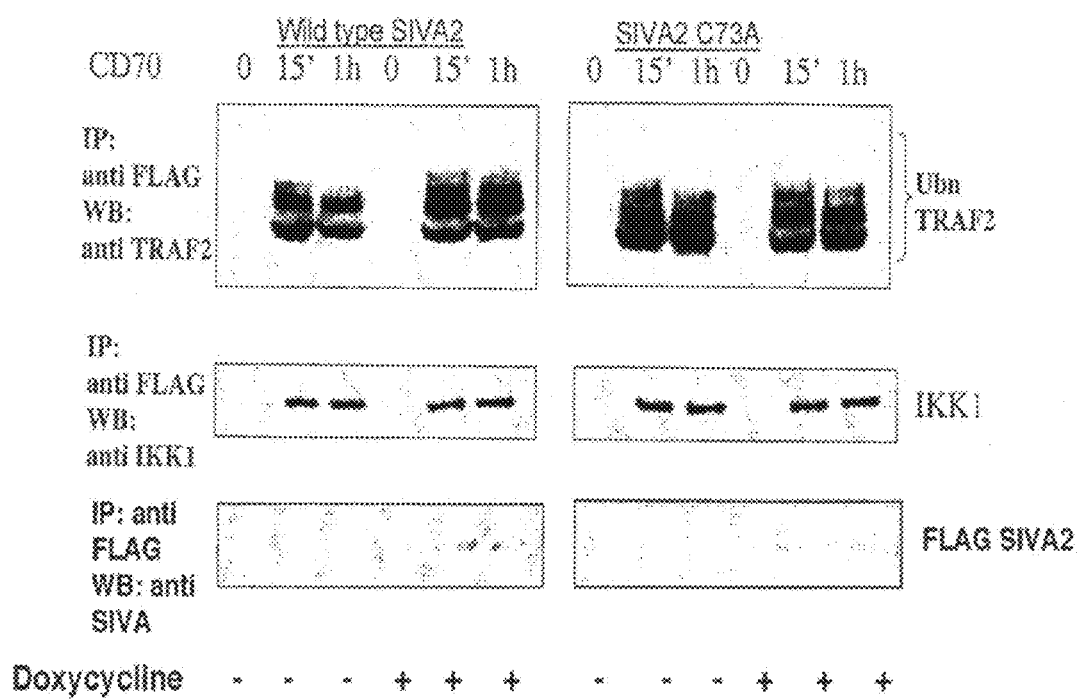
Figure 11G:
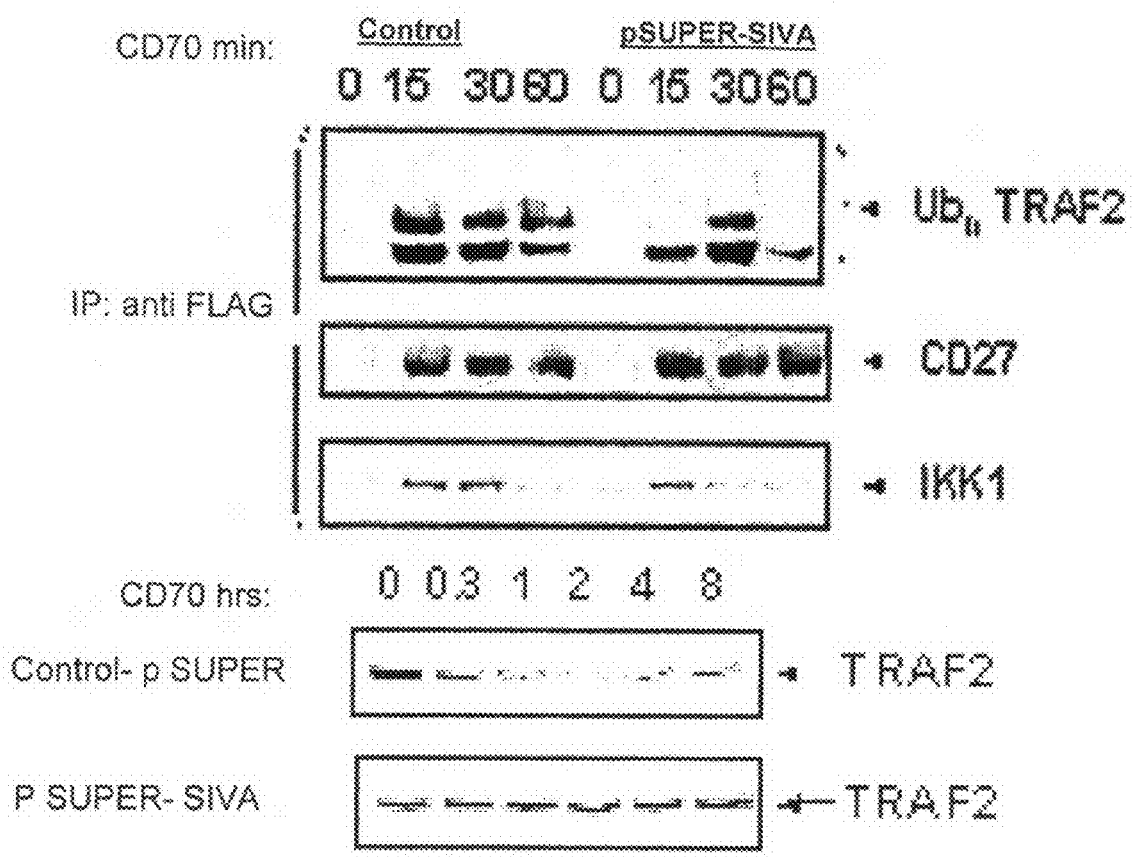

SIVA2 Regulates Ubiquitination of TRAF2 Recruited to CD27 Receptor in Ramos Cells TRAF2 recruitment to the CD27 receptor was induced by stimulation with FLAG-CD70 and TRAF2 recruited to the receptor was immunoprecipitated using anti-FLAG trough FLAG-CD70 from $100 \times 10^6$ cells per time point. SIVA2 was induced for 2 hours with 1 μM doxycycline before stimulation with CD70. IKK1 recruitment to CD27 receptor is not affected by SIVA induction. Amount of total SIVA2 expressed after doxycycline induction is shown in the bottom panel. SIVA2 induction increases ubiquitinated TRAF2 in the receptor complex in a ring dependent manner in Ramos cells (FIG. 11F).

The effect of silencing of SIVA in TRAF2 ubiquitination recruited to the CD27 receptor was explored. For this purpose, 293-CD27 cells were transfected in 6 well plates with 3 μg of pSUPER SIVA (2 ug pSUPER275+1 ug pSUPER NC3) by calcium phosphate method. 48 hours later, cells were treated with FLAG-CD70 expressing medium for 0, 15, 30 and 60 minutes to induce recruitment of TRAF2 to the CD27 receptor. Cells were lysed and the CD27 receptor complex was immunoprecipitated using anti-FLAG antibody. Receptor associated TRAF2 was probed with anti-TRAF2 (Santa Cruz H249) antibody. CD27 receptor and IKK1 precipitated through the ligand are shown in the bottom panels. B pSUPER SIVA transfected cells were compared to control pSUPER transfected cells for the level of TRAF2 in the cytoplasm following CD70 stimulation. CD70 triggering results in degradation of TRAF2 in a SIVA dependent manner. SIVA facilitates initial TRAF2 recruitment to CD27 receptor, which is necessary for TRAF2 degradation following CD27 stimulation.

REFERENCES

Bradley, J. R., and Pober, J. S. (2001). Tumor necrosis factor receptor-associated factors (TRAFs). Oncogene 20, 6482-6491.

Brummelkamp, T. R., Bernards, R., and Agami, R. A system for stable expression of short interfering RNAs in mammalian cells. Science 296, 550-553. 2002.

Bishop, G. A. (2004). The multifaceted roles of TRAFs in the regulation of B-cell function. Nat Rev Immunol 4, 775-786.

Canicio, J., Ruiz-Lozano, P., Carrasco, M., Palacin, M., Chien, K., Zorzano, A., and Kaliman, P. (2001). Nuclear factor kappa B-inducing kinase and Ikappa B kinase-alpha signal skeletal muscle cell differentiation. J Biol Chem 276, 20228-20233.

Cao, C., Ren, X., Kharbanda, S., Koleske, A., Prasad, K. V., and Kufe, D. The ARG tyrosine kinase interacts with Siva-1 in the apoptotic response to oxidative stress. J Biol Chem 276, 11465-11468. 2001

Chu, F., Barkinge, J., Hawkins, S., Gudi, R., Salgia, R., and Kanteti, P. V. Expression of Siva-1 protein or its putative amphipathic helical region enhances cisplatin-induced apoptosis in breast cancer cells: effect of elevated levels of BCL-2. Cancer Res 65, 5301-5309. 2005

Chu, F., Borthakur, A., Sun, X., Barkinge, J., Gudi, R., Hawkins, S., and Prasad, K. V. The Siva-1 putative amphipathic helical region (SAH) is sufficient to bind to BCL-XL and sensitize cells to UV. 2004

Fanslow, W. C., Clifford, K. N., Seaman, M., Alderson, M. R., Spriggs, M. K., Armitage, R. J., and Ramsdell, F. Recombinant CD40 ligand exerts potent biologic effects on T cells. J Immunol 152, 4262-4269. 1994

Choudhary, S., Boldogh, S., Garofalo, R., Jamaluddin, M., and Brasier, A. R. (2005). Respiratory syncytial virus influences NF-kappaB-dependent gene expression through a novel pathway involving MAP3K14/NIK expression and nuclear complex formation with NF-kappaB2. J Virol 79, 8948-8959.

Chung, J. Y., Park, Y. C., Ye, H., and Wu, H. All TRAFs are not created equal: common and distinct molecular mechanisms of TRAF-mediated signal transduction. J Cell Sci 115, 679-688. 2002

Deng, L., Wang, C., Spencer, E., Yang, L., Braun, A., You, J., Slaughter, C., Pickart, C., and Chen, Z. J. Activation of the IkappaB kinase complex by TRAF6 requires a dimeric ubiquitin-conjugating enzyme complex and a unique polyubiquitin chain. Cell 103, 351-361.98.2000

Foehr, E. D., Bohuslav, J., Chen, L. F., DeNoronha, C., Geleziunas, R., Lin, X., O'Mahony, A., and Greene, W. C. The NF-kappa B-inducing kinase induces PC12 cell differentiation and prevents apoptosis. J Biol Chem 275, 34021-34024. 2000.

Fontanari Krause et al, Abstract 3152, Blood, Vol: 102, 11, Nov. 16, 2003.

Fortin, A., MacLaurin, J. G., Arbour, N., Cregan, S. P., Kushwaha, N., Callaghan, S. M., Park, D. S., Albert, P. R., and Slack, R. S. The prbapoptotic gene SIVA is a direct transcriptional target for the tumor suppressors p53 and E2F1. J Biol Chem 279, 28706-28714. 2004

Fred M. Ausubel, R. B., Robert E. Kingston, David D. Moore, J. G. Seidman, John A. Smith, Kevin Struhl, ed. Current protocols in molecular biology. 1996

Glickman, M. H., and Ciechanover, A. The ubiquitin-proteasome proteolytic pathway: destruction for the sake of construction. Physiol Rev 82, 373-428. 2002

Grech, A. P., Amesbury, M., Chan, T., Gardam, S., Basten, A., and Brink, R. TRAF2 differentially regulates the canonical and noncanonical pathways of NF-kappaB activation in mature B cells. Immunity 21, 629-642. 2004

Henke, A., Launhardt, H., Klement, K., Stelzner, A., Zell, R., and Munder, T. Apoptosis in coxsackievirus B3-caused diseases: interaction between the capsid protein VP2 and the proapoptotic protein siva. J Virol 74, 4284-4290. 2000

Hofmann, K., and Falquet, L. A ubiquitin-interacting motif conserved in components of the proteasomal and lysosomal protein degradation systems. Trends Biochem Sci 26, 347-350. 2001

Hofmann, R. M., and Pickart, C. M. In vitro assembly and recognition of Lys-63 polyubiquitin chains. J Biol Chem 276, 27936-27943. 2001

Karin, M., and Ben-Neriah, Y. Phosphorylation meets ubiquitination: the control of NF-[kappa]B activity. Annu Rev Immunol 18, 621-663. 2000

Kajiura, F., Sun, S., Nomura, T., Izumi, K., Ueno, T., Bando, Y., Kuroda, N., Han, H., Li, Y., Matsushima, A., et al. (2004). NF-kappa B-inducing kinase establishes self-tolerance in a thymic stroma-dependent manner. J Immunol 172, 2067-2075.

Kovalenko, A., Chable-Bessia, C., Cantarella, G., Israel, A., Wallach, D., and Courtois, G. The tumour suppressor CYLD negatively regulates NF-kappaB signalling by deubiquitination. Nature 424, 801-805.2003

Lee, Z. H., Lee, S. E., Kwack, K., Yeo, W., Lee, T. H., Bae, S. S., Suh, P. G., and Kim, H. H. Caspase-mediated cleavage of TRAF3 in FasL-stimulated Jurkat-T cells. J Leukoc Biol 69, 490-496. 2001

Liao, G., Zhang, M., Harhaj, E. W., and Sun, S. C. Regulation of the NF-kappaB-inducing kinase by tumor necrosis factor receptor-associated factor 3-induced degradation. J Biol Chem 279, 26243-26250. 2004

Lois, C., Hong, E. J., Pease, S., Brown, E. J., and Baltimore, D. Germline transmission and tissue-specific expression of transgenes delivered by lentiviral vectors. Science 295, 868-872. 2002

Malinin, N. L., Boldin, M. P., Kovalenko, A. V., and Wallach, D. MAP3K-related kinase involved in NF-kappaB induction by TNF, CD95 and IL-1. Nature 385, 540-544. 1997

Miyawaki, S., Nakamura, Y., Suzuka, H., Koba, M., Yasumizu, R., Ikehara, S., and Shibata, Y. (1994). A new mutation, aly, that induces a generalized lack of lymph nodes accompanied by immunodeficiency in mice. Eur J Immunol 24, 429-434.

Nocentini, G., and Riccardi, C. GITR: a multifaceted regulator of immunity belonging to the tumor necrosis factor receptor superfamily. Eur J Immunol 35, 1016-1022. 2005

Padanilam, B. J., Lewington, A. J., and Hammerman, M. R. Expression of CD27 and ischemia/reperfusion-induced expression of its ligand Siva in rat kidneys. Kidney Int 54, 1967-1975. 1998

Petit PX, P. B., Mrugala D, Biard-Piechaczyk M, Benichou S. SIVA: A new intracellular ligand of the CD4 receptor modulating T lymphocyte apoptosis via a caspase-dependent mitochondrial pathway, Paper presented at: ISAC congress XXII (France: WILEY-LISS, DIV JOHN WILEY & SONS INC, 111 RIVER ST, HOBOKEN, N.J. 07030 USA). 2004

Pickart, C. M. Mechanisms underlying ubiquitination. Annu Rev Biochem 70, 503-533. 2001

Prasad, K. V., Ao, Z., Yoon, Y., Wu, M. X., Rizk, M., Jacquot, S., and Schlossman, S. F. CD27, a member of the tumor necrosis factor receptor family, induces apoptosis and binds to Siva, a proapoptotic protein. Proc Natl Acad Sci USA 94, 6346-6351. 1997

Pomerantz, J. L., and Baltimore, D. (2002). Two pathways to NF-kappaB. Mol Cell 10, 693-695.

Prasad, K. V., Ao, Z., Yoon, Y., Wu, M. X., Rizk, M., Jacquot, S., and Schlossman, S. F. (1997). CD27, a member of the tumor necrosis factor receptor family, induces apoptosis and binds to Siva, a proapoptotic protein. Proc Natl Acad Sci USA 94, 6346-6351.

Py, B., Slomianny, C., Auberger, P., Petit, P. X., and Benichou, S. Siva-1 and an alternative splice form lacking the death domain, Siva-2, similarly induce apoptosis in T lymphocytes via a caspase dependent mitochondrial pathway. J Immunol 172, 4008-4017. 2004

Qin, L. F., Lee, T. K., and Ng, I. O. Gene expression profiling by cDNA array in human hepatoma cell line in response to cisplatin treatment. Life Sci 70, 1677-1690. 2002

Ramakrishnan, P., Wang, W., and Wallach, D. Receptor-specific signaling for both the alternative and the canonical NF-kappaB activation pathways by NF-kappaB-inducing kinase. Immunity 21, 477-489. 2004

Rigaut, G., Shevehenko, A., Rutz, B., Wilm, M., Mann, M., and Seraphin, B. A generic protein purification method for protein complex characterization and proteome exploration. Nat Biotechnol 17, 1030-1032. 1999

Senftleben, U., Cao, Y., Xiao, G., Greten, F. R., Krahn, G., Bonizzi, G., Chen, Y., Hu, Y., Fong, A., Sun, S. C., and Karin, M. Activation by IKKalpha of a second, evolutionary conserved, NF-kappa B signaling pathway. Science 293, 1495-1499. 2001

Shinkura, R., Kitada, K., Matsuda, F., Tashiro, K., Ikuta, K., Suzuki, M., Kogishi, K., Serikawa, T., and Honjo, T. Alymphoplasia is caused by a point mutation in the mouse gene encoding Nf-kappa b inducing kinase. Nat Genet 22, 74-77.107. 1999

Schreiber, E., Matthias, P., Muller, M. M., and Schaffner, W. Rapid detection of octamer binding proteins with 'mini-extracts', prepared from a small number of cells. Nucleic Acids Res 17, 6419. 1989

Spinicelli, S., Nocentini, G., Ronchetti, S., Krausz, L. T., Bianchini, R., and Riccardi, C. GITR interacts with the pro-apoptotic protein Siva and induces apoptosis. Cell Death Differ 9, 1382-1384.2002

Wajant, H., and Scheurich, P. (2004). Analogies between Drosophila and mammalian TRAF pathways. Prog Mol Subcell Biol 34, 47-72.

Xiao, G., Fong, A., and Sun, S. C. Induction of p100 processing by NF-kappaB-inducing kinase involves docking IkappaB kinase alpha (IKKalpha) to p100 and IKKalpha-mediated phosphorylation. J Biol Chem 279, 30099-30105. 2004

Xiao, G., and Sun, S. C. Negative regulation of the nuclear factor kappa B-inducing kinase by a cis-acting domain. J Biol Chem 275, 21081-21085. 2000

Xu, L. G., Li, L. Y., and Shu, H. B. (2004). TRAF7 potentiates MEKK3-induced AP1 and CHOP activation and induces apoptosis. J Biol Chem 279, 17278-17282.

Xue, L., Chu, F., Cheng, Y., Sun, X., Borthakur, A., Ramarao, M., Pandey, P., Wu, M., Schlossman, S. F., and Prasad, K. V. Siva-1 binds to and inhibits BCL-X(L)-mediated protection against UV. 2002

Yoon, Y., Ao, Z., Cheng, Y., Schlossman, S. F., and Prasad, K. V. Murine Siva-1 and Siva-2, alternate splice forms of the mouse Siva gene, both bind to CD27 but differentially transduce apoptosis. Oncogene 18, 7174-7179. 1999

---

The invention claimed is:

1. A method for identifying a polypeptide that comprises a B-box-like ring with the amino acid sequence of SEQ ID NO:6, wherein said SEQ ID NO:6 has eight Cysteines and no Histidine, or a homolog thereof, said homolog comprising a B-box-like ring finger motif with eight cysteines, and no histidine, and an amino acid sequence that is at least 80% identical to that set forth in SEQ ID NO:6 and wherein said polypeptide is capable of self-ubiquitination, the method comprising:
   (i) contacting polypeptides comprising an ubiquitin, an E1 ubiquitin-activating enzyme, an E2 ubiquitin conjugating enzyme, and the polypeptide comprising said B-box-like ring with the amino acid sequence of SEQ ID NO:6 or homolog thereof; and
   (ii) measuring linkage of ubiquitin to said polypeptide comprising said B-box-like ring with the amino acid sequence of SEQ ID NO:6 or homoloq thereof,
   wherein the measurement of ubiquitin linked to said polypeptide comprising said B-box-like ring identifies said polypeptide as a polypeptide comprising said B-box-like ring capable of self-ubiquitination.

2. The method of claim 1 wherein the polypeptide comprising said B-box-like ring or a homolog thereof is a SIVA polypeptide.

3. The method according to claim 2, wherein the polypeptide comprising the B-box-like ring with the amino acid sequence of SEQ ID NO:6 or homoloq thereof is capable of self-ubiquitination by covalent linkage with the amino acid K63 of ubiquitin.

4. The method according to claim 2, wherein the ubiquitin polypeptide is ubiquitin mutated at K48.

5. The method according to claim 1 or claim 2 wherein said contacting of polypeptides is carried out inside cells or in vitro.

6. The method according to claim 1 or claim 2 wherein said ubiquitination is detected by Western blot analysis.

7. The method of claim 1, wherein the B-box-like ring comprises the amino acid sequence of SEQ ID NO:6.

* * * * *

SEQUENCE LISTING

```
<160> NUMBER OF SEQ ID NOS: 35

<210> SEQ ID NO 1
<211> LENGTH: 175
<212> TYPE: PRT
<213> ORGANISM: Homo sapiens

<400> SEQUENCE: 1

Met Pro Lys Arg Ser Cys Pro Phe Ala Asp Val Ala Pro Leu Gln Leu
1               5                   10                  15

Lys Val Arg Val Ser Gln Arg Glu Leu Ser Arg Gly Val Cys Ala Glu
            20                  25                  30

Arg Tyr Ser Gln Glu Val Phe Glu Lys Thr Lys Arg Leu Leu Phe Leu
        35                  40                  45

Gly Ala Gln Ala Tyr Leu Asp His Val Trp Asp Glu Gly Cys Ala Val
    50                  55                  60

Val His Leu Pro Glu Ser Pro Lys Pro Gly Pro Thr Gly Ala Pro Arg
65                  70                  75                  80

Ala Ala Arg Gly Gln Met Leu Ile Gly Pro Asp Gly Arg Leu Ile Arg
                85                  90                  95

Ser Leu Gly Gln Ala Ser Glu Ala Asp Pro Ser Gly Val Ala Ser Ile
            100                 105                 110

Ala Cys Ser Ser Cys Val Arg Ala Val Asp Gly Lys Ala Val Cys Gly
        115                 120                 125

Gln Cys Glu Arg Ala Leu Cys Gly Gln Cys Val Arg Thr Cys Trp Gly
    130                 135                 140

Cys Gly Ser Val Ala Cys Thr Leu Cys Gly Leu Val Asp Cys Ser Asp
145                 150                 155                 160

Met Tyr Glu Lys Val Leu Cys Thr Ser Cys Ala Met Phe Glu Thr
                165                 170                 175

<210> SEQ ID NO 2
<211> LENGTH: 110
<212> TYPE: PRT
<213> ORGANISM: Homo sapiens

<400> SEQUENCE: 2

Met Pro Lys Arg Ser Cys Pro Phe Ala Asp Val Ala Pro Leu Gln Leu
1               5                   10                  15
```

```
Lys Val Arg Val Ser Gln Arg Glu Leu Ser Arg Gly Val Cys Ala Glu
             20                  25                  30

Arg Tyr Ser Gln Glu Val Phe Asp Pro Ser Gly Val Ala Ser Ile Ala
         35                  40                  45

Cys Ser Ser Cys Val Arg Ala Val Asp Gly Lys Ala Val Cys Gly Gln
     50                  55                  60

Cys Glu Arg Ala Leu Cys Gly Gln Cys Val Arg Thr Cys Trp Gly Cys
 65                  70                  75                  80

Gly Ser Val Ala Cys Thr Leu Cys Gly Leu Val Asp Cys Ser Asp Met
                 85                  90                  95

Tyr Glu Lys Val Leu Cys Thr Ser Cys Ala Met Phe Glu Thr
             100                 105                 110

<210> SEQ ID NO 3
<211> LENGTH: 52
<212> TYPE: PRT
<213> ORGANISM: Artificial
<220> FEATURE:
<223> OTHER INFORMATION: SIVA C

<400> SEQUENCE: 3

Lys Ala Val Cys Gly Gln Cys Glu Arg Ala Leu Cys Gly Gln Cys Val
 1               5                   10                  15

Arg Thr Cys Trp Gly Cys Gly Ser Val Ala Cys Thr Leu Cys Gly Leu
             20                  25                  30

Val Asp Cys Ser Asp Met Tyr Glu Lys Val Leu Cys Thr Ser Cys Ala
         35                  40                  45

Met Phe Glu Thr
     50

<210> SEQ ID NO 4
<211> LENGTH: 58
<212> TYPE: PRT
<213> ORGANISM: Artificial
<220> FEATURE:
<223> OTHER INFORMATION: SIVA2 1-58

<400> SEQUENCE: 4

Met Pro Lys Arg Ser Cys Pro Phe Ala Asp Val Ala Pro Leu Gln Leu
 1               5                   10                  15

Lys Val Arg Val Ser Gln Arg Glu Leu Ser Arg Gly Val Cys Ala Glu
             20                  25                  30

Arg Tyr Ser Gln Glu Val Phe Asp Pro Ser Gly Val Ala Ser Ile Ala
         35                  40                  45

Cys Ser Ser Cys Val Arg Ala Val Asp Gly
     50                  55

<210> SEQ ID NO 5
<211> LENGTH: 81
<212> TYPE: PRT
<213> ORGANISM: Artificial
<220> FEATURE:
<223> OTHER INFORMATION: SIVA2 1-81

<400> SEQUENCE: 5

Met Pro Lys Arg Ser Cys Pro Phe Ala Asp Val Ala Pro Leu Gln Leu
 1               5                   10                  15

Lys Val Arg Val Ser Gln Arg Glu Leu Ser Arg Gly Val Cys Ala Glu
             20                  25                  30

Arg Tyr Ser Gln Glu Val Phe Asp Pro Ser Gly Val Ala Ser Ile Ala
```

```
                    35                  40                  45
Cys Ser Ser Cys Val Arg Ala Val Asp Gly Lys Ala Val Cys Gly Gln
     50                  55                  60
Cys Glu Arg Ala Leu Cys Gly Gln Cys Val Arg Thr Cys Trp Gly Cys
 65                  70                  75                  80

Gly

<210> SEQ ID NO 6
<211> LENGTH: 32
<212> TYPE: PRT
<213> ORGANISM: Artificial
<220> FEATURE:
<223> OTHER INFORMATION: B-box - like ring finger

<400> SEQUENCE: 6

Cys Ser Ser Cys Val Arg Ala Val Asp Gly Lys Ala Val Cys Gly Gln
 1               5                  10                  15
Cys Glu Arg Ala Leu Cys Gly Gln Cys Val Arg Thr Cys Trp Gly Cys
             20                  25                  30

<210> SEQ ID NO 7
<211> LENGTH: 156
<212> TYPE: DNA
<213> ORGANISM: Artificial
<220> FEATURE:
<223> OTHER INFORMATION: SIVA C Terminus

<400> SEQUENCE: 7
aaggcggtct gcggtcagtg tgagcgagcc ctgtgcgggc agtgtgtgcg cacctgctgg      60
ggctgcggct ccgtggcctg taccctgtgt ggcctcgtgg actgcagtga catgtacgag     120
aaagtgctgt gcaccagctg tgccatgttc gagacc                               156

<210> SEQ ID NO 8
<211> LENGTH: 174
<212> TYPE: DNA
<213> ORGANISM: Artificial
<220> FEATURE:
<223> OTHER INFORMATION: SIVA2 1-58

<400> SEQUENCE: 8
atgcccaagc ggagctgccc cttcgcggac gtggccccgc tacagctcaa ggtccgcgtg      60
agccagaggg agttgagccg cggcgtgtgc gccgagcgct actcgcagga ggtcttcgac     120
ccatctgggg tagcgtccat tgcctgttcc tcatgcgtgc gagccgtgga tggg           174

<210> SEQ ID NO 9
<211> LENGTH: 243
<212> TYPE: DNA
<213> ORGANISM: Artificial
<220> FEATURE:
<223> OTHER INFORMATION: SIVA2 1-81

<400> SEQUENCE: 9
atgcccaagc ggagctgccc cttcgcggac gtggccccgc tacagctcaa ggtccgcgtg      60
agccagaggg agttgagccg cggcgtgtgc gccgagcgct actcgcagga ggtcttcgac     120
ccatctgggg tagcgtccat tgcctgttcc tcatgcgtgc gagccgtgga tgggaaggcg     180
gtctgcggtc agtgtgagcg agccctgtgc gggcagtgtg tgcgcacctg ctggggctgc    240
ggc                                                                   243

<210> SEQ ID NO 10
```

```
<211> LENGTH: 528
<212> TYPE: DNA
<213> ORGANISM: Homo sapiens

<400> SEQUENCE: 10
atgcccaagc ggagctgccc cttcgcggac gtggccccgc tacagctcaa ggtccgcgtg      60
agccagaggg agttgagccg cggcgtgtgc gccgagcgct actcgcagga ggtcttcgag     120
aagaccaagc gactcctgtt cctcggggcc caggcctacc tggaccacgt gtgggatgaa     180
ggctgtgccg tcgttcacct gccagagtcc ccaaagcctg ccctacagg ggccccgagg      240 gctgcacgtg ggcagatgct gattggacca gacggccgcc tgatcaggag ccttgggcag    300
gcctccgaag ctgacccatc tggggtagcg tccattgcct gttcctcatg cgtgcgagcc    360
gtggatggga aggcggtctg cggtcagtgt gagcgagccc tgtgcgggca gtgtgtgcgc    420
acctgctggg gctgcggctc cgtggcctgt accctgtgtg gcctcgtgga ctgcagtgac    480
atgtacgaga aagtgctgtg caccagctgt gccatgttcg agacctga                 528

<210> SEQ ID NO 11
<211> LENGTH: 343
<212> TYPE: DNA
<213> ORGANISM: Homo sapiens

<400> SEQUENCE: 11
atgcccaagc ggagctgccc cttcgcggac gtggccccgc tacagctcaa ggtccgcgtg      60
agccagaggg agttgagccg cggcgtgtgc gccgagcgct actcgcagga ggtcttcgac    120
ccatctgggg tagcgtccat tgcctgttcc tcatgcgtgc gagccgtgga tgggaaggcg    180
gtctgcggtc agtgtgagcg agccctgtgc gggcagtgtg tgcgcacctg ctggggctgc    240
ggctccgtgg cctgtaccct gtgtggcctc gtggactgca gtgacatgta cgagaaagtg    300
ctgtgcacca gctgtgccat gttcgagacc tgaggctggc tca                      343

<210> SEQ ID NO 12
<211> LENGTH: 34
<212> TYPE: DNA
<213> ORGANISM: Artificial
<220> FEATURE:
<223> OTHER INFORMATION: Primer- sense

<400> SEQUENCE: 12
ccaagctatt tcaatcgtgt gaaagtccaa atac                                  34

<210> SEQ ID NO 13
<211> LENGTH: 34
<212> TYPE: DNA
<213> ORGANISM: Artificial
<220> FEATURE:
<223> OTHER INFORMATION: Primer - antisense

<400> SEQUENCE: 13
gtatttggac tttcacacga ttgaaatagc ttgg                                  34

<210> SEQ ID NO 14
<211> LENGTH: 42
<212> TYPE: DNA
<213> ORGANISM: Artificial
<220> FEATURE:
<223> OTHER INFORMATION: Primer - sense

<400> SEQUENCE: 14
gagggtctgg aatacctaca ttcccgcagg attctgcatg gg                         42
```

<210> SEQ ID NO 15
<211> LENGTH: 42
<212> TYPE: DNA
<213> ORGANISM: Artificial
<220> FEATURE:
<223> OTHER INFORMATION: Primer - antisense

<400> SEQUENCE: 15
cccatgcaga atcctgcggg aatgtaggta ttccagaccc tc        42

<210> SEQ ID NO 16
<211> LENGTH: 42
<212> TYPE: DNA
<213> ORGANISM: Artificial
<220> FEATURE:
<223> OTHER INFORMATION: Primer - sense

<400> SEQUENCE: 16
catgagaagt tttctgtggc ggcataccta gtgcatgctc tg        42

<210> SEQ ID NO 17
<211> LENGTH: 42
<212> TYPE: DNA
<213> ORGANISM: Artificial
<220> FEATURE:
<223> OTHER INFORMATION: Primer - antisense

<400> SEQUENCE: 17
cagagcatgc actaggtatg ccgccacaga aaacttctca tg        42

<210> SEQ ID NO 18
<211> LENGTH: 36
<212> TYPE: DNA
<213> ORGANISM: Artificial
<220> FEATURE:
<223> OTHER INFORMATION: Primer - sense

<400> SEQUENCE: 18 gggcccccggc cagctgcggc gacaacaggc agagcc        36

<210> SEQ ID NO 19
<211> LENGTH: 36
<212> TYPE: DNA
<213> ORGANISM: Artificial
<220> FEATURE:
<223> OTHER INFORMATION: Primer - antisense

<400> SEQUENCE: 19
ggctctgcct gttgtcgccg cagctggccg gggccc        36

<210> SEQ ID NO 20
<211> LENGTH: 64
<212> TYPE: DNA
<213> ORGANISM: Artificial
<220> FEATURE:
<223> OTHER INFORMATION: siRNA SIVA -NC3- sense

<400> SEQUENCE: 20
gatcccctga ataaacctct ttatatttca agagaatata aagaggttta ttcattttg    60 gaaa        64

<210> SEQ ID NO 21
<211> LENGTH: 64
<212> TYPE: DNA
<213> ORGANISM: Artificial
<220> FEATURE:

<223> OTHER INFORMATION: siRNA SIVA-NC3-antisense

<400> SEQUENCE: 21
agcttttcca aaaatgaata aacctcttta tattctcttg aaatataaag aggtttattc    60
aggg                                                                64

<210> SEQ ID NO 22
<211> LENGTH: 64
<212> TYPE: DNA
<213> ORGANISM: Artificial
<220> FEATURE:
<223> OTHER INFORMATION: siRNA SIVA131- sense

<400> SEQUENCE: 22
gatccccgca gtgacatgta cgagaattca agagattctc gtacatgtca ctgctttttg    60
gaaa                                                                64

<210> SEQ ID NO 23
<211> LENGTH: 64
<212> TYPE: DNA
<213> ORGANISM: Artificial
<220> FEATURE:
<223> OTHER INFORMATION: siRNA SIVA131-antisense

<400> SEQUENCE: 23
agcttttcca aaaagcagtg acatgtacga gaatctcttg aattctcgta catgtcactg    60
cggg                                                                64

<210> SEQ ID NO 24
<211> LENGTH: 64
<212> TYPE: DNA
<213> ORGANISM: Artificial
<220> FEATURE:
<223> OTHER INFORMATION: siRNA SIVA275- sense

<400> SEQUENCE: 24
gatccccact gcagtgacat gtacgattca agagatcgta catgtcactg cagttttttg    60
gaaa                                                                64

<210> SEQ ID NO 25
<211> LENGTH: 64
<212> TYPE: DNA
<213> ORGANISM: Artificial
<220> FEATURE:
<223> OTHER INFORMATION: siRNA SIVA275-antisense

<400> SEQUENCE: 25
agcttttcca aaaactgca gtgacatgta cgatctcttg aatcgtacat gtcactgcag    60
tggg                                                                64

<210> SEQ ID NO 26
<211> LENGTH: 64
<212> TYPE: DNA
<213> ORGANISM: Artificial
<220> FEATURE:
<223> OTHER INFORMATION: siRNA SIVA278-sense

<400> SEQUENCE: 26
gatcccctag cgtccattgc ctgttcttca agagagaaca ggcaatggac gctatttttg    60
gaaa                                                                64

<210> SEQ ID NO 27

```
<211> LENGTH: 64
<212> TYPE: DNA
<213> ORGANISM: Artificial
<220> FEATURE:
<223> OTHER INFORMATION: siRNA SIVA278- antisense

<400> SEQUENCE: 27
agcttttcca aaaatagcgt ccattgcctg ttctctcttg aagaacaggc aatggacgct    60
aggg                                                                64

<210> SEQ ID NO 28
<211> LENGTH: 64
<212> TYPE: DNA
<213> ORGANISM: Artificial
<220> FEATURE:
<223> OTHER INFORMATION: siRNA SIVA518- sense

<400> SEQUENCE: 28
gatccccgtg acatgtacga gaaagtttca agagaacttt ctcgtacatg tcactttttg    60
gaaa                                                                64

<210> SEQ ID NO 29
<211> LENGTH: 64
<212> TYPE: DNA
<213> ORGANISM: Artificial
<220> FEATURE:
<223> OTHER INFORMATION: siRNA SIVA518- antisense

<400> SEQUENCE: 29
agcttttcca aaagtgaca tgtacgagaa agttctcttg aaactttctc gtacatgtca    60
cggg                                                                64

<210> SEQ ID NO 30
<211> LENGTH: 64
<212> TYPE: DNA
<213> ORGANISM: Artificial
<220> FEATURE:
<223> OTHER INFORMATION: siRNA SIVA521- sense

<400> SEQUENCE: 30
gatcccccca gctgtgccat gttcgattca agagatcgaa catggcacag ctggtttttg    60
gaaa                                                                64

<210> SEQ ID NO 31
<211> LENGTH: 64
<212> TYPE: DNA
<213> ORGANISM: Artificial
<220> FEATURE:
<223> OTHER INFORMATION: siRNA SIVA521- antisense

<400> SEQUENCE: 31
agcttttcca aaaccagct gtgccatgtt cgatctcttg aatcgaacat ggcacagctg    60
gggg                                                                64

<210> SEQ ID NO 32
<211> LENGTH: 64
<212> TYPE: DNA
<213> ORGANISM: Artificial
<220> FEATURE:
<223> OTHER INFORMATION: siRNA GFP- sense

<400> SEQUENCE: 32
gatccccgct acctgttcca tggccattca agagatggcc atggaacagg tagcttttg     60
```

```
<210> SEQ ID NO 33
<211> LENGTH: 64
<212> TYPE: DNA
<213> ORGANISM: Artificial
<220> FEATURE:
<223> OTHER INFORMATION: siRNA GFP- antisense

<400> SEQUENCE: 33
agcttttcca aaaagctacc tgttccatgg ccatctcttg aatggccatg gaacaggtag      60
cggg                                                                  64

<210> SEQ ID NO 34
<211> LENGTH: 17
<212> TYPE: PRT
<213> ORGANISM: Artificial
<220> FEATURE:
<223> OTHER INFORMATION: NIK kinase domain

<400> SEQUENCE: 34

Cys Arg Leu Gly Arg Gly Ser Phe Gly Glu Val His Arg Met Glu Asp
1               5                   10                  15

Lys

<210> SEQ ID NO 35
<211> LENGTH: 10
<212> TYPE: PRT
<213> ORGANISM: Artificial
<220> FEATURE:
<223> OTHER INFORMATION: myc Tag

<400> SEQUENCE: 35

Glu Gln Lys Leu Ile Ser Glu Glu Asp Leu
1               5                   10
```